United States Patent
Pore et al.

(10) Patent No.: US 10,829,554 B2
(45) Date of Patent: Nov. 10, 2020

(54) BINDING MOLECULES SPECIFIC FOR ASCT2 AND USES THEREOF

(71) Applicant: MedImmune, LLC, Gaithersburg, MD (US)

(72) Inventors: Nabendu Pore, Gaithersburg, MD (US); Martin J. Borrok, III, Gaithersburg, MD (US); Emil F. Michelotti, Gaithersburg, MD (US); David A. Tice, Gaithersburg, MD (US); Robert E. Hollingsworth, Gaithersburg, MD (US); Chien-Ying Chang, Gaithersburg, MD (US); Partha Chowdhury, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 362 days.

(21) Appl. No.: 15/774,351

(22) PCT Filed: Nov. 10, 2016

(86) PCT No.: PCT/US2016/061219
§ 371 (c)(1),
(2) Date: May 8, 2018

(87) PCT Pub. No.: WO2017/083451
PCT Pub. Date: May 18, 2017

(65) Prior Publication Data
US 2018/0273617 A1  Sep. 27, 2018

Related U.S. Application Data

(60) Provisional application No. 62/253,774, filed on Nov. 11, 2015, provisional application No. 62/253,371, filed on Nov. 10, 2015.

(51) Int. Cl.
*C07K 16/00* (2006.01)
*C07K 16/28* (2006.01)
*A61K 47/68* (2017.01)
*G01N 33/574* (2006.01)
*A61K 39/00* (2006.01)

(52) U.S. Cl.
CPC .......... *C07K 16/28* (2013.01); *A61K 47/6803* (2017.08); *A61K 47/6811* (2017.08); *A61K 47/6825* (2017.08); *A61K 47/6831* (2017.08); *A61K 47/6849* (2017.08); *G01N 33/57492* (2013.01); *A61K 2039/505* (2013.01); *C07K 2317/21* (2013.01); *C07K 2317/524* (2013.01); *C07K 2317/56* (2013.01); *C07K 2317/565* (2013.01); *C07K 2317/73* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,673,592 B2 | 3/2014 | Tsuguo et al. | |
| 8,945,870 B2 * | 2/2015 | Shiraishi | C07K 16/30 435/69.1 |
| 2010/0074894 A1 | 3/2010 | Perron | |
| 2011/0135570 A1 | 6/2011 | Janatpour et al. | |
| 2012/0039904 A1 | 2/2012 | Kubota | |
| 2014/0099310 A1 | 4/2014 | Fang et al. | |
| 2016/0194627 A1 | 7/2016 | Smider et al. | |
| 2016/0271231 A1 | 9/2016 | Merchant | |

FOREIGN PATENT DOCUMENTS

| | | |
|---|---|---|
| RU | 2447084 C2 | 4/2012 |
| WO | 2006076734 A2 | 7/2006 |
| WO | 2009058346 A1 | 5/2009 |
| WO | 2013176626 A1 | 11/2013 |
| WO | 2015157595 A1 | 10/2015 |
| WO | 2018089393 A9 | 5/2018 |

OTHER PUBLICATIONS

Bolzoni et al., "Dependence on glutamine uptake and glutamine addiction characterize myeloma cells: A new attractive target," Blood, 2016, 128(5):667-679.
Chen, et al., "Enhancement and Destruction of Antibody Function By Somatic Mutation: Unequal Occurrence Is Controlled By V Gene Combinatorial Associations," EMBO J., 1995, 14(12):2784-2794.
Fathi, et al, "A phase 1 multicenter, open-label, dose-escalation and dose-expansion study to evaluate the safety, tolerability, pharmacokinetics, pharmacodynamics, immunogenicity, and antitumor activity of MEDI7247 in patients with select relapsed/refractory hematologic malignancies," Abstract and corresponding Poster No. TPS2603, American Society of Clinical Oncology Meeting (ASCO), Chicago, Illinois, Jun. 1-5, 2018.
Geldermalsen et al., "ASCT2/SLC1A5 controls glutamine uptake and tumor growth in triple-negative basal-like breast cancer," Oncogene, 2016, 35:3201-3208.

(Continued)

*Primary Examiner* — Meera Natarajan

(57) ABSTRACT

This disclosure provides ASCT2-binding molecules, e.g., anti-ASCT2 antibodies, and antigen-binding fragments thereof. In certain aspects, the ASCT2-binding molecules are conjugated to cytotoxic drugs, e.g., ASCT2 antibody-drug conjugates (ADCs). In certain aspects, the anti-ASCT2 antibodies and fragments thereof can be hybridoma-derived murine monoclonal antibodies, and humanized versions thereof. In certain aspects, the ASCT2-binding molecules bind specifically to cells expressing ASCT2, and in some instances, are internalized into the cells. In addition, this disclosure provides compositions and methods for diagnosing and treating diseases or disorders characterized by ASCT2 overexpression, e.g., certain types of cancer. In a particular embodiment, the disclosure provides methods for treating cancer using ASCT2 ADCs.

20 Claims, 18 Drawing Sheets

Specification includes a Sequence Listing.

(56) References Cited

OTHER PUBLICATIONS

Monks, et al, "MEDI7247, A Novel Pyrrolobenzodiazepine ADC Targeting ASCT2 With Potent In Vivo Activity Across A Spectrum of Hematological Malignancies," Abstract and corresponding Poster LB-295, 2018 Annual Meeting of the Amercican Association for Cancer Research (AACR), Chicago, Illinois, Apr. 17, 2018.

Pakula, "Genetic Analysis of Protein Stability and Function," Annu. Rev., Genet., 1989, 23:289-310.

Pore, et al., "Discovery and Development of MEDI7247, a Novel Pyrrolobenzodiazepine (PBD)-Based Antibody Drug Conjugate Targeting ASCT2, For Treating Hematological Cancers," Blood, Published Online Nov. 21, 2018, 132:4071.

Pore, et al., "Discovery and Development of MEDI7247, a Novel Pyrrolobenzodiazepine (PBD)-Based Antibody Drug Conjugate Targeting ASCT2, For Treating Hematological Cancers," Abstract and corresponding Poster, American Society of Hematology Annual Meeting (ASH), San Diego, California, Dec. 1-4, 2018.

Pore, et al., "Discovery and Development of MEDI7247, a Novel Pyrrolobenzodiazepine (PBD)-Based Antibody Drug Conjugate Targeting ASCT2, For Treating Hematological and Solid Cancers," Abstract and corresponding Poster LB-296, 2018 Annual Meeting of the Amercican Association for Cancer Research (AACR), Chicago, Illinois, Apr. 17, 2018.

Roitt, et al., "Immunology (Fifth Edition)," 2000, 63-64 and 110-111.

Rudikoff, et al., "Single Amino Acid Substitution Altering Antigen-Binding Specificity," Proc., Natl. Acad. Sci., 1982, 79:1979-1983.

Schifferli, et al., "MEDI7247: A First in Class Antibody Drug Conjugate Targeting ASCT2 in a Range of Solid Tumors," Abstract and corresponding Poster LB-298, 2018 Annual Meeting of the Amercican Association for Cancer Research (AACR), Chicago, Illinois, Apr. 17, 2018.

International Search Report dated Feb. 6, 2017, Written Opinion dated Feb. 6, 2017, and International Preliminary Report on Patentability dated May 15, 2018 for International Application PCT/US2016/061219.

International Search Report dated Apr. 6, 2018, Written Opinion dated Apr. 6, 2018, and International Preliminary Report on Patentability dated May 14, 2019 for International Application PCT/US2017/060489.

U.S. Appl. No. 16/346,612, filed May 1, 2019.

\* cited by examiner

----- Control
——— ASCT2

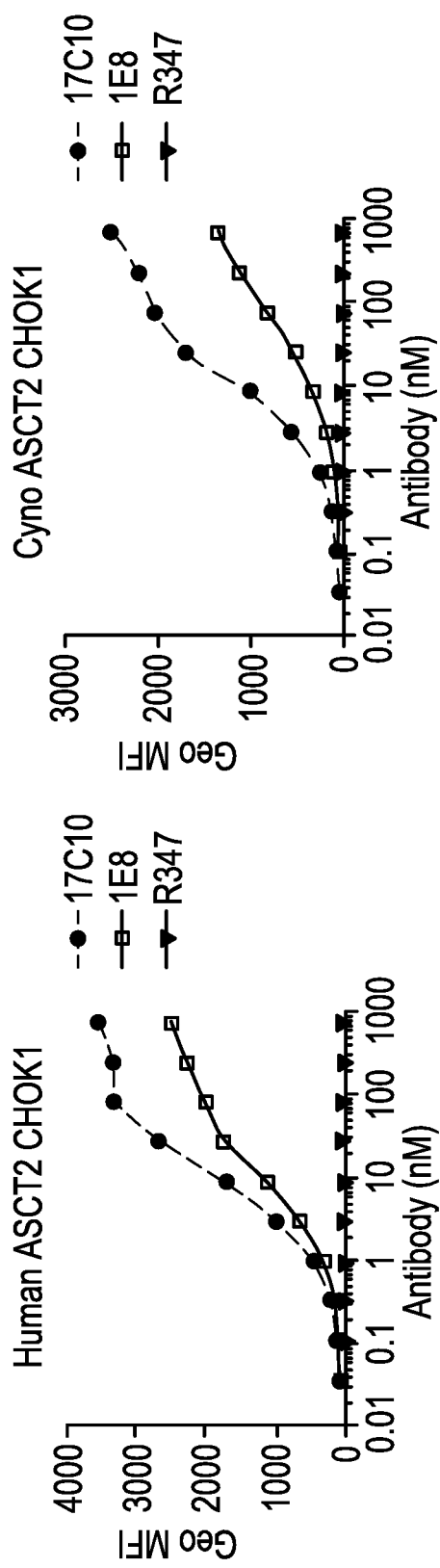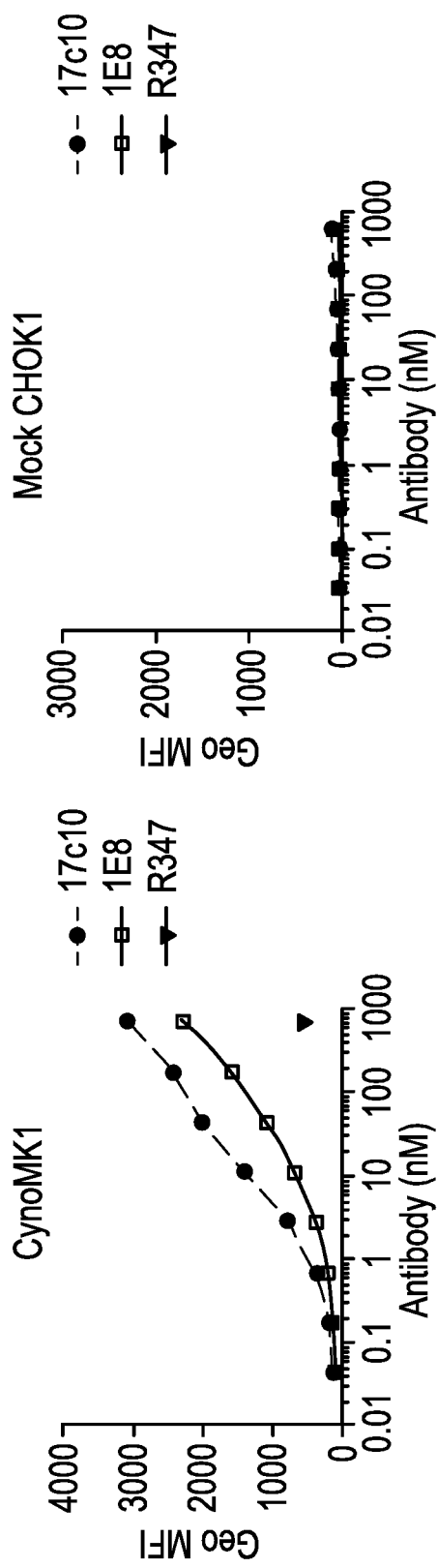

SKMEL-2

-●- NT shRNA/17C10-ADC
-♦- NT shRNA/Isotype-ADC
-☆- ASCT1-ShRNA(1)/17C10-ADC
⋯★⋯ ASCT1-shRNA(2)/17C10-ADC
-□- ASCT2-shRNA/17C10-ADC HuASCT2_CHOK1

CynoASCT2_CHOK1

WiDr

Mock_CHOK1

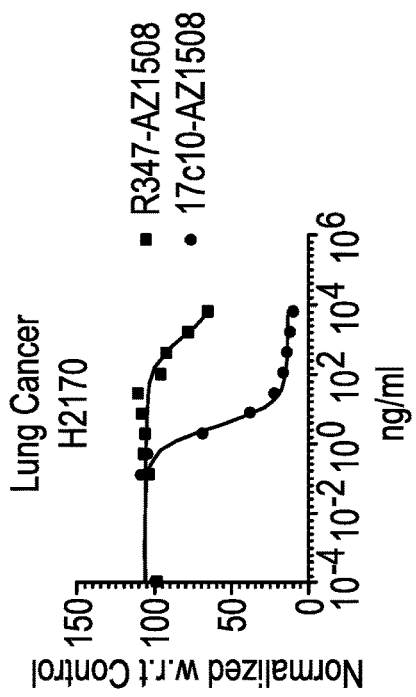
FIG. 10A Pancreatic Cancer BxPC3
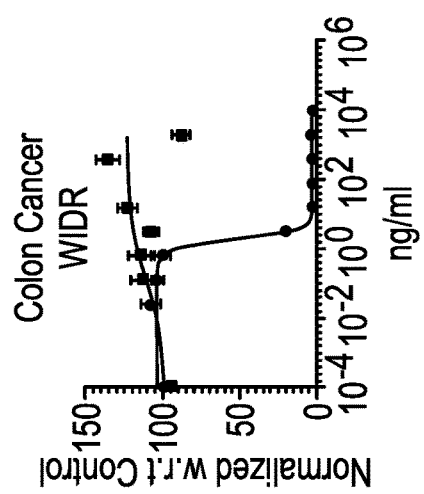
FIG. 10B Colon Cancer WIDR
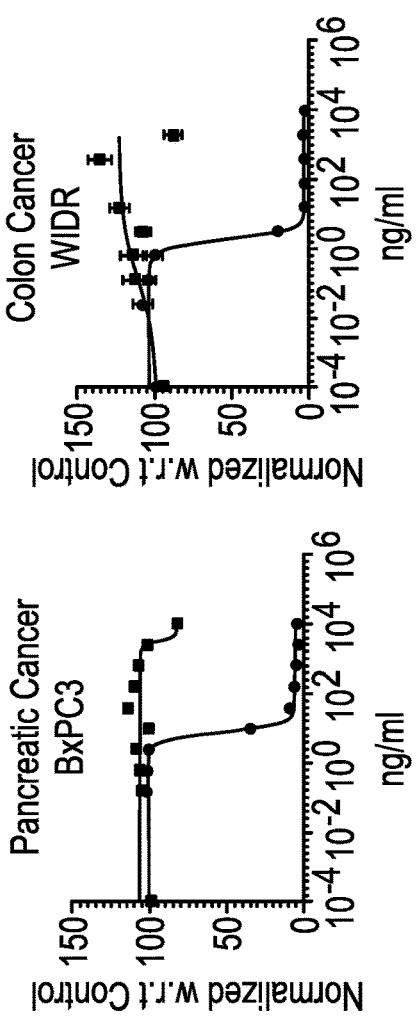
FIG. 10C Lung Cancer H2170
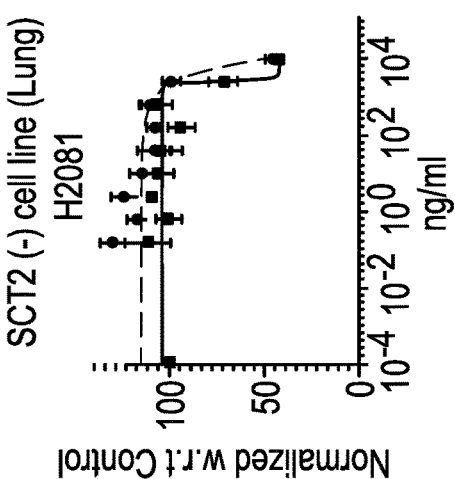
FIG. 10D HNSCC OE21
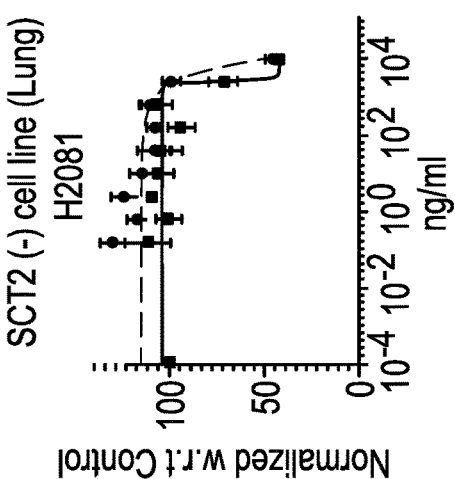
FIG. 10E Prostate Cancer 22RV1
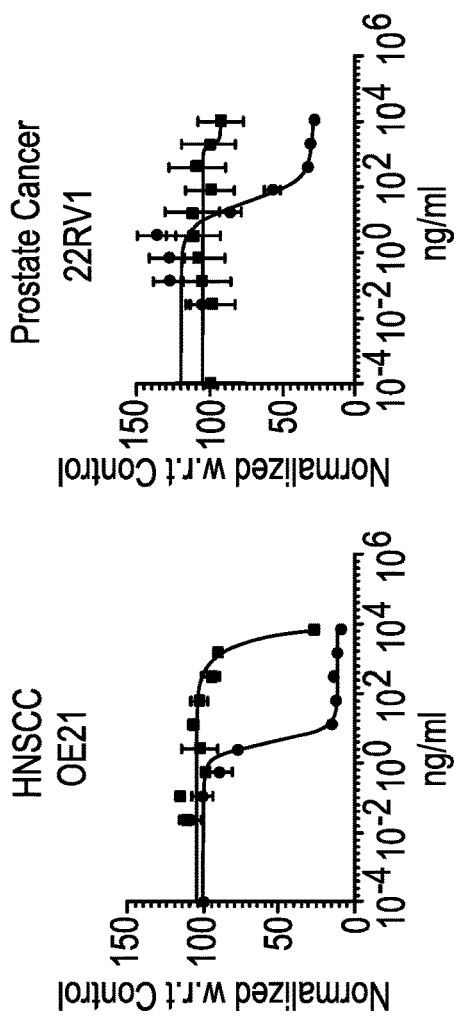
FIG. 10F SCT2 (−) cell line (Lung) H2081

BINDING MOLECULES SPECIFIC FOR ASCT2 AND USES THEREOF

CROSS-REFERENCE TO RELATED APPLICATIONS

This application is a U.S. National Stage application of International Application No. PCT/US2016/061219, filed on Nov. 10, 2016, said International Application No. PCT/US2016/061219 claims benefit under 35 U.S.C. § 119(e) of the U.S. Provisional Application No. 62,253,371, filed Nov. 10, 2015, and 62/253,774, filed Nov. 11, 2015. Each of the above listed applications is incorporated by reference herein in its entirety for all purposes.

BACKGROUND

The solute carrier (SLC) family includes more than 300 genes encoding membrane transport proteins, organized into dozens of sub-families. The SLC1A sub-family includes transport system ASC, which mediates sodium-dependent neutral amino acid transport in vertebrate cells. Alanine; Serine; and Cysteine are the preferred substrates of the ASC system. Two sub-types of the ASC system have been identified, ASC transporter 1 (ASCT1, also known as SLC1A4) and ASC transporter 2 (ASCT2, also known as SLC1A5).

ASCT2 is a 541-amino-acid, multi-pass membrane protein with eight transmembrane domains. The molecular weight of ASCT2 varies from 55-75 KD depending on the various glycosylation profiles. In addition to transporting L-alanine, L-serine, and L-cysteine, ASCT2 also transports L-threonine and L-glutamine. Furthermore, ASCT2 functions as a cell surface receptor which is shared by type D simian retro virus and type C viruses.

Overexpression of ASCT2 has been reported in various cancers, including colorectal cancer, head and neck squamous cell carcinoma (HNSCC), prostate cancer, lung cancer, pancreatic cancer, and hematological cancers such as myeloma and lymphoma. Overexpression of ASCT2, evaluated by immuno-histochemical analyses (IHC), shows poor prognosis in various cancers including colorectal cancer, prostate cancer, lung cancer, and pancreatic cancer (K Kaira, et al. (2015) Histopathology; Shimizu, et al. (2014) BJC; D Witte, et al. (2002) Anticancer Research; R Li, et al. (2003) Anticancer Research). It has been reported that ASCT2 is one driver of the mammalian target of rapamycin (mTOR) signaling pathway, and consequently, of tumor growth (Nicklin P. et al. (2009) Cell).

Antibody-drug conjugates (ADCs) represent a promising new therapeutic approach to more effectively treat cancer while reducing drug-related toxicities by combining the specificity of an antibody with the potency of cytotoxic small molecules or toxins. An ADC may comprise a cytotoxin, which may be a small molecule that has been chemically modified to contain a linker. The linker is then used to conjugate the cytotoxin to the antibody or antigen-binding fragment thereof. Cytotoxicity is induced when the ADC binds to the antigen surface of a target-positive cell, is internalized and trafficked to the lysosome where the cytotoxin is released following either proteolysis of a cleavable linker (for example by cathepsin B found in the lysosome) or through proteolytic degradation of the antibody when a non-cleavable linker is used to attach the cytotoxin to the antibody. The cytotoxin then translocates out of the lysosome and into the cytosol where it can then bind to its target, depending on its mechanism of action. Typically these cytotoxins induce cell cycle arrest which subsequently leads to apoptosis. Corresponding conjugates containing imaging agents also represent a promising new way to detect cancer cells in vivo or in vitro.

This disclosure provides molecules that specifically bind to ASCT2, and methods for the use of such molecules, e.g., for detection of ASCT2, for delivery of a heterologous agent to a cell, or for the treatment of a disease or disorder characterized by ASCT2 overexpression, e.g., cancer. This disclosure provides anti-ASCT2 antibodies conjugated to a cytotoxic drug such as a tubulysin derivative or a pyrrolobenzodiazepine (anti-ASCT2-ADCs). The antibodies of the invention are useful for the treatment of a disease or disorder characterized by ASCT2 overexpression, e.g., cancer. For instance, the inventors have shown that anti-ASCT2 ADCs cause tumor regression in xenogenic mouse models of human colorectal and head and neck cancers.

BRIEF SUMMARY OF THE INVENTION

Some of the main aspects of the present invention are summarized below. Additional aspects are described in the Detailed Description of the Invention, Examples, Drawings, and Claims sections of this disclosure. The description in each section of this disclosure is intended to be read in conjunction with the other sections. Furthermore, the various embodiments described in each section of this disclosure can be combined in various different ways, and all such combinations are intended to fall within the scope of the present invention.

The disclosure provides ASCT2-binding molecules, e.g., anti-ASCT2 antibodies or antigen-binding fragments thereof, e.g., monoclonal antibodies capable of binding to ASCT2. In some aspects, the binding molecule is conjugated to an agent, such as a cytotoxin.

In some instances, an isolated binding molecule or antigen-binding fragment thereof, which specifically binds to an epitope of ASCT2, specifically binds to the same ASCT2 epitope as an antibody or antigen-binding fragment thereof that comprises the heavy chain variable region (VH) and light chain variable region (VL) of 17c10 or 1e8.

In some instances, the VH of 17c10 comprises SEQ ID NO: 1 or SEQ ID NO: 5, and the VL of 17c10 comprises SEQ ID NO: 2 or SEQ ID NO: 6.

In some instances, the VH of 1e8 comprises SEQ ID NO: 3 or SEQ ID NO: 7, and the VL of 1e8 comprises SEQ ID NO: 4 or SEQ ID NO: 8.

In some instances, an isolated binding molecule or antigen-binding fragment thereof, which specifically binds to ASCT2, comprises an antibody VL, wherein the VL comprises an amino acid sequence at least 85%, 90%, 95%, or 100%/o identical to a reference amino acid sequence selected from the group consisting of SEQ ID NO: 2, SEQ ID NO: 4, SEQ ID NO: 6 and SEQ ID NO: 8.

In some instances, an isolated binding molecule or antigen-binding fragment thereof, which specifically binds to ASCT2, comprises an antibody VH, wherein the VH comprises an amino acid sequence at least 85%, 90%, 95%, or 100%/o identical to a reference amino acid sequence selected from the group consisting of SEQ ID NO: 1, SEQ ID NO: 3, SEQ ID NO: 5, and SEQ ID NO: 7.

In some instances, an isolated binding molecule or antigen-binding fragment thereof, which specifically binds to ASCT2, is conjugated to an agent selected from the group consisting of an antimicrobial agent, a therapeutic agent, a prodrug, a peptide, a protein, an enzyme, a lipid, a biological response modifier, a pharmaceutical agent, a lymphokine, a heterologous antibody or fragment thereof, a detectable label, a polyethylene glycol (PEG), and a combination of two or more of any said agents.

In some instances, an isolated binding molecule or antigen-binding fragment thereof, which specifically binds to ASCT2, is conjugated to a cytotoxin. In certain embodiments, the cytotoxin is selected from the group consisting of AZ1508, SG3249, and SG3315.

In some instances, the binding molecule or fragment thereof comprises an antibody or antigen-binding fragment thereof.

In some instances, an isolated antibody or antigen-binding fragment thereof, which specifically binds to ASCT2, comprises a VH and a VL, wherein the VH and VL comprise, respectively, amino acid sequences at least 85%, 90%, 95%, or 100% identical to reference amino acid sequences selected from the group consisting of SEQ ID NO: 1 and SEQ ID NO: 2, SEQ ID NO: 3 and SEQ ID NO: 4; SEQ ID NO: 5 and SEQ ID NO: 6; and SEQ ID NO: 7 and SEQ ID NO: 8. In some instances, the VH comprises the amino acid sequence SEQ ID NO: 5 and the VL comprises the amino acid sequence SEQ ID NO: 6. In some instances, the VH comprises the amino acid sequence SEQ ID NO: 7 and the VL comprises the amino acid sequence SEQ ID NO: 8.

In some instances, the antibody or antigen-binding fragment thereof comprises a heavy chain constant region or fragment thereof. In some instances, the heavy chain constant region or fragment thereof is an IgG constant region. In some instances, the IgG constant region comprises the amino acid sequence SEQ ID NO: 9. In some instances, the IgG constant region is a human IgG1 constant domain.

In some instances, the antibody or antigen-binding fragment thereof comprises a light chain constant region selected from the group consisting of a human kappa constant region and a human lambda constant region.

In some instances, the antibody or antigen-binding fragment thereof is a murine antibody, a humanized antibody, a chimeric antibody, a monoclonal antibody, a polyclonal antibody, a recombinant antibody, a multispecific antibody, or an antigen-binding fragment thereof. In some instances, the antigen-binding fragment is Fv, Fab, F(ab')2, Fab', dsFv, scFv, and sc(Fv)2.

In some instances, the antibody or antigen-binding fragment thereof can bind to human ASCT2 and cynomolgus (cyno) monkey ASCT2.

In some instances, the antibody or antigen-binding fragment thereof does not specifically bind to human ASCT1.

In some instances, the antibody or antigen-binding fragment thereof is conjugated to an agent selected from the group consisting of an antimicrobial agent, a therapeutic agent, a prodrug, a peptide, a protein, an enzyme, a lipid, a biological response modifier, a pharmaceutical agent, a lymphokine, a heterologous antibody or fragment thereof, a detectable label, a PEG, and a combination of two or more of any said agents.

In some instances, the antibody or antigen-binding fragment thereof is conjugated to a cytotoxin. In certain embodiments, the cytotoxin is selected from the group consisting of AZ1508, SG3249, and SG3315.

In some instances, the invention provides an isolated polynucleotide or combination of polynucleotides comprising a nucleic acid encoding a binding molecule or fragment thereof as described herein. In some instances, the invention provides an isolated polynucleotide or combination of polynucleotides comprising a nucleic acid encoding an antibody or antigen-binding fragment thereof as described herein.

In some instances, the invention provides a vector comprising a polynucleotide described herein. In some instances, a polynucleotide comprising a nucleic acid encoding a VH and a polynucleotide comprising a nucleic acid encoding a VL are in the same vector. In some instances, a polynucleotide comprising a nucleic acid encoding a VH and a polynucleotide comprising a nucleic acid encoding a VL are in different vectors.

In some instances, the invention provides a composition comprising (i) a binding molecule or fragment thereof as described herein, and (ii) a carrier. In some instances, the invention provides a composition comprising (i) an antibody or antigen-binding fragment thereof as described herein, and (ii) a carrier. In some instances, the invention provides a composition comprising (i) a nucleic acid encoding an antibody or antigen-binding fragment thereof as described herein, and (ii) a carrier. In some instances, the invention provides a composition comprising (i) a vector as described herein, and (ii) a carrier. In some aspects, the carrier is a pharmaceutically acceptable carrier.

In some instances, the invention provides a host cell comprising a polynucleotide as described herein, a vector as described herein, or a composition as described herein.

In some instances, the invention provides a method of making a binding molecule or fragment as described herein, the method comprising (a) culturing a host cell as described herein; and (b) isolating the binding molecule or fragment. In some instances, the invention provides a method of making an antibody or antigen-binding fragment as described herein, the method comprising (a) culturing a host cell as described herein; and (b) isolating the antibody or antigen-binding fragment.

In some instances, the invention provides a diagnostic reagent or a kit comprising a binding molecule or fragment thereof as described herein, or an antibody or antigen-binding fragment thereof as described herein.

In some instances, a method of delivering an agent to an ASCT2-expressing cell comprises contacting the cell with a binding molecule or fragment conjugated to an agent, as described herein, or an antibody or antigen-binding fragment thereof conjugated to an agent, as described herein, wherein the agent is internalized by the cell. In some instances, the agent can be selected from the group consisting of an antimicrobial agent, a therapeutic agent, a prodrug, a peptide, a protein, an enzyme, a lipid, a biological response modifier, a pharmaceutical agent, a lymphokine, a heterologous antibody or fragment thereof, a detectable label, a PEG, and a combination of two or more of any said agents. In some instances, the agent can be a cytotoxin.

In some instances, a method of inducing death in an ASCT2-expressing cell comprises contacting the cell with a binding molecule or fragment conjugated to a cytotoxin, as described herein, or an antibody or antigen-binding fragment thereof conjugated to a cytotoxin, as described herein, wherein the cytotoxin is internalized by the cell. In one preferred embodiment, the cytotoxin is selected from the group consisting of AZ1508, SG3249, and SG3315.

In some instances, a method of treating a disease or disorder characterized by ASCT2 overexpression, e.g., cancer, in a subject comprises administering to a subject in need of treatment an effective amount of a binding molecule or fragment as described herein, or an antibody or antigen-binding fragment as described herein, or a composition as described herein.

In some instances, a method of treating a disease or disorder characterized by ASCT2 overexpression, e.g., cancer, includes a broad range of cancers spanning from solid tumors to hematological tumors. Such a broad range of effectiveness for methods of treatment are not common, but are rather unexpected. In addition to the broad range of effect demonstrated across solid and hematological tumors, the invention described herein can also be used in methods of determining the presence of cancer stem cells (CSC) and methods of treatment involving CSCs, which further supports the breadth of use and unexpected effect of the invention described herein.

In some instances, the cancer is selected from the group consisting of colorectal cancer, HNSCC, prostate cancer, lung cancer, pancreatic cancer, melanoma, endometrial cancer, and hematological cancer (acute myeloid leukemia (AML), multiple myeloma (MM), diffuse large B-cell lymphoma (DLBCL)). In addition, methods comprise treatments comprising targeting CSCs. Preferably, the subject is a human subject.

In some instances, a method for detecting ASCT2 expression level in a sample comprises (a) contacting said sample with of a binding molecule or fragment as described herein, or an antibody or antigen-binding fragment as described herein, or a composition as described herein, and (b) detecting binding of the binding molecule or fragment thereof, or the antibody or antigen-binding fragment thereof, to ASCT2 in said sample. In some instances, the sample is a cell culture. In some instances, the sample is an isolated tissue. In some instances, the sample is from a subject, preferably a human subject.

BRIEF DESCRIPTION OF THE DRAWINGS/FIGURES

Figure 1A:
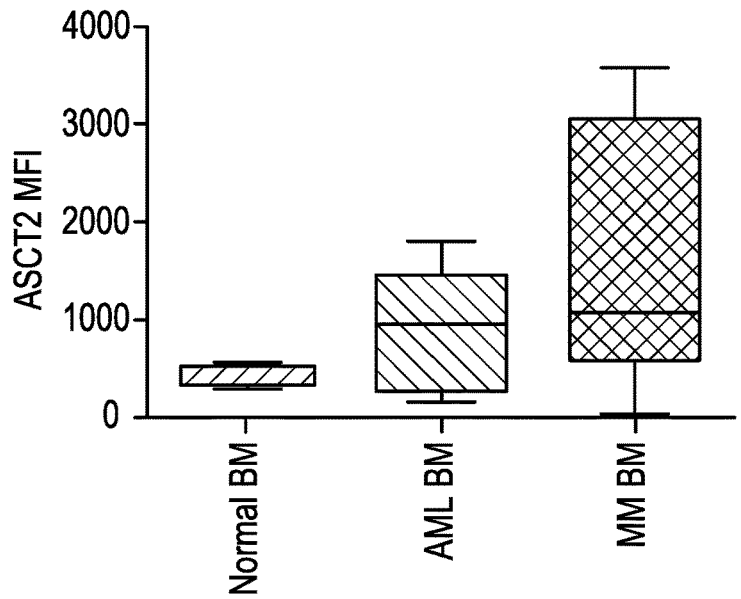
FIG. 1A shows quantification of flow cytometry analyses demonstrating high ASCT2 expression in the bone marrow aspirates from AML and MM samples in comparison to bone marrow from healthy samples.
Figure 1B:
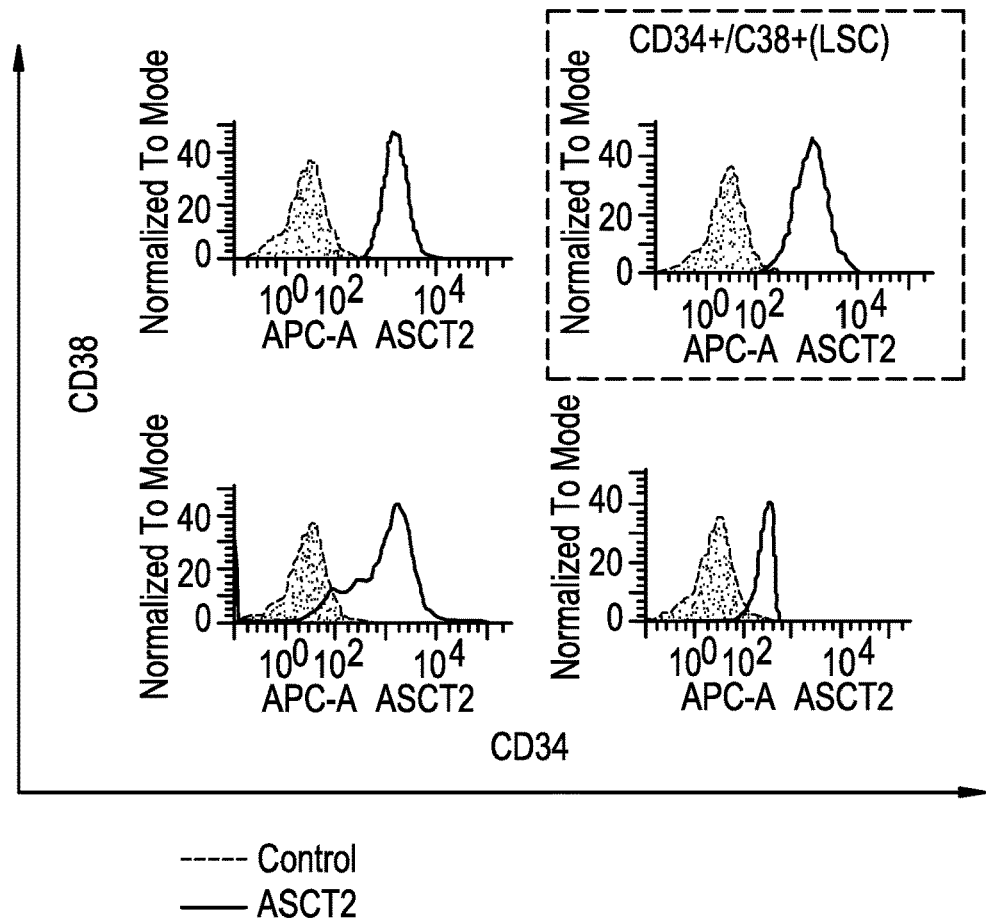
FIG. 1B shows high expression of ASCT2 in CD34+/CD38+ population, reported markers defining leukemic stem cell population (LSC). Additionally expression of ASCT2 was evaluated in all other subtypes such as CD34+CD38−, CD34+CD38+ and CD34−CD38+ populations.
Figure 1C:
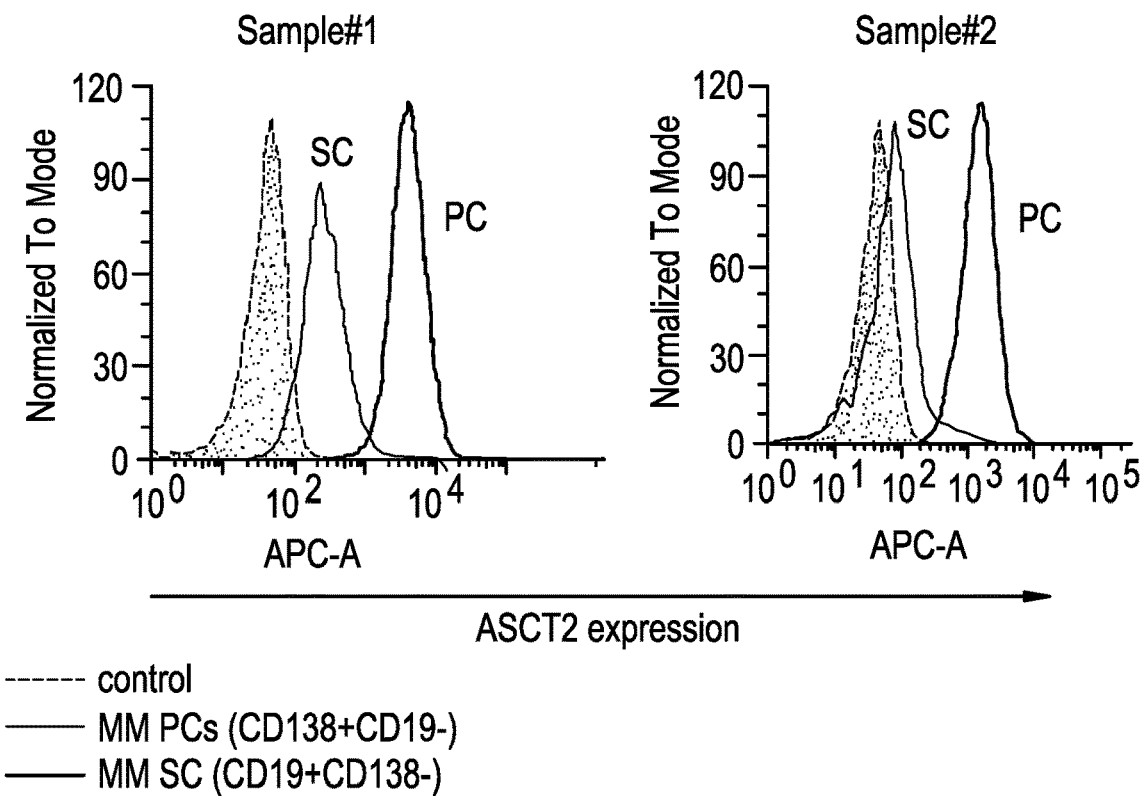

FIG. 1C shows ASCT2 expression in plasma cells (PC; CD138+/CD19−) and stem cells (SC; CD138−/CD19+) from MM samples.

Figure 1D:
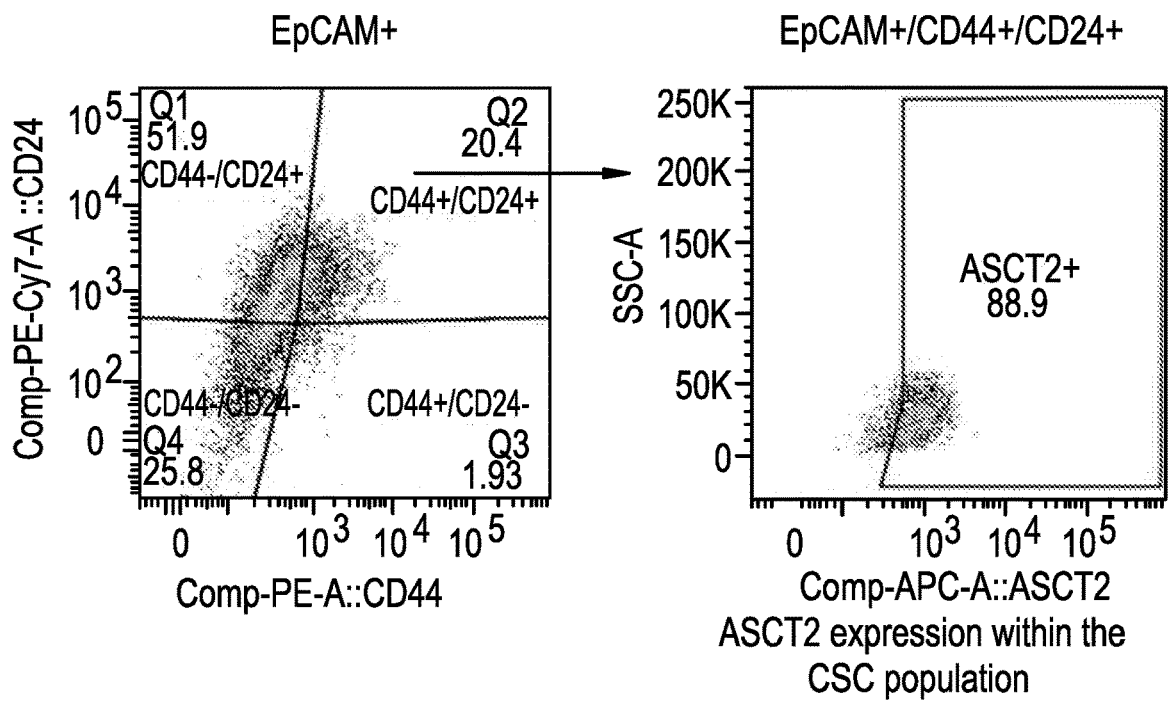

FIG. 1D shows ASCT2 expression evaluated in an EpCAM+/CD24+/CD44+ cell population, reported markers for pancreatic CSCs. Flow cytometry analyses suggests high ASCT2 expression of CSCs in pancreatic tumors.

Figure 1E:
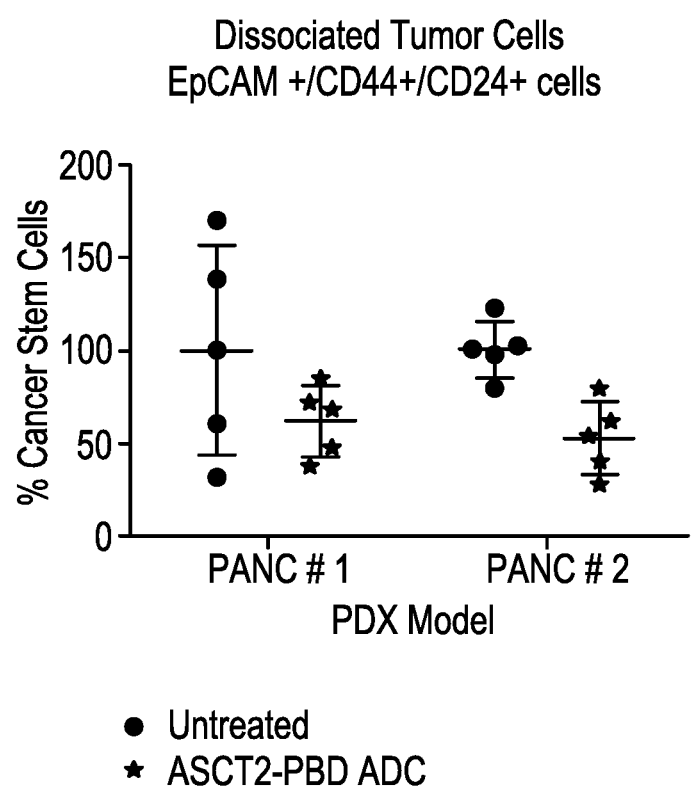

FIG. 1E shows ablation of CSCs (EpCAM+/CD24+/CD44+) population in pancreatic tumors following treatment with an ASCT2-PBD ADC (antibody 17c10 is conjugated to SG3249) in vivo.

Figure 2:
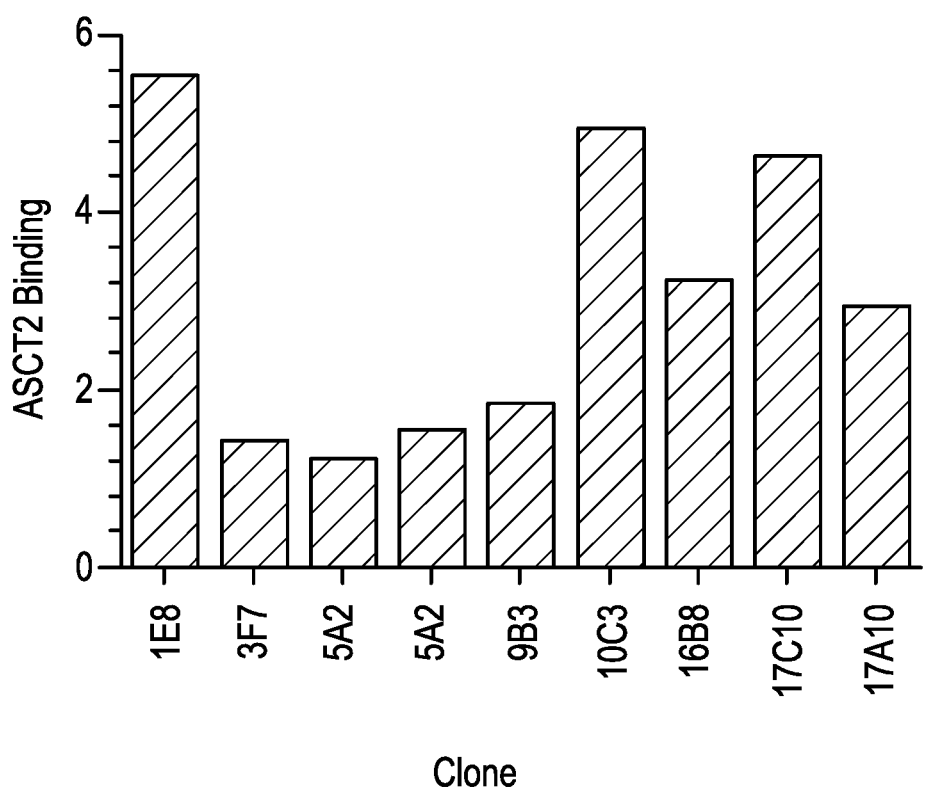

FIG. 2 shows a graph depicting the fold change in binding activity of purified human anti-ASCT2 IgGs 1e8, 3f7, 5a2, 9b3, 10c3, 16b8, 17c10, and 17a10 to 293F cells transfected with a plasmid expressing human ASCT2.

Figure 3A:
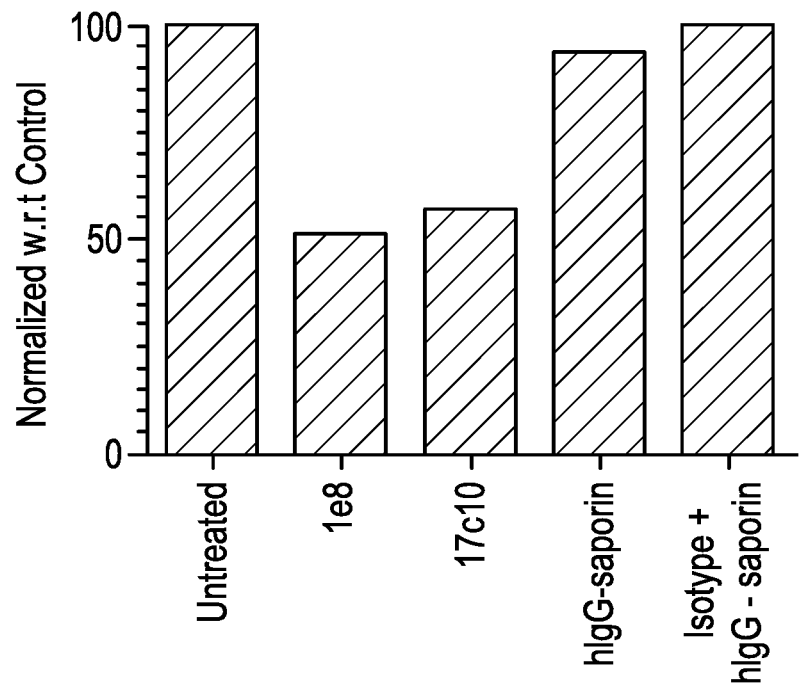

FIG. 3A shows a bar graph of the relative viability to that of untreated control cells of 293F cells expressing ASCT2 treated with negative control (untreated); treated with primary anti-ASCT2 antibodies 1e8 and 17c10; treated with an anti-ASCT2 antibody conjugated to saporin; or treated with a control antibody linked to saporin (hIgG-saporin).

Figure 3B:
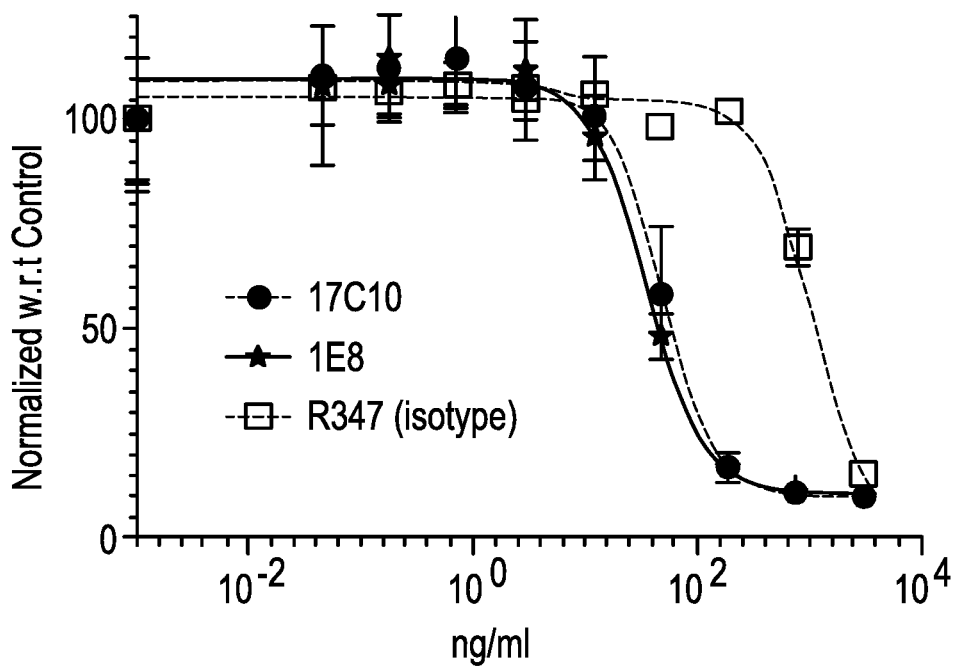

FIG. 3B shows a graph of the cytotoxicity of anti-ASCT2 1 E8, anti-ASCT2 17C10, and isotype control R347 classically conjugated to tubulysin AZ1508 in Sw48 cells.

Figure 4:
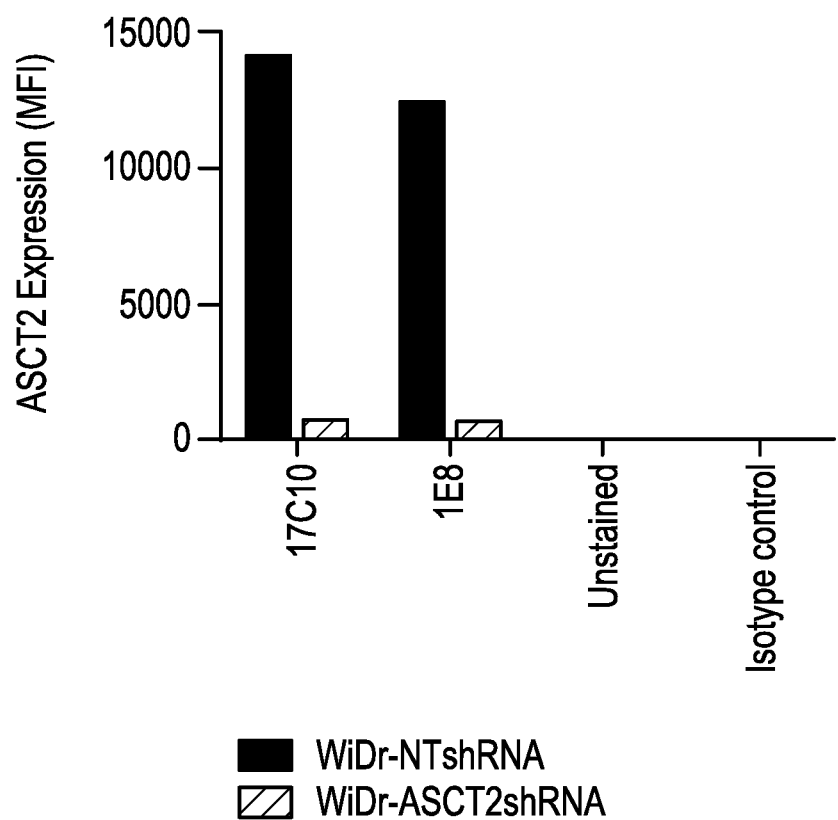

FIG. 4 shows a bar graph depicting binding of anti-ASCT2 antibodies 17c10 and 1e8 to WiDr cells or WiDr cells with an shRNA knockdown of ASCT2 expression, as assessed by flow cytometry.

Figure 5A:
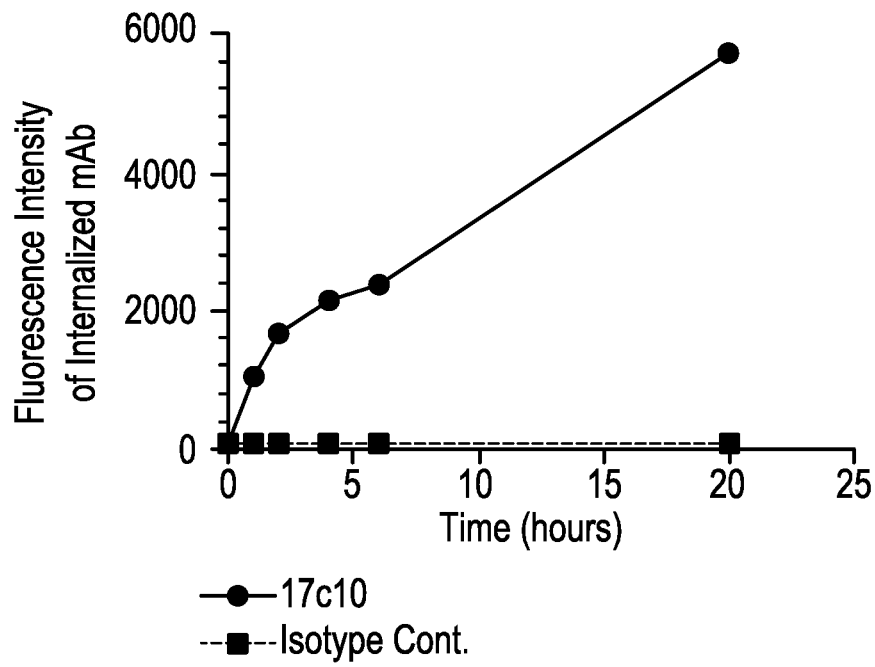

FIG. 5A shows the internalization kinetics of anti-ASCT2 antibody 17c10 and an isotype control.

Figure 5B:
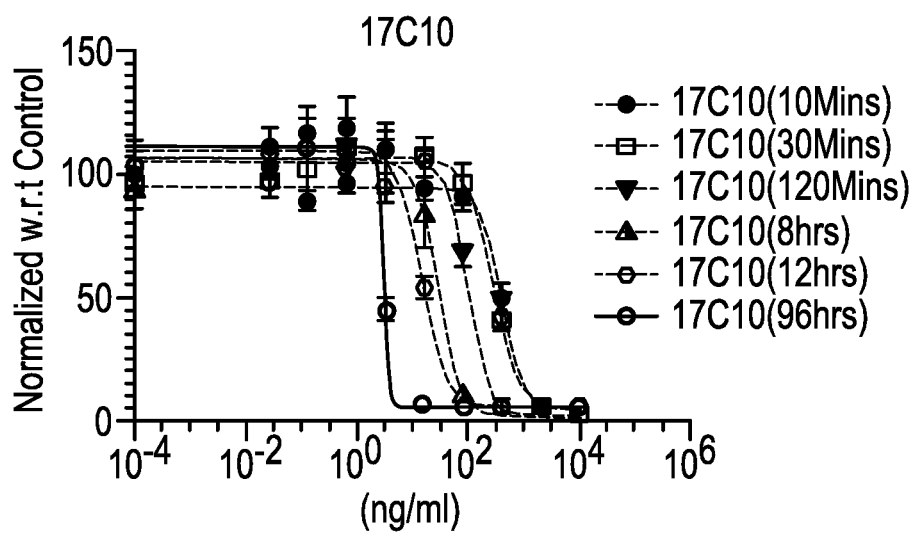

FIG. 5B. shows internalization kinetics of ASCT2-ADC (antibody 17c10 conjugated to AZ1508) as measured by cytotoxic killing. Cells were pulsed with ASCT2-ADC (17c10-AZ1508) for respective time periods. Thereafter, ADC containing medium was replaced with fresh medium and further incubated for 4 days. Cell viability was measured by using CTG Kit. Dose-response curves were plotted as a percentage of untreated control cells.

Figure 6A:
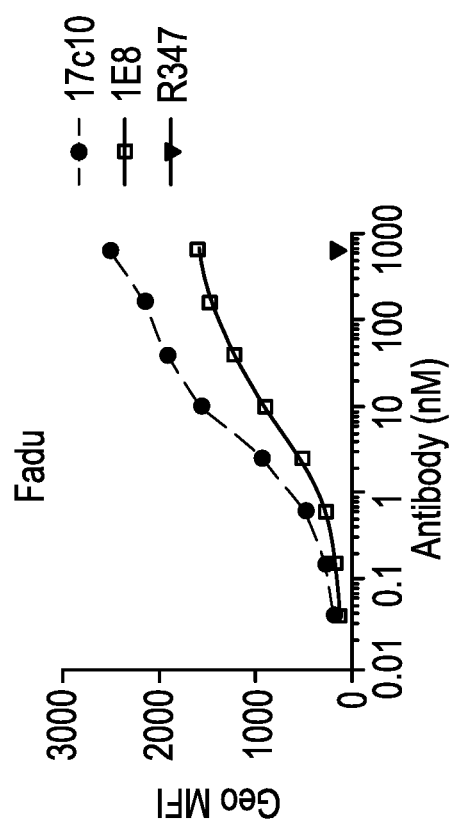
Figure 6B:
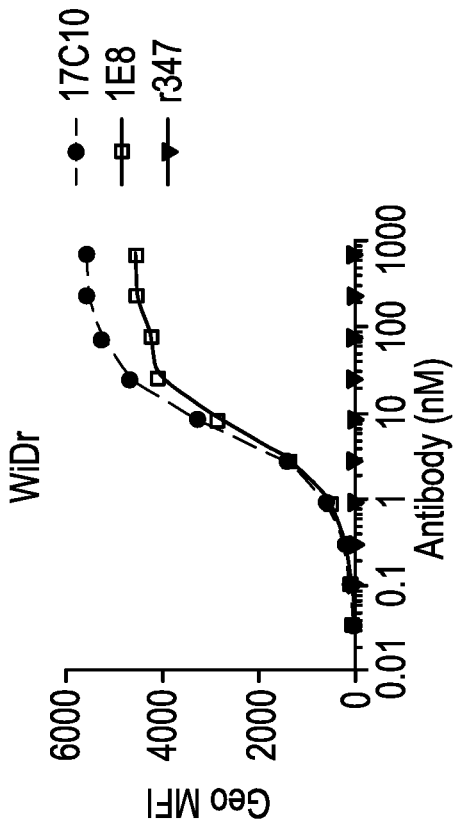
Figure 6C:
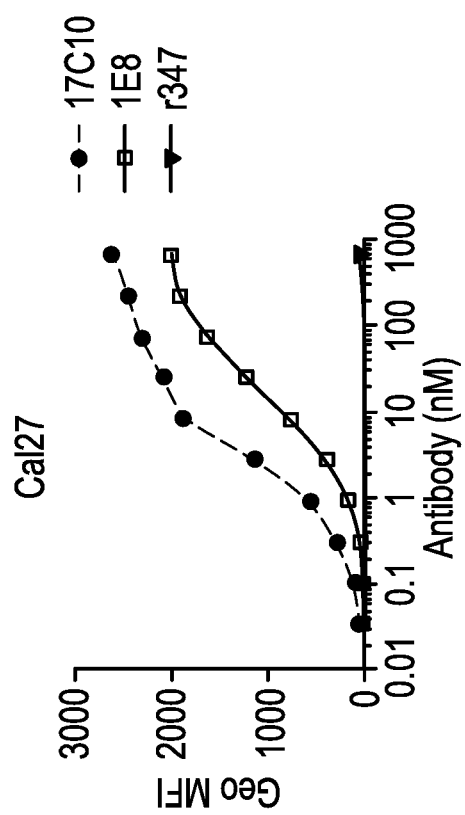
Figure 6D:
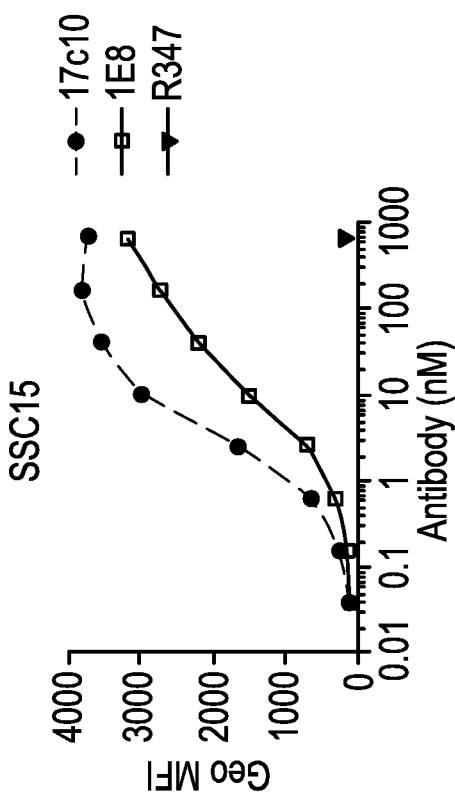

FIG. 6A to FIG. 6H show flow cytometry plots resulting from binding of anti-ASCT2 antibodies 17c10 and 1e8, and isotype control R347, to ASCT2-expressing cell lines. FIG. 6A, human cancer cell line Ca127; FIG. 6B, human cancer cell line FaDu; FIG. 6C human cancer cell line SSC15; FIG. 6D human cancer cell line WiDr; FIG. 6E CHOK1 cells stably expressing human ASCT2; FIG. 6F CHOK1 cells stably expressing cyno ASCT2; FIG. 6G cyno cancer cell line CynoMK1; and FIG. 6H mock transfected CHOK1 cells.

Figure 7A:
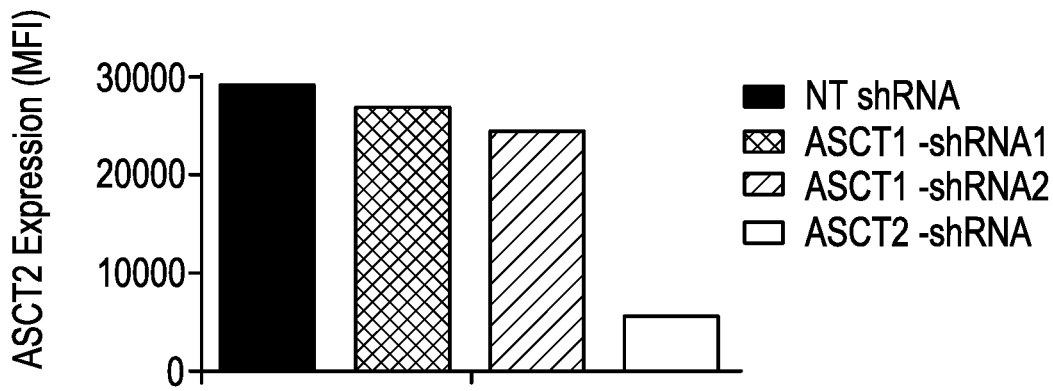

FIG. 7A shows binding of anti-ASCT2 antibody 17c10 to SKMEL-2 cells were not altered by ASCT1 shRNAs, while the binding was significantly reduced following the ASCT2 specific shRNA knock down.

Figure 7B:
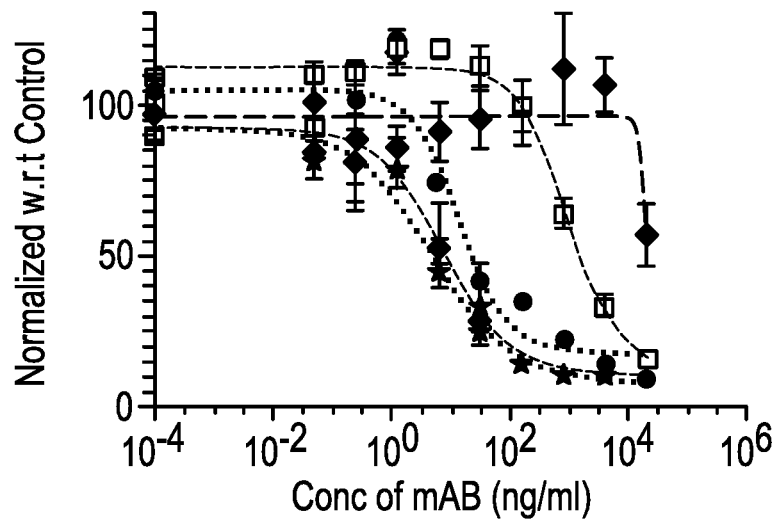

FIG. 7B shows cytotoxic killing of anti-ASCT2 antibody ADC (antibody 17c10 conjugated to AZ1508) was unaffected following ASCT1 shRNA knock down, while significant reduction of cytotoxic killing was observed following ASCT2 shRNA silencing. Data from all the shRNA knockdown groups were normalized with respect to untreated controls.

Figure 8A:
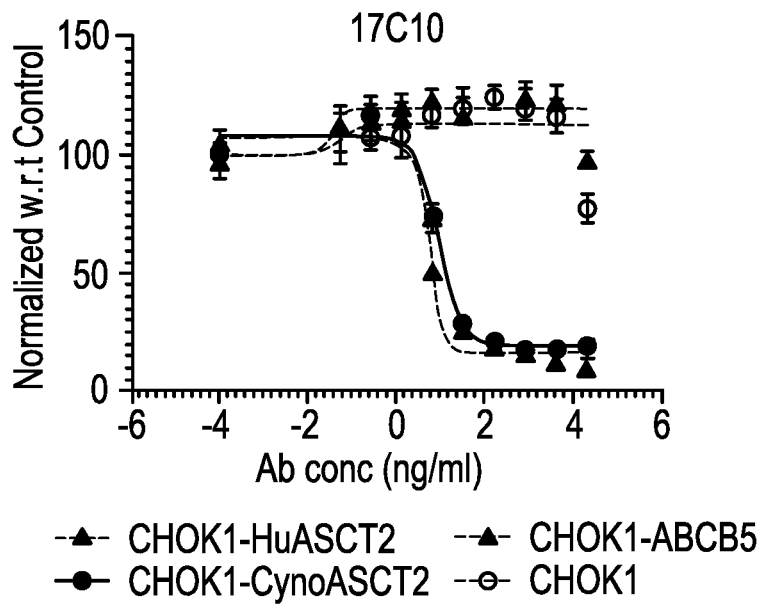
Figure 8B:
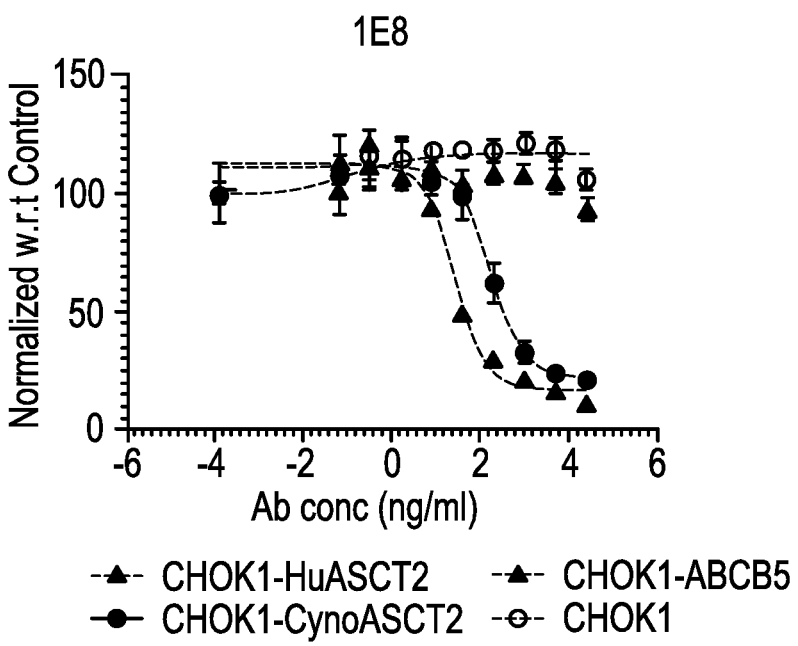

FIG. 8A and FIG. 8B show the cytotoxic effects of anti-ASCT2 antibodies 17c10 (FIG. 8A) and 1e8 (FIG. 8B), conjugated to tubulysin 1508 against stable CHO-K1 cell lines expressing human or cyno ASCT2 proteins or an irrelevant receptor.

Figure 9A:
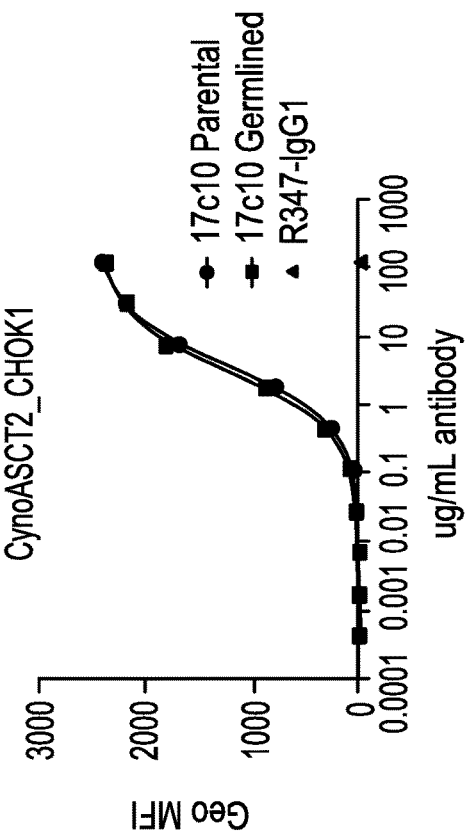
Figure 9B:
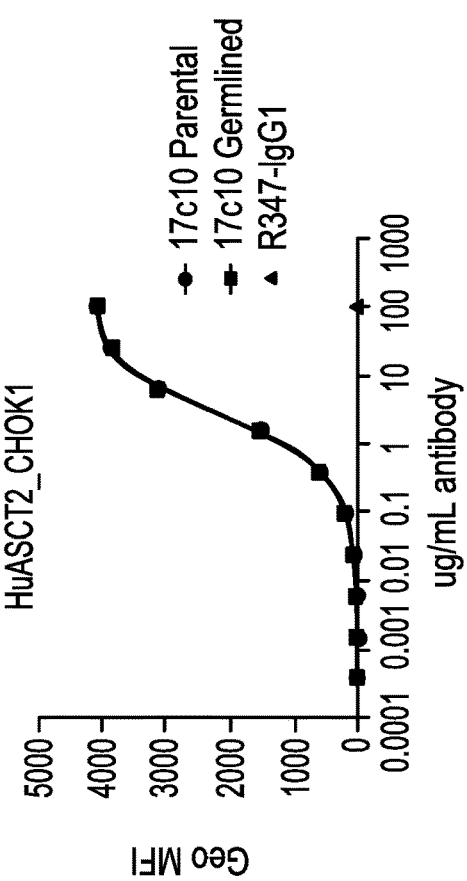
Figure 9C:
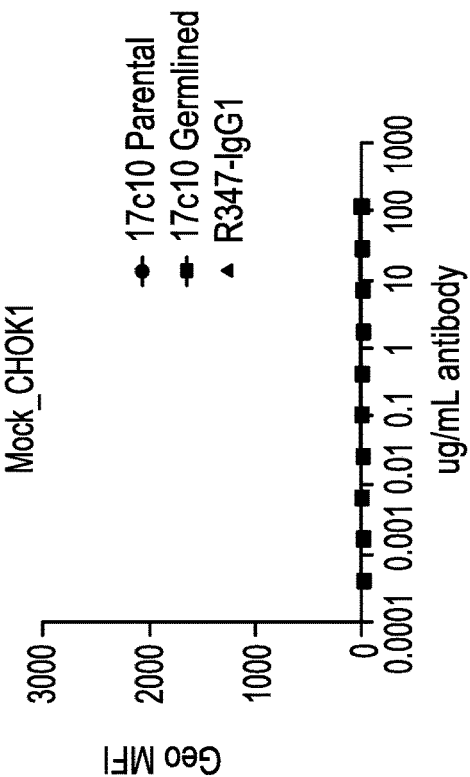
Figure 9D:
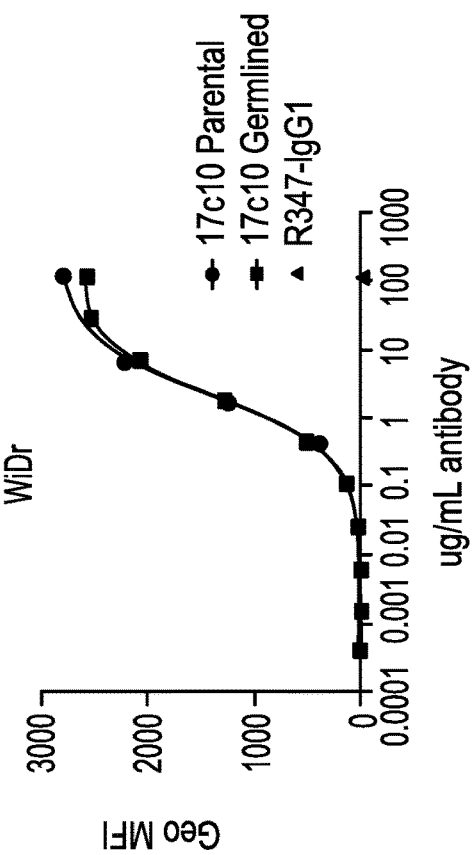

FIG. 9A to FIG. 9D show flow cytometry plots for binding of 17c10 parental antibody, 17c10 germlined antibody, and R347 isotype control antibody to stable CHO-K1 cell lines expressing human ASCT2 (FIG. 9A); stable CHO-K1 cell lines expressing cyano ASCT2 (FIG. 9B); colorectal cancer cells WiDr expressing ASCT2 (FIG. 9C); and mock transfected control cells (FIG. 9D).

FIG. 10A to FIG. 10F shows the relative viability (%) normalized to that of untreated control cells of cancer cell lines treated with anti-ASCT2 antibody 17c10 conjugated to tubulysin AZ1508 and R347 isotype control antibody conjugated to tubulysin AZ1508 to pancreatic cancer cells (FIG. 10A), colon cancer cells (FIG. 10B), lung cancer cells (FIG. 10C), HNSCC cancer cells (FIG. 10D), prostate cancer cells (FIG. 10E), and a non-ASCT2-expressing cell line (FIG. 10F).

Figure 11A:
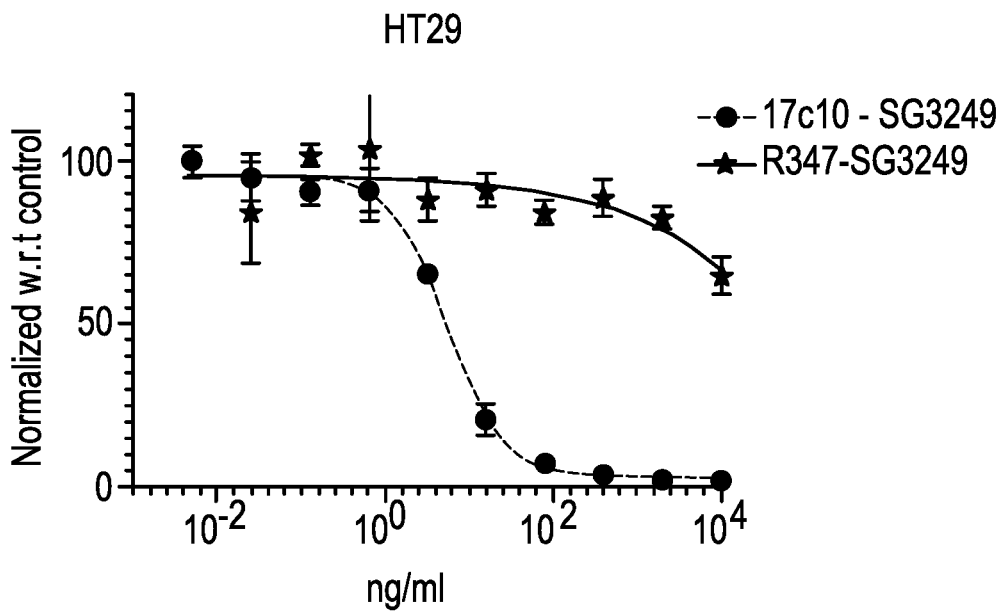

FIG. 11A shows the relative viability normalized to that of cells treated with a control antibody conjugated to SG3249 with anti-ASCT2 antibody 17c10 conjugated to SG3249.

Figure 11B:
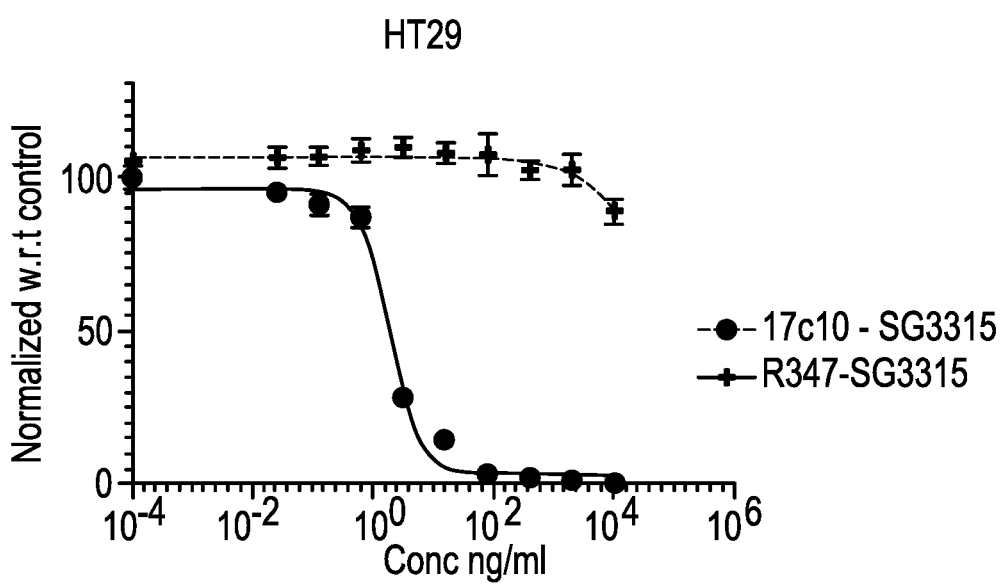

FIG. 11B shows the relative viability normalized to that of cells treated with a control antibody conjugated to SG3315 with anti-ASCT2 antibody 17c10 conjugated to SG3315.

Figure 12A:
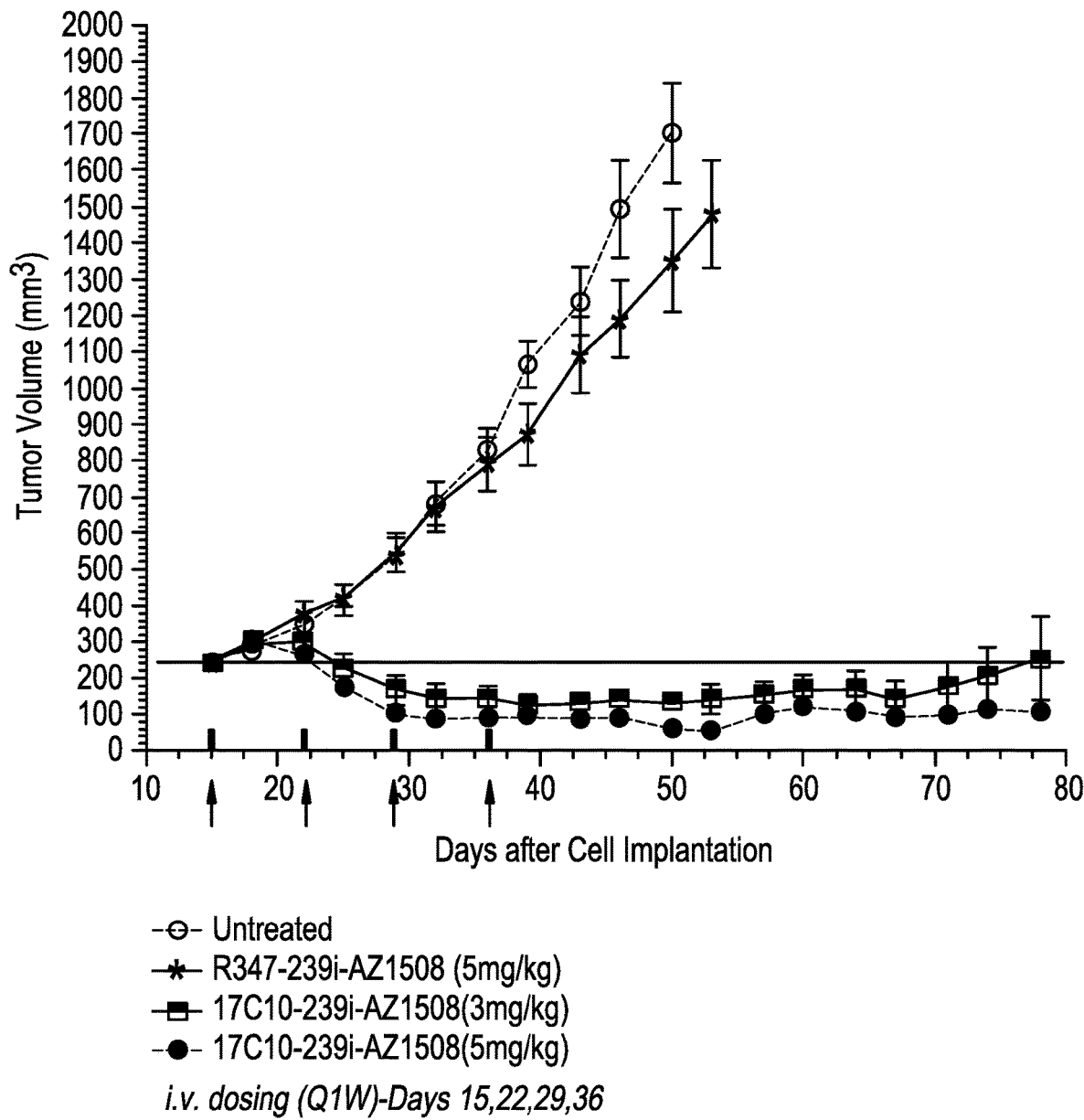
Figure 12B:
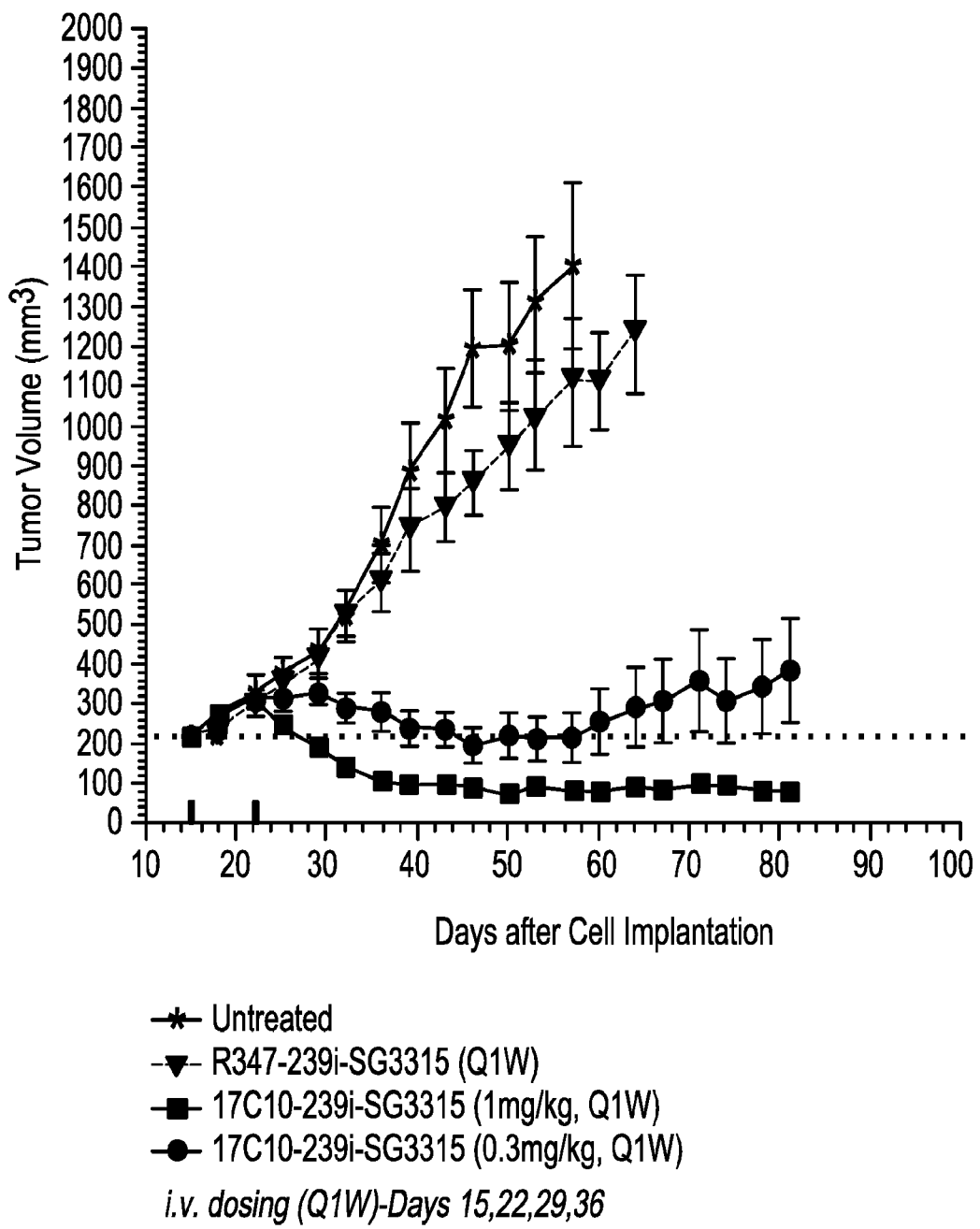
Figure 12C:
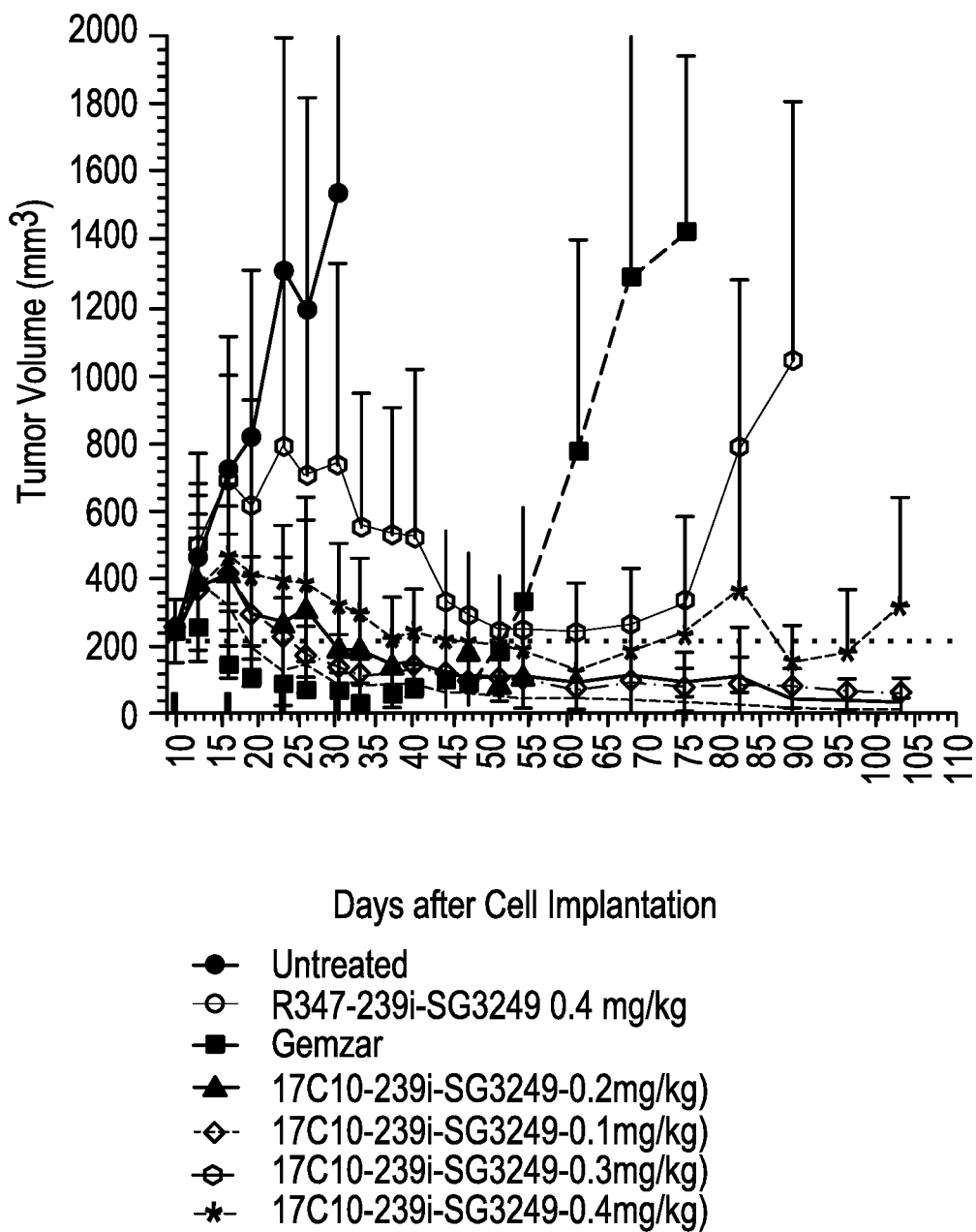

FIG. 12A, FIG. 12B, and FIG. 12C shows time course of the tumor volume in a WiDr colorectal cancer or primary pancreatic cancer xenograft model after treatment with anti-ASCT2 antibody 17c10 conjugated to tubulysin or PBDs. FIG. 12A, the 17c10 antibody is conjugated to tubulysin 1508; FIG. 12B, the anti-ASCT2 antibody 17c10 is conjugated to SG 3315; FIG. 12C, the anti-ASCT2 antibody 17c10 is conjugated to SG 3249.

Figure 13A:
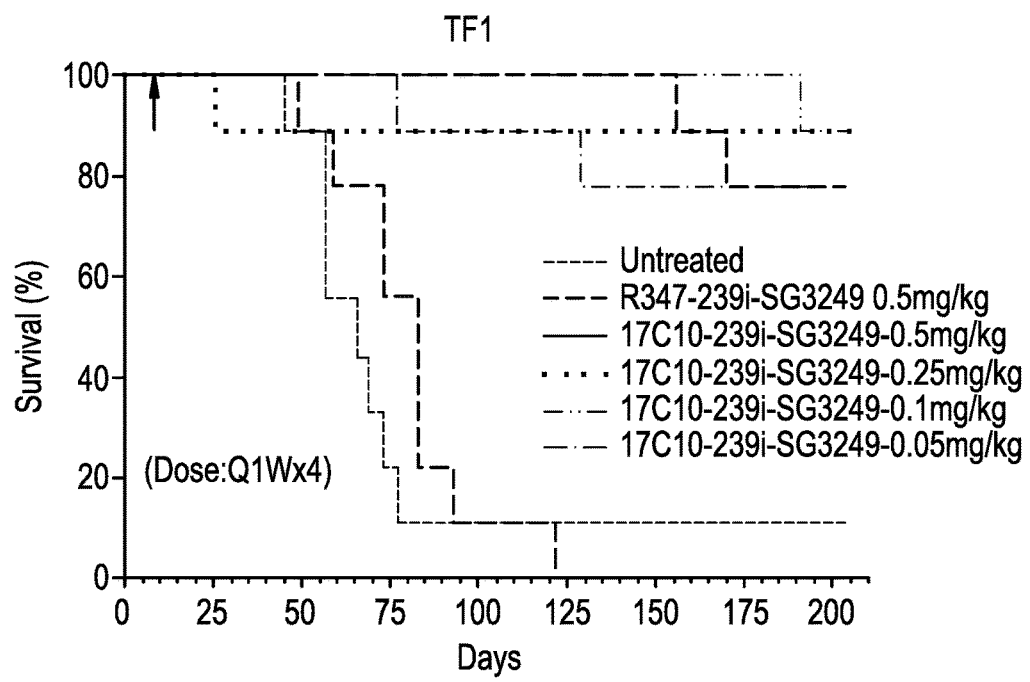

FIG. 13A shows anti-tumor efficacy of an ASCT2-PBD ADC (antibody 17c10 is conjugated to SG3249) in a disseminated TF1alpha AML mouse model. The ADC and the isotype control were administered on a Q1Wx4 schedule. Morbidity and mortality was monitored daily. All dose levels of the ADC (0.05, 0.1, 0.25 and 0.5 mg/kg) significantly improved the survival compared to the untreated control group. The data are presented in a Kaplan-Meier survival plot showing the fate of the individual animals within each group.

Figure 13B:
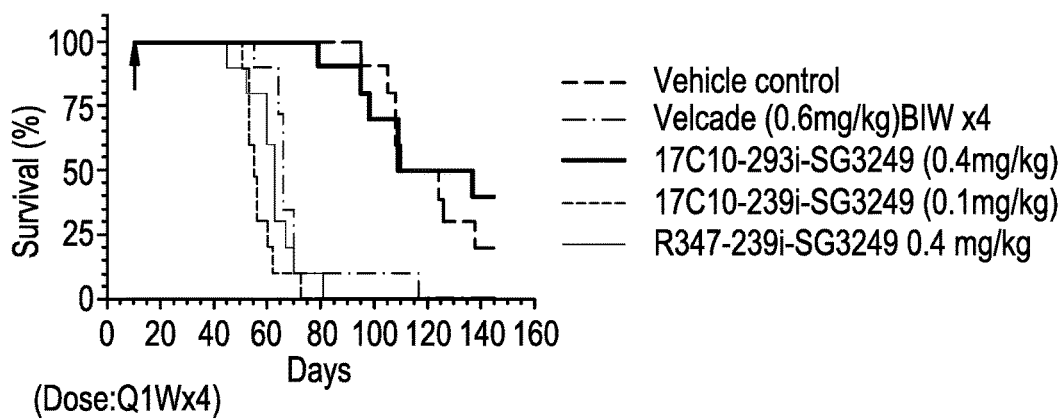

FIG. 13B shows anti-tumor efficacy of an ASCT2-PBD ADC (antibody 17c10 is conjugated to SG3249) in a disseminated MM.1S MM mouse model. Mice were treated with the ADC or isotype control as described in FIG. 13A. Morbidity and mortality were monitored daily. Both dose levels of the ADC (0.1 and 0.4 mg/kg) significantly improved the survival (117 and 123.5 days, respectively) compared to the untreated control group (55.5 days). The data are presented in a Kaplan-Meier survival plot showing the fate of the individual animals within each group.

DETAILED DESCRIPTION OF THE INVENTION

The present invention provides antibodies and antigen-binding fragments thereof that specifically bind to ASCT2. In certain embodiments, the antibody, or antigen-binding fragment is conjugated to an agent, preferably a cytotoxin. Polynucleotides encoding the antibodies and antigen-binding fragments thereof, vectors containing the polynucleotides, and host cells expressing the antibodies are included. Compositions comprising the anti-ASCT2 antibodies or antigen-binding fragments thereof, and methods of making the anti-ASCT2 antibodies and antigen-binding fragments are also provided. Methods of using the novel anti-ASCT2 antibodies, such as in diagnostic applications or in methods of treating a disease or disorder characterized by ASCT2 overexpression, e.g., cancer, are further provided.

In order that the present invention can be more readily understood, certain terms are first defined. Additional definitions are set forth throughout the Detailed Description.

I. Definitions

As used in this specification and the appended claims, the singular forms "a," "an," and "the" include plural referents unless the context clearly dictates otherwise. The terms "a" or "an," as well as the terms "one or more" and "at least one" can be used interchangeably herein.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Wherever embodiments are described with the language "comprising," otherwise analogous embodiments described in terms of "consisting of" and/or "consisting essentially of" are included.

Unless defined otherwise, all technical and scientific terms used herein have the same meaning as commonly understood by one of ordinary skill in the art to which this invention is related. For example, *The Dictionary of Cell and Molecular Biology* (5th ed. J. M. Lackie ed., 2013), the *Oxford Dictionary of Biochemistry and Molecular Biology* (2d ed. R. Cammack et al. eds., 2008), and *The Concise Dictionary of Biomedicine and Molecular Biology*, P-S. Juo, (2d ed. 2002) can provide one of skill with general definitions of some terms used herein.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

Amino acids are referred to herein by their commonly known three letter symbols or by the one-letter symbols recommended by the IUPAC-IUB Biochemical Nomenclature Commission. Nucleotides, likewise, are referred to by their commonly accepted single-letter codes.

The term "ASCT2" refers to the system ASC amino acid transporter 2 protein, and/or active fragments thereof. ASCT2 is a transmembrane protein that mediates transport of small neutral amino acids, including glutamine, alanine, and serine, cysteine, and threonine, in a $Na^+$-dependent manner. The RNA, DNA, and amino acid sequences of ASCT2 are known to those skilled in the art and can be found in many databases, for example, in the databases of the National Center for Biotechnology Information (NCBI). Examples of these sequences found at NCBI are human ASCT2 sequences having GenBank Accession Numbers NM_005628 and NP_005619, cynomolgus monkey (*Macaca fascicularis*) ASCT2 sequences having GenBank Accession NM 001284054 and NP-001270983.

The terms "inhibit," "block," and "suppress" are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in a biological activity or process.

The terms "antibody" or "immunoglobulin," as used interchangeably herein. A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, Cl. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Exemplary antibodies of the present disclosure include the hybridoma-produced murine monoclonal antibodies 17c10 and 1e8, humanized, affinity optimized, germlined, and/or other versions of these antibodies, and serum half-lifeoptimized anti-ASCT2 YTE antibodies (e.g., K44VHa-N56Q, K44VHa6-N56Q, or K2Ha-N56Q).

The term "germlining" means that amino acids at specific positions in an antibody are mutated back to those in the germ line.

The term "antibody" can refer to an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules such as toxins, radioisotopes, etc.

The term "ASCT2 antibody" or "antibody that binds to ASCT2" or "anti-ASCT2" refers to an antibody that is capable of binding ASCT2 with sufficient affinity such that the antibody is useful as a therapeutic agent or a diagnostic reagent in targeting ASCT2. The extent of binding of an anti-ASCT2 antibody to an unrelated, non-ASCT2 protein is less than about 10% of the binding of the antibody to ASCT2 as measured, e.g., by a radioimmunoassay (RIA), BIA-CORE® (using recombinant ASCT2 as the analyte and antibody as the ligand, or vice versa), KINEXA®, or other binding assays known in the art. In certain embodiments, an antibody that binds to ASCT2 has a dissociation constant ($K_D$) of ≤1 µM, ≤100 nM, ≤10 nM, ≤1 nM, ≤0.1 nM, ≤10 pM, ≤1 pM, or ≤0.1 pM.

The term "antigen-binding fragment" refers to a portion of an intact antibody and refers to the complementarity determining variable regions of an intact antibody. Fragments of a full-length antibody can be an antigen-binding fragment of an antibody. Examples of antibody fragments include, but are not limited to Fab, Fab', F(ab')2, and Fv fragments, linear antibodies, single chain antibodies (e.g., ScFvs), and multi specific antibodies formed from antibody fragments.

A "monoclonal antibody" (mAb) refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, hybridoma, phage selection, recombinant expression, and transgenic animals.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, *Nature*, 321:522-525; Riechmann et al., 1988, *Nature*, 332:323-327; Verhoeyen et al., 1988, *Science*, 239:1534-1536). In some instances, the Fv framework region (FW) residues of a human immunoglobulin are replaced with the corresponding residues in an antibody from a non-human species that has the desired specificity, affinity, and capability.

Humanized antibodies can be further modified by the substitution of additional residues either in the Fv framework region and/or within the replaced non-human residues to refine and optimize antibody specificity, affinity, and/or capability. In general, humanized antibodies will comprise substantially all of at least one, and typically two or three, variable domains containing all or substantially all of the CDR regions that correspond to the non-human immunoglobulin whereas all or substantially all of the FR regions are those of a human immunoglobulin consensus sequence. Humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. As used herein, "pharmaceutically acceptable carrier" includes any and all solvents, dispersion media, coatings, antibacterial and antifungal agents, isotonic and absorption/resorption delaying agents, and the like that are physiologically compatible.

A "variable region" of an antibody refers to the variable region of the antibody light chain or the variable region of the antibody heavy chain, either alone or in combination. The variable regions of the heavy and light chain each consist of four framework regions (FW) connected by three complementarity-determining regions (CDRs), also known as hypervariable regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) *J. Molec. Biol.* 273:927-948)). In addition, combinations of these two approaches are sometimes used in the art to determine CDRs.

The "Kabat numbering system" is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop, when numbered using the Kabat numbering convention, varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. Table 1, below lists the positions of the amino acids comprising the variable regions of the antibodies in each system.

TABLE 1

AMINO ACID POSITIONS IN EACH SYSTEM

| Region | Kabat | AbM | Chothia |
|---|---|---|---|
| LCDR1 | L24-L34 | L24-L34 | L24-L34 |
| LCDR2 | L50-L56 | L50-L56 | L50-L56 |
| LCDR3 | L89-L97 | L89-L97 | L89-L97 |
| HCDR1[1] | H31-H35B | H26-H35B | H26-H32..34 |
| HCDR1[2] | H31-H35 | H26-H35 | H26-H32 |
| HCDR2 | H50-H65 | H50-H58 | H52-H56 |
| HCDR3 | H95-H102 | H95-H102 | H95-H102 |

[1]Kabat Numbering
[2]Chothia Numbering

ImMunoGeneTics (IMGT) also provides a numbering system for the immunoglobulin variable regions, including the CDRs. See, e.g., Lefranc, M. P. et al., *Dev. Comp. Immunol.* 27: 55-77(2003). The IMGT numbering system is based on an alignment of more than 5,000 sequences, structural data, and characterization of hypervariable loops and allows for easy comparison of the variable and CDR regions for all species. According to the IMGT numbering schema, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

As used throughout the specification the VH CDRs sequences described correspond to the classical Kabat numbering locations, namely Kabat VH-CDR1 is at positions 31-35, VH-CDR2 is a positions 50-65, and VH-CDR3 is at positions 95-102. VL-CDR1, VL-CDR2 and VL-CDR3 also correspond to classical Kabat numbering locations, namely positions 24-34, 50-56 and 89-97, respectively.

The term "human antibody" means an antibody produced in a human or an antibody having an amino acid sequence corresponding to an antibody produced in a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies in which the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The terms "YTE" or "YTE mutant" refer to a mutation in IgG1 Fc that results in an increase in the binding to human FcRn and improves the serum half-life of the antibody having the mutation. A YTE mutant comprises a combination of three mutations, M252Y/S254T/T256E (EU numbering Kabat et al. (1991) Sequences of Proteins of Immunological Interest, U.S. Public Health Service, National Institutes of Health, Washington, D.C.), introduced into the heavy chain of an IgG1. See U.S. Pat. No. 7,658,921, which is incorporated by reference herein. The YTE mutant has been shown to increase the serum half-life of antibodies approximately four-times as compared to wild-type versions of the same antibody (Dall'Acqua et al., *J. Biol. Chem.* 281:23514-24 (2006); Robbie et al., (2013) *Antimicrob. Agents Chemother.* 57, 6147-6153). See also U.S. Pat. No. 7,083,784, which is hereby incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

Potency of binding molecule is normally expressed as an $IC_{50}$ value, in ng/ml unless otherwise stated. $IC_{50}$ is the median inhibitory concentration of an antibody molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $IC_{50}$ can be calculated by any number of means known in the art.

The fold improvement in potency for the antibodies or polypeptides of the invention as compared to a reference antibody can be at least about 2-fold, at least about 4-fold, at least about 6-fold, at least about 8-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

Binding potency of an antibody is normally expressed as an $EC_{50}$ value, in nM or pM unless otherwise stated. $EC_{50}$ is the concentration of a drug that induces a median response between baseline and maximum after a specified exposure time. $EC_{50}$ can be calculated by any number of means known in the art.

A "therapeutic antibody" is one that can be administered to a subject to treat or prevent a disease or condition. A "subject" is any individual, particularly a mammal, for whom diagnosis, prognosis, or therapy is desired. Mammalian subjects include humans, domestic animals, farm animals, sports animals, and zoo animals, e.g., humans, non-human primates, dogs, cats, guinea pigs, rabbits, rats, mice, horses, cattle, etc.

To "treat" refers to therapeutic measures that cure, slow down, lessen symptoms of, and/or halt progression of a diagnosed pathologic condition or disorder. Thus, those in need of treatment include those already with the disorder. In certain embodiments, a subject is successfully "treated" for a disease or disorder, for example, cancer, according to the methods provided herein if the patient shows, e.g., total, partial, or transient alleviation or elimination of symptoms associated with the disease or disorder.

To "prevent" refers to prophylactic or preventative measures that prevent and/or slow the development of a targeted pathologic condition or disorder. Thus, those in need of prevention include those prone to have or susceptible to the disorder. In certain embodiments, a disease or disorder is successfully prevented according to the methods provided herein if the patient develops, transiently or permanently, e.g., fewer or less severe symptoms associated with the disease or disorder, or a later onset of symptoms associated with the disease or disorder, than a patient who has not been subject to the methods of the invention.

The term "pharmaceutical composition" refers to a preparation that is in such form as to permit the biological activity of the active ingredient to be effective, and which contains no additional components which are unacceptably toxic to a subject to which the composition would be administered. Such composition can be sterile, and can comprise a pharmaceutically acceptable carrier, such as physiological saline. Suitable pharmaceutical compositions can comprise one or more of a buffer (e.g., acetate, phosphate or citrate buffer), a surfactant (e.g., polysorbate), a stabilizing agent (e.g., human albumin), a preservative (e.g., benzyl alcohol), and absorption promoter to enhance bioavailability, and/or other conventional solubilizing or dispersing agents.

An "effective amount" of an antibody as disclosed herein is an amount sufficient to carry out a specifically stated purpose. An "effective amount" can be determined empirically and in a routine manner, in relation to the stated purpose.

A "label" refers to a detectable compound or composition that is conjugated directly or indirectly to the binding molecule or antibody so as to generate a "labeled" binding molecule or antibody. The label can be detectable by itself (e.g., radioisotope labels or fluorescent labels) or, in the case of an enzymatic label, can catalyze chemical alteration of a substrate compound or composition that is detectable.

The terms "polypeptide," "peptide," and "protein" are used interchangeably herein to refer to polymers of amino acids of any length. The polymer can be linear or branched, it can comprise modified amino acids, and non-amino acids can interrupt it. The terms also encompass an amino acid polymer that has been modified naturally or by intervention: for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. In certain embodiments, the polypeptides can occur as single chains or associated chains.

A "polynucleotide," as used herein can include one or more "nucleic acids," "nucleic acid molecules," or "nucleic acid sequences," refers to a polymer of nucleotides of any length, and includes DNA and RNA. The polynucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "vector" means a construct, which is capable of delivering, and in some embodiments, expressing, one or more genes or sequences of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

A polypeptide, antibody, polynucleotide, vector, cell, or composition that is "isolated" is a polypeptide, antibody, polynucleotide, vector, cell, or composition that is in a form not found in nature. Isolated polypeptides, antibodies, polynucleotides, vectors, cells or compositions include those which have been purified to a degree that they are no longer in a form in which they are found in nature. In some embodiments, an antibody, polynucleotide, vector, cell, or composition that is isolated is substantially pure.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

One such non-limiting example of a sequence alignment algorithm is the algorithm described in Karlin et al., *Proc. Natl. Acad. Sci. USA*, 87:2264-2268 (1990), as modified by Karlin et al., *Proc. Natl. Acad. Sci. USA*, 90:5873-5877 (1993), and incorporated into the NBLAST and XBLAST programs (Altschul et al., *Nucleic Acids Res.* 25:3389-3402 (1991)). In certain embodiments, Gapped BLAST can be used as described by Altschul et al., *Nucleic Acids Res.* 25:3389-3402 (1997). BLAST-2, WU-BLAST-2 (Altschul et al., *Methods in Enzymol.* 266:460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* 48:444-453 (1970)) can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (*CABIOS* 4:11-17 (1989)). For example, the percent identity can be determined using the ALIGN program (version 2.0) and using a PAM 120 with residue table, a gap length penalty of 12 and a gap penalty of 4. One skilled in the art can determine appropriate parameters for maximal alignment by particular alignment software. In certain embodiments, the default parameters of the alignment software are used.

In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the amino acid sequences of the binding molecules, antibodies, and antigen-binding fragments of the invention do not abrogate the binding of the binding molecule, antibody, or antigen-binding fragment containing the amino acid sequence, to the antigen(s), i.e., the ASCT2 to which the binding molecule, antibody, or antigen-binding fragment binds. Methods of identifying nucleotide and amino acid conservative substitutions which do not eliminate antigen-binding are well-known in the art. See, e.g., Brummell et al., *Biochem.* 32: 1180-1 187 (1993); Kobayashi et al., *Protein Eng.* 12(10):879-884 (1999); Burks et al., *Proc. Natl. Acad. Sci. USA* 94:412-417 (1997).

II. Anti-Asct2-Antibodies and Antigen-Binding Fragments

The present invention provides anti-ASCT2 antibodies and antigen-binding fragments thereof, which specifically bind ASCT2. The full-length amino acid (aa) and nucleotide (nt) sequences for human and cynomolgus monkey ASCT2 are known in the art, and can be found, at least, in the National Center for Biotechnology Information (NCBI) database. The NCBI database is available online. In some embodiments, the anti-ASCT2 antibodies or antigen-binding fragments thereof provided herein are humanized antibodies or human antibodies. In some embodiments, the anti-ASCT2 antibodies are conjugated to a cytotoxin, thus they are referred to as anti-ASTC2 ADCs.

In some embodiments, the anti-ASCT2 antibodies of the invention bind to ASCT2 on the surface of a cell and are internalized into the cell. In some embodiments, an anti-ASCT2 antibody is internalized into ASCT2-expressing cells with an $IC_{50}$ at 10 minutes of about 100 ng/ml to about 1 µg/ml, about 100 ng/ml to about 500 ng/ml, about 100 ng/ml to about 250 ng/ml, about 250 ng/ml to about 500 ng/ml, about 350 ng/ml to about 450 ng/ml, about 500 ng/ml to about 1 µg/ml, about 500 ng/ml to about 750 ng/ml, about 750 ng/ml to about 850 ng/ml, or about 900 ng/ml to about 1 µg/ml. In some embodiments, an anti-ASCT2 antibody is internalized into ASCT2-expressing cells with an $IC_{50}$ at 30 minutes of about 100 ng/ml to about 1 µg/ml, about 100 ng/ml to about 500 ng/ml, about 100 ng/ml to about 250 ng/ml, about 250 ng/ml to about 500 ng/ml, about 250 ng/ml to about 350 ng/ml, about 350 ng/ml to about 450 ng/ml, about 500 ng/ml to about 1 µg/ml, about 500 ng/ml to about 750 ng/ml, about 750 ng/ml to about 850 ng/ml, or about 900 ng/ml to about 1 µg/ml. In some embodiments, an anti-ASCT2 antibody is internalized into ASCT2-expressing cells with an $IC_{50}$ at 120 minutes of about 50 ng/ml to about 500 ng/ml, about 50 ng/ml to about 100 ng/ml, about 100 ng/ml to about 200 ng/ml, about 200 ng/ml to about 300 ng/ml, about 300 ng/ml to about 400 ng/ml, or about 400 ng/ml to about 500 ng/ml. In some embodiments, an anti-ASCT2 antibody is internalized into ASCT2-expressing cells with an $IC_{50}$ at 8 hours of about 5 ng/ml to about 250 ng/ml, about 10 ng/ml to about 25 ng/ml, about 25 ng/ml to about 50 ng/ml, about 50 ng/ml to about 100 ng/ml, about 100 ng/ml to about 150 ng/ml, about 150 ng/ml to about 200 ng/ml, or about 200 ng/ml to about 250 ng/ml. In some instances, the anti-ASCT2 antibody conjugated to a cytotoxin is an anti-ASCT2 ADC.

In certain aspects, this disclosure provides an anti-ASCT2 antibody or antigen-binding fragment thereof comprising three heavy chain complementarity determining regions (HCDRs) and three light chain complementarity determining regions (LCDRs). In certain aspects, the HCDR1 has an amino acid sequence selected from SEQ ID NO: 10 and SEQ ID NO: 16; the HCDR2 has an amino acid sequence selected from SEQ ID NO: 22, SEQ ID NO: 11, and SEQ ID NO: 17; the HCDR3 has an amino acid sequence selected from SEQ ID NO: 23, SEQ ID NO: 12, and SEQ ID NO; 18; the LCDR1 has an amino acid sequence selected from SEQ ID NO: 13 and SEQ ID NO: 19; the LCDR2 has an amino acid sequence selected from SEQ ID NO: 14, SEQ ID NO: 20, and SEQ ID NO: 24; the LCDR3 has an amino acid sequence selected from SEQ ID NO: 15, SEQ ID NO: 21, and SEQ ID NO: 25. As provided herein, the VH comprises an amino acid sequence of SEQ ID NO: 1 or SEQ ID NO: 5; and the VL comprises an amino acid sequence of SEQ ID NO: 2 or SEQ ID NO: 6. In some aspects, the anti-ASCT2 antibody comprises a VH of an amino acid sequence of SEQ ID NO: 5 and a VL of an amino acid sequence of SEQ ID NO: 6. Optionally, an anti-ASCT2 antibody comprises a VH of an amino acid sequence of SEQ ID NO: 3 or SEQ ID NO: 7, and a VL of an amino acid sequence of SEQ ID NO: 4 or SEQ ID NO: 8. In some embodiments, the anti-ASCT2 antibody comprises a VH of an amino acid sequence of SEQ ID NO: 7 and a VL of an amino acid sequence of SEQ ID NO: 8.

Further, the disclosure provides an isolated antibody or antigen-binding fragment thereof which specifically binds to ASCT2 comprising a VH and a VL, where the VH and VL contain, respectively, amino acid sequences at least 70%, 75%, 80%, 85%, 90%, 95%, or 100%/o identical to reference amino acid sequences SEQ ID NO: 1 and SEQ ID NO: 2; SEQ ID NO: 3 and SEQ ID NO: 4; SEQ ID NO: 5 and SEQ ID NO: 6; or SEQ ID NO: 7 and SEQ ID NO: 8, respectively.

In one aspect, the disclosure provides an anti-ASCT2 antibody or antigen-binding fragment thereof comprising VH amino acid sequence SEQ ID NO: 5 and the VL amino acid sequence SEQ ID NO: 6. In one aspect, the disclosure provides an anti-ASCT2 antibody or antigen-binding fragment thereof comprising VH amino acid sequence SEQ ID NO: 7 and the VL amino acid sequence SEQ ID NO: 8.

An anti-ASCT2 antibody or antigen-binding fragment thereof as described herein can be, e.g., a murine antibody, a humanized antibody, a chimeric antibody, a monoclonal antibody, a polyclonal antibody, a recombinant antibody, a multispecific antibody, or any combination thereof. An anti-ASCT2 antibody antigen-binding fragment can be an Fv fragment, an Fab fragment, an F(ab')2 fragment, an Fab' fragment, a dsFv fragment, an scFv fragment, or an sc(Fv)2 fragment.

In one aspect, the disclosure provides an anti-ASCT2 antibody or antigen-binding fragment thereof that can bind to ASCT2 molecules across species, e.g., the antibody or fragment can bind to mouse ASCT2, rat ASCT2, rabbit, ASCT2, human ASCT2 and/or cynomolgus monkey ASCT2. For example, the antibody or fragment can bind to human ASCT2 and cynomolgus monkey ASCT2. In a further example, the antibody or fragment can also bind to mouse ASCT2.

In certain embodiments provided herein, an anti-ASCT2 antibody or antigen binding fragment thereof can specifically bind to ASCT2, e.g., human ASCT2 and cynomolgus monkey ASCT2, but does not specifically bind to human ASCT1.

An anti-ASCT2 antibody or antigen-binding fragment thereof as described herein can include, in addition to a VH and a VL, a heavy chain constant region or fragment thereof. In certain aspects the heavy chain constant region is a human heavy chain constant region, e.g., a human IgG constant region, e.g., a human IgG1 constant region. In some embodiments, particularly where the antibody or antigen-binding fragment thereof is conjugated to an agent, such as a cytotoxic agent, a cysteine residue is inserted between amino acid S239 and V240 in the CH2 region of IgG1. This cysteine is referred to as "a 239 insertion" or "239i."

In certain aspects, a heavy chain constant region or fragment thereof, e.g., a human IgG constant region or fragment thereof, can include one or more amino acid substitutions relative to a wild-type IgG constant domain wherein the modified IgG has an increased half-life compared to the half-life of an IgG having the wild-type IgG constant domain. For example, the IgG constant domain can contain one or more amino acid substitutions of amino acid residues at positions 251-257, 285-290, 308-314, 385-389, and 428-436, wherein the amino acid position numbering is according to the EU index as set forth in Kabat. In certain aspects the IgG constant domain can contain one or more of a substitution of the amino acid at Kabat position 252 with Tyrosine (Y), Phenylalanine (F), Tryptophan (W), or Threonine (T), a substitution of the amino acid at Kabat position 254 with Threonine (T), a substitution of the amino acid at Kabat position 256 with Serine (S), Arginine (R), Glutamine (Q), Glutamic acid (E), Aspartic acid (D), or Threonine (T), a substitution of the amino acid at Kabat position 257 with Leucine (L), a substitution of the amino acid at Kabat position 309 with Proline (P), a substitution of the amino acid at Kabat position 311 with Serine (S), a substitution of the amino acid at Kabat position 428 with Threonine (T), Leucine (L), Phenylalanine (F), or Serine (S), a substitution of the amino acid at Kabat position 433 with Arginine (R), Serine (S), Isoleucine (I), Proline (P), or Glutamine (Q), or a substitution of the amino acid at Kabat position 434 with Tryptophan (W), Methionine (M), Serine (S), Histidine (H), Phenylalanine (F), or Tyrosine. More specifically, the IgG constant domain can contain amino acid substitutions relative to a wild-type human IgG constant domain including as substitution of the amino acid at Kabat position 252 with Tyrosine (Y), a substitution of the amino acid at Kabat position 254 with Threonine (T), and a substitution of the amino acid at Kabat position 256 with Glutamic acid (E). This disclosure provides an anti-ASCT2 antibody or antigen-binding fragment thereof where the heavy chain is a human IgG1 YTE mutant.

An anti-ASCT2 antibody or antigen-binding fragment thereof provided herein, e.g., as described above, can include, in addition to a VH and a VL, and optionally a heavy chain constant region or fragment thereof, a light chain constant region or fragment thereof. In certain aspects the light chain constant region is a kappa lambda light chain constant region, e.g., a human kappa constant region or a human lambda constant region.

As noted above, a VH and/or VL amino acid sequence can be, e.g., 85%, 90%, 95%, 96%, 97%, 98% or 99% similar to a sequence set forth herein, and/or comprise 1, 2, 3, 4, 5 or more substitutions, e.g., conservative substitutions relative to a sequence set forth herein. An ASCT2 antibody having VH and VL regions having a certain percent similarity to a VH region or VL region, or having one or more substitutions, e.g., conservative substitutions can be obtained by mutagenesis (e.g., site-directed or PCR-mediated mutagenesis) of nucleic acid molecules encoding VH and/or VL regions described herein, followed by testing of the encoded altered antibody for binding to ASCT2 and optionally testing for retained function using the functional assays described herein.

The affinity or avidity of an antibody for an antigen can be determined experimentally using any suitable method well known in the art, e.g., flow cytometry, enzyme-linked immunosorbent assay (ELISA), or radioimmunoassay (RIA), or kinetics (e.g., KINEXA® or BIACORE™ analysis). Direct binding assays as well as competitive binding assay formats can be readily employed. (See, e.g., Berzofsky et al., Antibody-Antigen Interactions, In Fundamental Immunology, Paul, W. E., Ed., Raven Press: New York, N.Y. (1984); Kuby, Immunology, W. H. Freeman and Company: New York, N.Y. (1992); and methods described herein.) The measured affinity of a particular antibody-antigen interaction can vary if measured under different conditions (e.g., salt concentration, pH, temperature). Thus, measurements of affinity and other antigen-binding parameters (e.g., $K_D$ or Kd, $K_{on}$, $K_{off}$) are made with standardized solutions of antibody and antigen, and a standardized buffer, as known in the art.

In some embodiments, an anti-ASCT2 antibody or antigen-binding fragment thereof, can bind to ASCT2-expressing cells with an $IC_{50}$ lower than about 500 nM, lower than about 350 nM, lower than about 250 nM, lower than about 150 nM, lower than about 100 nM, lower than about 75 nM, lower than about 60 nM, lower than about 50 nM, lower than about 40 nM, lower than about 30 nM, lower than about 20 nM, lower than about 15 nM, lower than about 10 nM, lower than about 5 nM, lower than about 1 nM, lower than about 500 pM, lower than about 350 pM, lower than about 250 pM, lower than about 150 pM, lower than about 100 pM, lower than about 75 pM, lower than about 60 pM, lower than about 50 pM, lower than about 40 pM, lower than about 30 pM, lower than about 20 pM, lower than about 15 pM, lower than about 10 pM, or lower than about 5 pM, as measured by flow cytometry.

III. Binding Molecules That Bind to the Same Epitope as Anti-Asct2 Antibodies and Antigen-Binding Fragments Thereof In certain embodiments this disclosure provides an anti-ASCT2 antibody that binds to the same epitope as do the anti-ASCT2 antibodies described herein. The term "epitope" refers to a target protein determinant capable of binding to an antibody of the invention. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. Such antibodies can be identified based on their ability to cross-compete (e.g., to competitively inhibit the binding of, in a statistically significant manner) with antibodies such as those described herein in standard ASCT2 binding or activity assays.

Accordingly, in one embodiment, the invention provides anti-ASCT2 antibodies and antigen-binding fragments thereof, e.g., monoclonal antibodies, which compete for binding to ASCT2 with another anti-ASCT2 antibody or antigen-binding fragment thereof of the invention, such as murine monoclonal antibodies 17c10 or 1e8, or humanized variants as disclosed herein. The ability of a test antibody to inhibit the binding of, e.g., 17c10 or 1e8 demonstrates that the test antibody can compete with that antibody for binding to ASCT2; such an antibody can, according to non-limiting theory, bind to the same or a related (e.g., a structurally similar or spatially proximal) epitope on ASCT2 as the anti-ASCT2 antibody or antigen-binding fragment thereof with which it competes. In one embodiment, the anti-ASCT2 antibody or antigen-binding fragment thereof that binds to the same epitope on ASCT2 as, e.g., murine monoclonal antibodies 17c10 or 1e8.

IV. Preparation of Anti-Asct2 Antibodies and Antigen-Binding Fragments

Monoclonal anti-ASCT2 antibodies can be prepared using hybridoma methods, such as those described by Kohler and Milstein, *Nature* 256:495 (1975). Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or an in vitro binding assay, e.g., radioimmunoassay (RIA) or enzyme-linked immunosorbent assay (ELISA), can then be propagated either in in vitro culture using standard methods (Goding, *Monoclonal Antibodies: Principles and Practice*, Academic Press, 1986) or in vivo as ascites tumors in an animal. The monoclonal antibodies can then be purified from the culture medium or ascites fluid using known methods.

Alternatively anti-ASCT2 monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant anti-ASCT2 monoclonal antibodies or antigen-binding fragments thereof of the desired species can be isolated from phage display libraries expressing CDRs of the desired species as described in McCafferty et al., *Nature* 348:552-554 (1990); Clackson et al., *Nature,* 352:624-628 (1991); and Marks et al., *J. Mol. Biol.* 222:581-597 (1991).

The polynucleotide(s) encoding an anti-ASCT2 antibody or an antigen-binding fragment thereof can further be modified in a number of different manners using recombinant DNA technology to generate alternative antibodies. In some embodiments, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In certain embodiments, the anti-ASCT2 antibody or antigen-binding fragment thereof is a human antibody or antigen-binding fragment thereof. Human antibodies can be directly prepared using various techniques known in the art. Immortalized human B lymphocytes immunized in vitro or isolated from an immunized individual that produce an antibody directed against a target antigen can be generated. See, e.g., Cole et al., *Monoclonal Antibodies and Cancer Therapy*, Alan R. Liss, p. 77 (1985); Boemer et al., *J. Immunol.* 147 (1):86-95 (1991); U.S. Pat. No. 5,750,373.

Also, the anti-ASCT2 human antibody or antigen-binding fragment thereof can be selected from a phage library, where that phage library expresses human antibodies, as described, for example, in Vaughan et al., *Nat. Biotech.* 14:309-314 (1996); Sheets et al., *Proc. Natl. Acad. Sci. USA,* 95:6157-6162 (1998); Hoogenboom and Winter, *J. Mol. Biol.* 227: 381 (1991); and Marks et al., *J. Mol. Biol.* 222:581 (1991). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., *J. Molec. Biol.* 376:1182-1200 (2008), each of which is incorporated by reference in its entirety.

Affinity maturation strategies and chain shuffling strategies are known in the art and can be employed to generate high affinity human antibodies or antigen-binding fragments thereof. See Marks et al., *BioTechnology* 10:779-783 (1992), incorporated by reference in its entirety.

In some embodiments, an anti-ASCT2 monoclonal antibody can be a humanized antibody. Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate, or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing ASCT2 binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the antigen ASCT2 and other favorable biological properties. To achieve this goal, humanized (or human) or engineered anti-ASCT2 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as ASCT2. In this way, FW residues can be selected and combined from the consensus and import sequences so that the desired antibody characteristic, such as increased affinity for the target antigen(s), is achieved.

Humanization, resurfacing or engineering of anti-ASCT2 antibodies or antigen-binding fragments thereof of the present invention can be performed using any known method, such as but not limited to those described in, Jones et al., *Nature* 321:522 (1986); Riechmann et al., *Nature* 332:323 (1988); Verhoeyen et al., *Science* 239:1534 (1988); Sims et al., *J. Immunol.* 151: 2296 (1993); Chothia and Lesk, *J. Mol. Biol.* 196:901 (1987); Carter et al., *Proc. Natl. Acad. Sci. USA* 89:4285 (1992); Presta et al., *J. Immunol.* 151:2623 (1993); U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, 7,557,189; 7,538,195; and 7,342,110; International Application Nos. PCT/US98/16280; PCT/US96/18978; PCT/US91/09630; PCT/US91/05939; PCT/US94/01234; PCT/GB89/01334; PCT/GB91/01134; PCT/GB92/01755; International Patent Application Publication Nos. WO90/14443; WO90/14424; WO90/14430; and European Patent Publication No. EP 229246; each of which is entirely incorporated herein by reference, including the references cited therein.

Anti-ASCT2 humanized antibodies and antigen-binding fragments thereof can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments an anti-ASCT2 antibody fragment is provided. Various techniques are known for the production of antibody fragments. Traditionally, these fragments are derived via proteolytic digestion of intact antibodies, as described, for example, by Morimoto et al., *J. Biochem. Biophys. Meth.* 24:107-117 (1993) and Brennan et al., *Science* 229:81 (1985). In certain embodiments, anti-ASCT2 antibody fragments are produced recombinantly. Fab, Fv, and scFv antibody fragments can all be expressed in and secreted from *E. coli* or other host cells, thus allowing the production of large amounts of these fragments. Such anti-ASCT2 antibody fragments can also be isolated from the antibody phage libraries discussed above. The anti-ASCT2 antibody fragments can also be linear antibodies as described in U.S. Pat. No. 5,641,870. Other techniques for the production of antibody fragments will be apparent to the skilled practitioner.

According to the present invention, techniques can be adapted for the production of single-chain antibodies specific to ASCT2. See, e.g., U.S. Pat. No. 4,946,778). In addition, methods can be adapted for the construction of Fab expression libraries to allow rapid and effective identification of monoclonal Fab fragments with the desired specificity for ASCT2, or derivatives, fragments, analogs or homologs thereof. See, e.g., Huse et al., *Science* 246:1275-1281 (1989). Antibody fragments can be produced by techniques known in the art including, but not limited to: F(ab')2 fragment produced by pepsin digestion of an antibody molecule; Fab fragment generated by reducing the disulfide bridges of an F(ab')2 fragment; Fab fragment generated by the treatment of the antibody molecule with papain and a reducing agent; or Fv fragments.

In certain aspects, an anti-ASCT2 antibody or antigen-binding fragment thereof can be modified in order to increase its serum half-life. This can be achieved, for example, by incorporation of a salvage receptor binding epitope into the antibody or antibody fragment, by mutation of the appropriate region in the antibody or antibody fragment or by incorporating the epitope into a peptide tag that is then fused to the antibody or antibody fragment at either end or in the middle (e.g., by DNA or peptide synthesis), or by YTE mutation. Other methods to increase the serum half-life of an antibody or antigen-binding fragment thereof, e.g., conjugation to a heterologous molecule, such as PEG, are known in the art.

Modified anti-ASCT2 antibodies or antigen-binding fragments thereof as provided herein can comprise any type of variable region that provides for the association of the antibody or polypeptide with ASCT2. In this regard, the variable region can comprise or be derived from any type of mammal that can be induced to mount a humoral response and generate immunoglobulins against the desired antigen. As such, the variable region of an anti-ASCT2 antibody or antigen-binding fragment thereof can be, for example, of human, murine, non-human primate (e.g., cynomolgus monkeys, macaques, etc.) or lupine origin. In some embodiments both the variable and constant regions of the modified anti-ASCT2 antibodies or antigen-binding fragments thereof are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains of an anti-ASCT2 antibody or antigen-binding fragment thereof are altered by at least partial replacement of one or more CDRs and/or by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It is not necessary to replace all of the CDRs with the complete CDRs from the donor variable region to transfer the antigen-binding capacity of one variable domain to another. Rather, it is only necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art to carry out routine experimentation to obtain a functional antibody with reduced immunogenicity.

Alterations to the variable region notwithstanding, those skilled in the art will appreciate that the modified anti-ASCT2 antibodies or antigen-binding fragments thereof of this invention will comprise antibodies (e.g., full-length antibodies or antigen-binding fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain can be replaced by a short amino acid spacer (e.g., 10 residues) that provides some of the molecular flexibility typically imparted by the absent constant region.

Besides their configuration, it is known in the art that the constant region mediates several effector functions. For example, antibodies bind to cells via the Fc region, with an Fc receptor site on the antibody Fc region binding to an Fc receptor (FcR) on a cell. There are a number of Fc receptors that are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, an anti-ASCT2 antibody or an antigen-binding fragment thereof provides for altered effector functions that, in turn, affect the biological profile of the administered antibody or antigen-binding fragment thereof. For example, the deletion or inactivation (through point mutations or other means) of a constant region domain can reduce Fc receptor binding of the circulating modified antibody. In other cases it can be that constant region modifications, consistent with this invention, moderate complement binding and thus reduce the serum half-life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well-known biochemical or molecular engineering techniques well within the purview of the skilled artisan.

In certain embodiments, an ASCT2-binding molecule that is an antibody or antigen-binding fragment thereof does not have one or more effector functions. For instance, in some embodiments, the antibody or antigen-binding fragment thereof has no antibody-dependent cellular cytotoxicity (ADCC) activity and/or no complement-dependent cytoxicity (CDC) activity. In certain embodiments, the anti-ASCT2 antibody or antigen-binding fragment thereof does not bind to an Fc receptor and/or complement factors. In certain embodiments, the antibody or antigen-binding fragment thereof has no effector function.

In certain embodiments, an anti-ASCT2 antibody or antigen-binding fragment thereof can be engineered to fuse the CH3 domain directly to the hinge region of the respective modified antibodies or fragments thereof. In other constructs a peptide spacer can be inserted between the hinge region and the modified CH2 and/or CH3 domains. For example, compatible constructs can be expressed in which the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. Amino acid spacers can, in some cases, prove to be immunogenic and elicit an unwanted immune response against the construct. Accordingly, in certain embodiments, any spacer added to the construct can be relatively non-immunogenic, or even omitted altogether, so as to maintain the desired biochemical qualities of the modified antibodies.

Besides the deletion of whole constant region domains, anti-ASCT2 antibodies or antigen-binding fragments thereof provided herein can be modified by the partial deletion or substitution of a few or even a single amino acid in a constant region. For example, the mutation of a single amino acid in selected areas of the CH2 domain can be enough to substantially reduce Fc binding and thereby increase tumor localization. Similarly one or more constant region domains that control the effector function (e.g., complement C Q binding) can be fully or partially deleted. Such partial deletions of the constant regions can improve selected characteristics of the antibody or antigen-binding fragment thereof (e.g., serum half-life) while leaving other desirable functions associated with the subject constant region domain intact. Moreover, the constant regions of the disclosed anti-ASCT2 antibodies and antigen-binding fragments thereof can be modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified antibody or antigen-binding fragment thereof. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents that are substantially homologous to the murine, chimeric, humanized or human anti-ASCT2 antibodies, or antigen-binding fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

An anti-ASCT2 antibody or antigen-binding fragment thereof can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in Remington's Pharmaceutical Sciences, 22nd ed., Ed. Lloyd V. Allen, Jr. (2012).

V. Anti-Asct2 Antibody Conjugates

The disclosure further provides an anti-ASCT2 antibody or fragment thereof as described above, conjugated to a heterologous agent. For purposes of the present invention, "conjugated" means linked via a covalent or ionic bond. In certain aspects the agent can be an antimicrobial agent, a therapeutic agent, a prodrug, a peptide, a protein, an enzyme, a lipid, a biological response modifier, a pharmaceutical agent, a lymphokine, a heterologous antibody or fragment thereof, a detectable label, a PEG, or a combination of two or more of any said agents. In some embodiments, such ASCT2-binding molecules are ASCT2-ADCs.

Thus, the present disclosure also provides an ADC comprising an anti-ASCT2 antibody disclosed herein, further comprising at least one cytotoxic agent. In some aspects, the ADC further comprises at least one optional spacer. In some aspects, the at least one spacer is a peptide spacer. In some aspects, the at least one spacer is a non-peptide spacer.

The cytotoxic agent or cytotoxin can be any molecule known in the art that inhibits or prevents the function of cells and/or causes destruction of cells (cell death), and/or exerts anti-neoplastic/anti-proliferative effects. A number of classes of cytotoxic agents are known to have potential utility in ADC molecules. These include, but are not limited to, amanitins, auristatins, daunomycins, doxorubicins, duocarmycins, dolastatins, enediynes, lexitropsins, taxanes, puromycins, maytansinoids, vinca alkaloids, tubulysins and pyrrolobenzodiazepines (PBDs). Examples of such cytotoxic agents are AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, vinblastine, methotrexate, and netropsin, and derivatives and analogs thereof. Additional disclosure regarding cytotoxins suitable for use in ADCs can be found, for example, in International Patent Application Publication Nos. WO 2015/155345 and WO 2015/157592, incorporated by reference herein in their entirety.

In one embodiment, the cytotoxic agent is a tubulysin or tubulysin derivative. Tubulysin A has the following chemical structure:

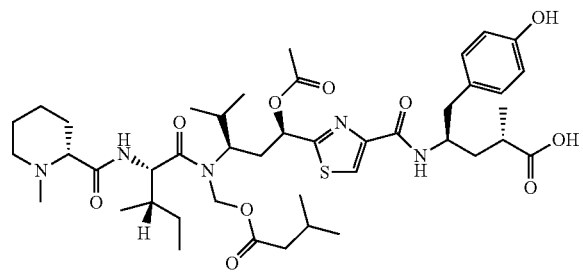 [SMILES: CC[C@H](C)[C@H](NC(=O)[C@H]1CCCCN1C)C(=O)N(COC(=O)CC(C)C)[C@H](C[C@@H](OC(C)=O)c1nc(C(=O)N[C@@H](Cc2ccc(O)cc2)C[C@H](C)C(=O)O)cs1)C(C)C]

Tubulysins are members of a class of natural products isolated from myxobacterial species (Sasse et al., *J. Antibiot.* 53:879-885 (2000)). As cytoskeleton-interacting agents, tubulysins are mitotic poisons that inhibit tubulin polymerization and lead to cell cycle arrest and apoptosis (Steinmetz et al., *Chem. Int. Ed.* 43:4888-4892 (2004); Khalil et al., *Chem. Biochem.* 7:678-683 (2006); Kaur et al., *Biochem. J.* 396: 235-242 (2006)). As used herein, the term "tubulysin" refers both collectively and individually to the naturally occurring tubulysins and analogs and derivatives of tubulysins. Illustrative examples of tubulysins are disclosed, for example, in WO2004005326A2, WO2012019123A1, WO2009134279A1, WO2009055562A1, WO2004005327A1, U.S. Pat. Nos. 7,776,841, 7,754,885, US20100240701, U.S. Pat. No. 7,816,377, US20110021568, and US20110263650, incorporated herein by reference. It is to be understood that such derivatives include, for example, tubulysin prodrugs or tubulysins that include one or more protection or protecting groups, one or more linking moieties.

In certain aspects, the tubulysin is tubulysin 1508, also referred to herein as "AZ1508" and described in more detail in WO 2015157594, incorporated herein by reference, having the following structure:

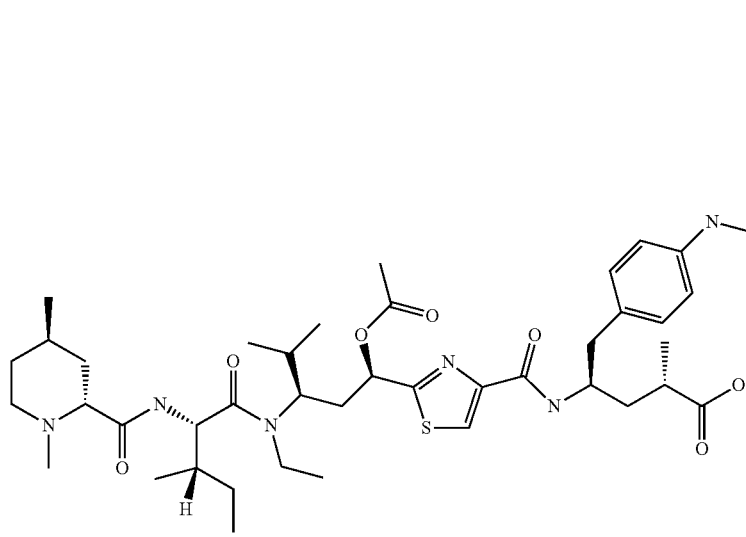

In another embodiment, the cytotoxic agent may be a pyrrolobenzodiazepine (PBD) or a PBD derivative. PBD translocates to the nucleus where it crosslinks DNA, preventing replication during mitosis, damaging DNA by inducing single strand breaks, and subsequently leading to apoptosis. Some PBDs have the ability to recognize and bond to specific sequences of DNA; the preferred sequence is PuGPu. PBDs are of the general structure:

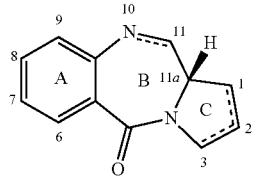

PBDs differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In Antibiotics Ill. Springer-Verlag, New York, pp. 3-11 (1975); Hurley and Needham-VanDevanter, *Acc. Chem. Res.*, 19, 230-237 (1986)). Their ability to form an adduct in the minor groove enables them to interfere with DNA processing, hence their use as anti-tumor agents.

The first PBD anti-tumor antibiotic, anthramycin, was discovered in 1965 (Leimgruber et al., *J. Am. Chem. Soc.* 87:5793-5795 (1965); Leimgruber et al., *J. Am. Chem. Soc.* 87:5791-5793 (1965)). Since then, a number of naturally occurring PBDs have been reported, and over 10 synthetic routes have been developed to a variety of analogues (Thurston et al., *Chem. Rev.* 1994:433-465 (1994); Antonow, D. and Thurston, D. E., *Chem. Rev.* 111:2815-2864 (2011)). Family members include abbeymycin (Hochlowski et al., *J. Antibiotics* 40:145-148 (1987)), chicamycin (Konishi et al., *J. Antibiotics* 37:200-206 (1984)), DC-81 (Japanese Patent 58-180 487; Thurston et al., *Chem. Brit.* 26:767-772 (1990); Bose et al., *Tetrahedron* 48:751-758 (1992)), mazethramycin (Kuminoto et al., *J. Antibiotics* 33:665-667 (1980)), neothramycins A and B (Takeuchi et al., *J. Antibiotics* 29:93-96 (1976)), porothramycin (Tsunakawa et al., *J. Antibiotics* 41:1366-1373 (1988)), prothracarcin (Shimizu et al., *J. Antibiotics* 29:2492-2503 (1982); Langley and Thurston, *J. Org. Chem.* 52:91-97 (1987)), sibanomicin (DC-102) (Hara et al., *J. Antibiotics* 41:702-704 (1988); Itoh et al., *J. Antibiotics* 41:1281-1284 (1988)), sibiromycin (Leber et al., *J. Am. Chem. Soc.* 110:2992-2993 (1988)) and tomamycin (Arima et al., *J. Antibiotics* 25:437-444 (1972)). PBDs and ADCs comprising them are also described in International Patent Application International Patent Application Publication Nos. WO 2015/155345 and WO 2015/157592, incorporated in by reference in their entirety herein by reference.

In certain aspects, the PBD is PBD 3249, also referred to herein as "SG3249" and described in more detail in WO 2014/057074, incorporated herein by reference, having the following structure:

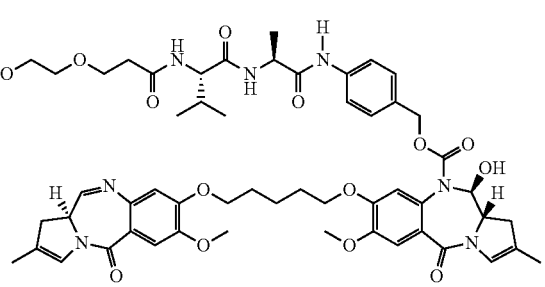

In certain aspects, the PBD is PBD 3315, also referred to herein as "SG3315" and described in more detail in WO 2015/052322, incorporated herein by reference, having the following structure:

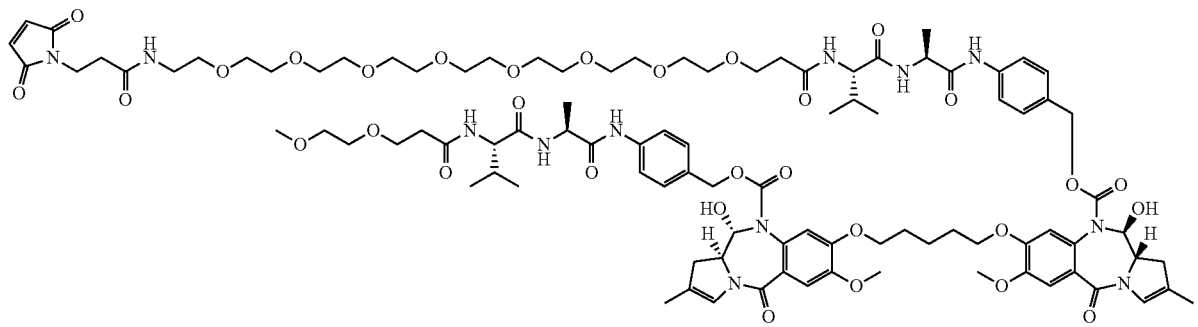 [SMILES: COCCOCCC(=O)N[C@H](C(=O)N[C@@H](C)C(=O)Nc1ccc(COC(=O)N2c3cc(OCCCCCOc4cc5c(cc4OC)C(=O)N4C=C(C)C[C@H]4[C@H](O)N5C(=O)OCc4ccc(NC(=O)[C@H](C)NC(=O)[C@@H](NC(=O)CCOCCOCCOCCOCCOCCOCCOCCOCCNC(=O)CCN5C(=O)C=CC5=O)C(C)C)cc4)c(OC)cc3C(=O)N3C=C(C)C[C@H]3[C@@H]2O)cc1)C(C)C]

Anti-ASCT2 antibodies and antigen fragments thereof, disclosed herein, can be conjugated to heterologous agents using site-specific or non-site specific methods of conjugation. In some aspects, the ADC comprises one, two, three, four or more therapeutic moieties. In some aspects, all therapeutic moieties are the same.

Conventional conjugation strategies for antibodies or antigen-binding fragments thereof rely on randomly conjugating the payload to the antibody or fragment through lysines or cysteines. Accordingly, in some aspects the antibody or antigen-binding fragment thereof is randomly conjugated to an agent, for example, by partial reduction of the antibody or fragment, followed by reaction with a desired agent, with or without a linker moiety attached. The antibody or fragment may be reduced using DTT or similar reducing agent. The agent with or without a linker moiety attached can then be added at a molar excess to the reduced antibody or fragment in the presence of DMSO. After conjugation, excess free cysteine may be added to quench unreacted agent. The reaction mixture may then be purified and buffer-exchanged into PBS.

In other aspects, site-specific conjugation of therapeutic moieties to antibodies using reactive amino acid residues at specific positions yields homogeneous ADC preparations with uniform stoichiometry. The site specific conjugation can be through a cysteine, residue or a non-natural amino acid. In one embodiment, the cytotoxic or imaging agent is conjugated to the antibody or antigen binding fragment thereof through at least one cysteine residue. In some aspects, each therapeutic moiety is chemically conjugated to the side chain of an amino acid at a specific Kabat position in the Fc region. In some embodiments, the cytotoxic or imaging agent is conjugated to the antibody or antigen binding fragment thereof through a cysteine substitution of at least one of positions 239, 248, 254, 273, 279, 282, 284, 286, 287, 289, 297, 298, 312, 324, 326, 330, 335, 337, 339, 350, 355, 356, 359, 360, 361, 375, 383, 384, 389, 398, 400, 413, 415, 418, 422, 440, 441, 442, 443 and 446, wherein the numbering corresponds to the EU index in Kabat. In some aspects, the specific Kabat positions are 239, 442, or both. In some aspects, the specific positions are Kabat position 442, an amino acid insertion between Kabat positions 239 and 240, or both. In some aspects, the agent is conjugated to the antibody or antigen binding fragment thereof through a thiol-maleimide linkage. In some aspects, the amino acid side chain is a sulfhydryl side chain.

In one embodiment, the ASCT2-binding molecule, e.g., an ASCT2-ADC, an anti-ASCT2 antibody, or antigen-binding fragment thereof, delivers a cytotoxic payload to ASCT2-expressing cells and inhibit or suppress proliferation by at least 10%, or at least 20%, or at least 30%, or at least 40%, or at least 50%, or at least 60%, or at least 70%, or at least 80%, or at least 90% or about 100%. Cellular proliferation can be assayed using art recognized techniques which measure rate of cell division, and/or the fraction of cells within a cell population undergoing cell division, and/or rate of cell loss from a cell population due to terminal differentiation or cell death (e.g., thymidine incorporation).

VI. Polynucleotides Encoding Asct2-Binding Molecules and Expression Thereof

This disclosure provides polynucleotides comprising nucleic acid sequences that encode a polypeptide that specifically binds ASCT2 or an antigen-binding fragment thereof. For example, the invention provides a polynucleotide comprising a nucleic acid sequence that encodes an anti-ASCT2 antibody or encodes an antigen-binding fragment of such an antibody. The polynucleotides of the invention can be in the form of RNA or in the form of DNA.

DNA includes cDNA, genomic DNA, and synthetic DNA; and can be double-stranded or single-stranded, and if single stranded can be the coding strand or non-coding (anti-sense) strand.

In certain embodiments, a polynucleotide can be isolated. In certain embodiments, a polynucleotide can be substantially pure. In certain embodiments, a polynucleotide can be cDNA or are derived from cDNA. In certain embodiments, a polynucleotide can be recombinantly produced. In certain embodiments, a polynucleotide can comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a pre-protein and can have the leader sequence cleaved by the host cell to form the mature form of the polypeptide. The polynucleotides can also encode an ASCT2-binding pro-protein which is the mature protein plus additional 5' amino acid residues.

The disclosure further provides an isolated polynucleotide comprising a nucleic acid encoding an antibody VH, wherein the VH comprises an amino acid sequence at least 70%, 75%, 80%, 85%, 90%, 95%, or 100% identical to a reference amino acid sequence selected from the group consisting of SEQ ID NO: 1, SEQ ID NO: 3, SEQ ID NO: 5, and SEQ ID NO: 7.

Moreover, the disclosure provides an isolated polynucleotide comprising a nucleic acid encoding an antibody VL, wherein the VL comprises an amino acid sequence at least 70%, 75%, 80%, 85%, 90%, 95%, or 100% identical to a reference amino acid sequence selected from the group consisting of SEQ ID NO: 2, SEQ ID NO: 4, SEQ ID NO: 6, and SEQ ID NO: 8.

In certain embodiments, the disclosure provides an isolated polynucleotide comprising a nucleic acid encoding an antibody VH, wherein the VH comprises an amino acid sequence at least 70%, 75%, 80%, 85%, 90%, 95%, or 100% identical to reference amino acid sequence SEQ ID NO: 1, and a nucleic acid encoding an antibody VL, wherein the VL comprises an amino acid sequence at least 70%, 75%, 80%, 85%, 90%, 95%, or 100% identical to reference amino acid sequence SEQ ID NO: 2. In certain embodiments, the disclosure provides an isolated polynucleotide comprising a nucleic acid encoding an antibody VH, wherein the VH comprises an amino acid sequence at least 70%, 75%, 80%, 85%, 90%, 95%, or 100% identical to reference amino acid sequence SEQ ID NO: 3, and a nucleic acid encoding an antibody VL, wherein the VL comprises an amino acid sequence at least 70%, 75%, 80%, 85%, 90%, 95%, or 100% identical to reference amino acid sequence SEQ ID NO: 4. In certain embodiments, the disclosure provides an isolated polynucleotide comprising a nucleic acid encoding an antibody VH, wherein the VH comprises an amino acid sequence at least 70%, 75%, 80%, 85%, 90%, 95%, or 100% identical to reference amino acid sequence SEQ ID NO: 5, and a nucleic acid encoding an antibody VL, wherein the VL comprises an amino acid sequence at least 70%, 75%, 80%, 85%, 90%, 95%, or 100% identical to reference amino acid sequence SEQ ID NO: 6. In certain embodiments, the disclosure provides an isolated polynucleotide comprising a nucleic acid encoding an antibody VH, wherein the VH comprises an amino acid sequence at least 70%, 75%, 80%, 85%, 90%, 95%, or 100% identical to reference amino acid sequence SEQ ID NO: 7, and a nucleic acid encoding an antibody VL, wherein the VL comprises an amino acid sequence at least 70%, 75%, 80%, 85%, 90%, 95%, or 100% identical to reference amino acid sequence SEQ ID NO: 8.

In certain aspects, an antibody or antigen-binding fragment thereof comprising a VH or VL encoded by a polynucleotide as described above, can specifically bind to ASCT2, e.g., human or cynomolgus monkey ASCT2. In certain cases such an antibody or antigen-binding fragment thereof can specifically bind to the same epitope as an antibody or antigen-binding fragment thereof comprising the VH and VL of 17c10 or 1e8. In certain aspects the disclosure provides a polynucleotide or combination of polynucleotides encoding a binding molecule, e.g., an antibody or antigen-binding fragment thereof, which specifically binds to ASCT2.

Further provided is a vector comprising a polynucleotide as described above. Suitable vectors are described herein and are known to those of ordinary skill in the art.

In certain aspects, the disclosure provides a composition, e.g., a pharmaceutical composition, comprising a polynucleotide or vector as described above, optionally further comprising one or more carriers, diluents, excipients, or other additives.

In a polynucleotide composition as described above, the polynucleotide comprising a nucleic acid encoding a VH and the polynucleotide comprising a nucleic acid encoding a VL can reside in a single vector, or can be on separate vectors. Accordingly the disclosure provides one or more vectors comprising the polynucleotide composition described above.

This disclosure further provides a host cell comprising a polynucleotide, polynucleotide composition, or vector as provided above, where host cell can, in some instances, express an antibody or antigen-binding fragment thereof that specifically binds to ASCT2. Such a host cell can be utilized in a method of making an antibody or antigen-binding fragment thereof as provided herein, where the method includes (a) culturing the host cell and (b) isolating the antibody or antigen-binding fragment thereof expressed from the host cell.

In certain embodiments the polynucleotides comprise the coding sequence for the mature ASCT2-binding polypeptide, e.g., an anti-ASCT2 antibody or an antigen-binding fragment thereof, fused in the same reading frame to a marker sequence that allows, for example, purification of the encoded polypeptide. For instance, the marker sequence can be a hexahistidine tag supplied by a pQE-9 vector to provide for purification of the mature polypeptide fused to the marker, in the case of a bacterial host, or the marker sequence can be a hemagglutinin (HA) tag derived from the influenza hemagglutinin protein when a mammalian host (e.g., COS-7 cells) is used.

Polynucleotide variants are also provided. Polynucleotide variants can contain alterations in the coding regions, non-coding regions, or both. In some embodiments polynucleotide variants contain alterations that produce silent substitutions, additions, or deletions, but do not alter the properties or activities of the encoded polypeptide. In some embodiments, polynucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*). Vectors and cells comprising the polynucleotides described herein are also provided.

In some embodiments a DNA sequence encoding an ASCT2-binding molecule can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular isolated polypeptide of interest can be inserted into an expression vector and operatively linked to an expression control sequence appropriate for expression of the protein in a desired host. Proper assembly can be confirmed, e.g., by nucleotide sequencing, restriction mapping, and/or expression of a biologically active polypeptide in a suitable host. In order to obtain high expression levels of a transfected gene in a host, the gene can be operatively linked to or associated with transcriptional and translational expression control sequences that are functional in the chosen expression host.

In certain embodiments, recombinant expression vectors are used to amplify and express DNA encoding anti-ASCT2 antibodies or antigen-binding fragments thereof. Recombinant expression vectors are replicable DNA constructs which have synthetic or cDNA-derived DNA fragments encoding a polypeptide chain of an anti-ASCT2 antibody or and antigen-binding fragment thereof, operatively linked to suitable transcriptional or translational regulatory elements derived from mammalian, microbial, viral, or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail herein. Such regulatory elements can include an operator sequence to control transcription. The ability to replicate in a host, usually conferred by an origin of replication, and a selection gene to facilitate recognition of transformants, can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where a recombinant protein is expressed without a leader or transport sequence, the protein can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR 1, pBR322, pMB9, and their derivatives, wider host range plasmids, such as M13, and filamentous single-stranded DNA phages.

Suitable host cells for expression of an ASCT2-binding molecule include prokaryotes, yeast, insect, or higher eukaryotic cells, under the control of appropriate promoters. Prokaryotes include gram negative or gram positive organisms, for example *E. coli* or bacilli. Higher eukaryotic cells include established cell lines of mammalian origin as described herein. Cell-free translation systems can also be employed. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems can also be advantageously employed to express recombinant ASCT2-binding molecules. Expression of recombinant proteins in mammalian cells can be performed because such proteins are generally correctly folded, appropriately modified, and completely functional. Examples of suitable mammalian host cell lines include HEK-293 and HEK-293T, the COS-7 lines of monkey kidney cells, described by Gluzman, *Cell* 23:175 (1981), and other cell lines including, for example, L cells, C127, 3T3, Chinese hamster ovary (CHO), HeLa, and BHK cell lines. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *BioTechnology* 6:47 (1988).

ASCT2-binding molecules produced by a transformed host can be purified according to any suitable method. Such standard methods include chromatography (e.g., ion exchange, affinity, and sizing column chromatography), centrifugation, differential solubility, or by any other standard technique for protein purification. Affinity tags, such as hexahistidine, maltose binding domain, influenza coat sequence, and glutathione-S-transferase, can be attached to the protein to allow easy purification by passage over an appropriate affinity column. Isolated proteins can also be physically characterized using such techniques as proteolysis, nuclear magnetic resonance and x-ray crystallography.

For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose, or other types commonly employed in protein purification. Alternatively, a cation exchange step can be employed. Suitable cation exchangers include various insoluble matrices comprising sulfopropyl or carboxymethyl groups. Finally, one or more reverse-phase high performance liquid chromatography (RP-HPLC) steps employing hydrophobic RP-HPLC media, e.g., silica gel having pendant methyl or other aliphatic groups, can be employed to further purify an ASCT2-binding molecule. Some or all of the foregoing purification steps, in various combinations, can also be employed to provide a homogeneous recombinant protein.

A recombinant ASCT2-binding molecule produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

VII. Pharmaceutical Compositions and Administration Methods

Methods of preparing and administering the ASCT2-binding molecules provided herein to a subject in need thereof are well known to or are readily determined by those skilled in the art. The route of administration of the ASCT2-binding molecule can be, for example, oral, parenteral, by inhalation, or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, another example of a form for administration would be a solution for injection, in particular for intravenous or intraarterial injection or drip. Usually, a suitable pharmaceutical composition can comprise a buffer (e.g., acetate, phosphate or citrate buffer), a surfactant (e.g., polysorbate), optionally a stabilizer agent (e.g., human albumin), etc. In other methods compatible with the teachings herein, ASCT2-binding molecules provided herein can be delivered directly to the site of the adverse cellular population thereby increasing the exposure of the diseased tissue to the therapeutic agent. In one embodiment, the administration is directly to the airway, e.g., by inhalation or intranasal administration.

As discussed herein, ASCT2-binding molecules provided herein can be administered in a pharmaceutically effective amount for the in vivo treatment of diseases or disorders characterized by ASCT2 overexpression, such as colorectal cancer, HNSCC, prostate cancer, lung cancer, pancreatic cancer, melanoma, endometrial cancer, hematological cancer (AML, MM, DLBCL), and cancers comprising CSCs. In this regard, it will be appreciated that the disclosed binding molecules can be formulated so as to facilitate administration and promote stability of the active agent. Pharmaceutical compositions in accordance with the present invention can comprise a pharmaceutically acceptable, non-toxic, sterile carrier such as physiological saline, non-toxic buffers, preservatives and the like. For the purposes of the instant application, a pharmaceutically effective amount of an ASCT2-binding molecule means an amount sufficient to achieve effective binding to a target and to achieve a benefit, e.g., to ameliorate symptoms of a disease or condition or to detect a substance or a cell. Suitable formulations for use in the therapeutic methods disclosed herein are described in Remington's Pharmaceutical Sciences, 22nd ed., Ed. Lloyd V. Allen, Jr. (2012).

Certain pharmaceutical compositions provided herein can be orally administered in an acceptable dosage form including, e.g., capsules, tablets, aqueous suspensions, or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an ASCT2-binding molecule that can be combined with carrier materials to produce a single dosage form will vary depending upon the subject treated and the particular mode of administration. The composition can be administered as a single dose, multiple doses or over an established period of time in an infusion. Dosage regimens also can be adjusted to provide the optimum desired response.

In keeping with the scope of the present disclosure, ASCT2-binding molecules can be administered to a human or other animal in accordance with the aforementioned methods of treatment in an amount sufficient to produce a therapeutic effect. The ASCT2-binding molecules provided herein can be administered to such human or other animal in a conventional dosage form prepared by combining an ASCT2-binding molecule of the invention with a conventional pharmaceutically acceptable carrier or diluent according to known techniques. The form and character of the pharmaceutically acceptable carrier or diluent can be dictated by the amount of active ingredient with which it is to be combined, the route of administration and other well-known variables. A cocktail comprising one or more species of ASCT2-binding molecules, e.g., ASCT2-ADCs, anti-ASCT2 antibodies, or antigen-binding fragments, variants, or derivatives thereof, of the invention can also be used.

By "therapeutically effective dose or amount" or "effective amount" is intended an amount of an ASCT2-binding molecule that, when administered, brings about a positive therapeutic response with respect to treatment of a patient with a disease or condition to be treated.

Therapeutically effective doses of the compositions of the present invention, for treatment of diseases or disorders in which ASCT2 is overexpressed, such as certain cancers, vary depending upon many different factors, including means of administration, target site, physiological state of the patient, whether the patient is human or an animal, and other medications administered. Usually, the patient is a human, but non-human mammals, including transgenic mammals, can also be treated. Treatment dosages can be titrated using routine methods known to those of skill in the art to optimize safety and efficacy.

The amount of at least one ASCT2-binding molecule to be administered is readily determined by one of ordinary skill in the art without undue experimentation given this disclosure. Factors influencing the mode of administration and the respective amount of at least one ASCT2-binding molecule include, but are not limited to, the severity of the disease, the history of the disease, and the age, height, weight, health, and physical condition of the individual undergoing therapy. Similarly, the amount of an ASCT2-binding molecule to be administered will be dependent upon the mode of administration and whether the subject will undergo a single dose or multiple doses of this agent.

This disclosure also provides for the use of an ASCT2-binding molecule, e.g., an ASCT2-ADC, an anti-ASCT2 antibody, or antigen-binding fragment, variant, or derivative thereof, for use in the treatment of a disease or disorder characterized by ASCT2 overexpression, e.g., colorectal cancer, HNSCC, prostate cancer, lung cancer, pancreatic cancer, or a hematological cancer.

This disclosure also provides for the use of an ASCT2-binding molecule, e.g., an ASCT2-ADC, an anti-ASCT2 antibody or antigen-binding fragment, variant, or derivative thereof, in the manufacture of a medicament for treating a disease or disorder characterized by ASCT2 overexpression, e.g., colorectal cancer, HNSCC, prostate cancer, lung cancer, pancreatic cancer, or a hematological cancer.

VIII. Diagnostics

This disclosure further provides a diagnostic method useful during diagnosis of diseases characterized by ASCT2-overexpression, such as certain cancers, which involves measuring the expression level of ASCT2 in cells or tissue from an individual and comparing the measured expression level with a standard ASCT2 expression in normal cells or tissue, whereby an increase in the expression level compared to the standard is indicative of a disorder treatable by an ASCT2-binding molecule provided herein.

The ASCT2-binding molecules provided herein can be used to assay ASCT2 protein levels in a biological sample using classical immunohistological methods known to those of skill in the art. See Jalkanen et al., *J. Cell Biol.* 105:3087-3096 (1987); Jalkanen, et al., *J. Cell. Biol.* 101:976-985 (1985). Other antibody-based methods useful for detecting ASCT2 protein expression include immunoassays, such as ELISA, immunoprecipitation, or Western blotting.

By "assaying the expression level of ASCT2 polypeptide" is intended qualitatively or quantitatively measuring or estimating the level of ASCT2 polypeptide in a first biological sample either directly (e.g., by determining or estimating absolute protein level) or relatively (e.g., by comparing to the disease associated polypeptide level in a second biological sample). The ASCT2 polypeptide expression level in the first biological sample can be measured or estimated and compared to a standard ASCT2 polypeptide level, the standard being taken from a second biological sample obtained from an individual not having the disorder, or being determined by averaging levels from a population of individuals not having the disorder. As will be appreciated in the art, once the "standard" ASCT2 polypeptide level is known, it can be used repeatedly as a standard for comparison.

By "biological sample" is intended any biological sample obtained from an individual, cell line, tissue culture, or other source of cells potentially expressing ASCT2. Methods for obtaining tissue biopsies and body fluids from mammals are well known in the art.

IX. Kits Comprising Asct2-Binding Molecules

This disclosure further provides kits that comprise an ASCT2-binding molecule described herein and that can be used to perform the methods described herein. In certain embodiments, a kit comprises at least one purified anti-ASCT2 antibody or an antigen-binding fragment thereof in one or more containers. In some embodiments, a kit comprises at least one purified ASCT2-ADC in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed ASCT2-binding molecules can be readily incorporated into one of the established kit formats which are well known in the art.

X. Immunoassays

ASCT2-binding molecules provided herein can be used in assays for immunospecific binding by any method known in the art. The immunoassays that can be used include, but are not limited to, competitive and non-competitive assay systems using techniques such as Western blot, RIA, ELISA, ELISPOT, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art. See, e.g., Ausubel et al., eds, (1994) Current Protocols in Molecular Biology (John Wiley & Sons, Inc., NY) Vol. 1, which is incorporated by reference herein in its entirety.

ASCT2-binding molecules provided herein can be employed histologically, as in immunofluorescence, immunoelectron microscopy, or non-immunological assays, for example, for in situ detection of ASCT2 or conserved variants or peptide fragments thereof. In situ detection can be accomplished by removing a histological specimen from a patient, and applying thereto a labeled ASCT2-binding molecule, e.g., applied by overlaying the labeled ASCT2-binding molecule onto a biological sample. Through the use of such a procedure, it is possible to determine not only the presence of ASCT2, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

The binding activity of a given lot of an ASCT2-binding molecule can be determined according to well-known methods. Those skilled in the art will be able to determine operative and optimal assay conditions for each determination by employing routine experimentation.

Methods and reagents suitable for determination of binding characteristics of an isolated ASCT2-binding molecule are known in the art and/or are commercially available. Equipment and software designed for such kinetic analyses are commercially available (e.g., BIAcore®, BIAevaluation® software, GE Healthcare; KINEXA® Software, Sapidyne Instruments).

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited in this disclosure are hereby incorporated by reference in their entireties. In addition, any manufacturer's instructions or catalogues for any products cited or mentioned herein are incorporated by reference. Documents incorporated by reference into this text, or any teachings therein, can be used in the practice of the present invention. Documents incorporated by reference into this text are not admitted to be prior art.

XI. Embodiments

Embodiment 1

An antibody or antigen-binding fragment thereof, which specifically binds to an epitope of the neutral amino acid transporter 2 (ASCT2), wherein the antibody or antigen-binding fragment specifically binds to the same ASCT2 epitope as an antibody or antigen-binding fragment thereof comprising three heavy chain complementarity determining regions (HCDRs) of a heavy chain variable region (VH) and three light chain complementarity determining regions (LCDRs) of a light chain variable region (VL); wherein the amino acid sequence of HCDR1 is set forth in SEQ ID NO: 10; the amino acid sequence of HCDR2 is set forth in SEQ ID NO: 22; the amino acid sequence of HCDR3 is set forth in SEQ ID NO: 23; the amino acid sequence of LCDR1 is set forth in SEQ ID NO: 13; the amino acid sequence of LCDR2 is set forth in SEQ ID NO: 24; and the amino acid sequence of LCDR3 is set forth in SEQ ID NO: 25.

Embodiment 2

The antibody or antigen binding fragment of embodiment 1, wherein the antibody or antigen-binding fragment thereof comprises an HCDR1 of the amino acid sequence of SEQ ID NO: 10 or SEQ ID NO: 16; an HCDR2 of the amino acid sequence of SEQ ID NO: 11 or SEQ ID NO: 17; an HCDR3 of the amino acid sequence of SEQ ID NO: 12 or SEQ ID NO: 18; an LCDR1 of the amino acid sequence of SEQ ID NO: 13 or SEQ ID NO: 19; an LCDR2 of the amino acid sequence of SEQ ID NO: 14 or SEQ ID NO: 20; and an LCDR3 of the amino acid sequence of SEQ ID NO: 15 or SEQ ID NO: 21.

Embodiment 3

The antibody or antigen binding fragment of any of embodiment 1 or embodiment 2, wherein the VH comprises an amino acid sequence selected from SEQ ID NO: 1; SEQ ID NO: 3; SEQ ID NO: 5; and SEQ ID NO: 7, and wherein the VL comprises an amino acid sequence selected from SEQ ID NO: 2; SEQ ID NO: 4; SEQ ID NO: 6; and SEQ ID NO: 8.

Embodiment 4

The antibody or antigen-binding fragment according to any one of embodiments 1 to 3, wherein the VH comprises the amino acid sequence of SEQ ID NO: 5 and the VL comprises the amino acid sequence of SEQ ID NO: 6.

Embodiment 5

The antibody or antigen-binding fragment according to any one of embodiments 1 to 3, wherein the VH comprises the amino acid sequence SEQ ID NO: 7 and the VL comprises the amino acid sequence SEQ ID NO: 8.

Embodiment 6

The antibody or antigen-binding fragment according to any one of embodiments 1 to 5, wherein the IgG constant region comprises a cysteine (C) insertion between the serine (S) at position 239 and the V at position 240.

Embodiment 7

The antibody or antigen binding fragment according to embodiment 6, wherein the antibody comprises a heavy chain of an amino acid sequence of SEQ ID NO: 9.

Embodiment 8

The antibody or antigen binding fragment according to any one of embodiments 1 to 7, wherein upon the antibody binding to ASCT2 on the cell surface, the antibody internalizes into the cell.

Embodiment 9

The antibody or antigen-binding fragment according to any one of embodiments 1 to 8, which comprises a light chain constant region selected from the group consisting of a human kappa constant region and a human lambda constant region.

Embodiment 10

The antibody or antigen binding fragment according to embodiment 9, wherein the antibody comprises a human kappa constant region of SEQ ID NO: 26.

Embodiment 11

The antibody or antigen-binding fragment according to any one of embodiments 1 to 10, further conjugated to a cytotoxin selected from the group consisting of an antimicrobial agent, a therapeutic agent, a prodrug, a peptide, a protein, an enzyme, a lipid, a biological response modifier, a pharmaceutical agent, a lymphokine, a heterologous antibody, a fragment of a heterologous antibody, a detectable label, a polyethylene glycol (PEG), a radioisotope, and a combination of two or more of any said cytotoxins.

Embodiment 12

The antibody or antigen-binding fragment according to embodiment 11, which is conjugated to a cytotoxin.

Embodiment 13

The antibody or antigen binding fragment according to embodiment 12, wherein the cytotoxin is selected from a tubulysin derivative and a pyrrolobenzodiazepine.

Embodiment 14

The antibody or antigen binding fragment according to embodiment 13, wherein the tubulysin derivative is tubulysin AZ1508.

Embodiment 15

The antibody or antigen binding fragment according to embodiment 13, wherein the pyrrolobenzodiapezine is selected from SG3315 and SG3249.

Embodiment 16

The antibody or antigen binding fragment according to embodiment 15, wherein the pyrrolobenzodiapezine is SG3315.

Embodiment 16A

The antibody or antigen binding fragment according to embodiment 15, wherein the pyrrolobenzodiapezine is SG3249.

Embodiment 17

The antibody or antigen-binding fragment according to any one of embodiments 1 to 16, wherein the antibody binds to human ASCT2 and cynomolgus monkey ASCT2.

Embodiment 18

The antibody or antigen-binding fragment according to any one of embodiments 1 to 17, wherein the antibody does not specifically bind to human ASCT1.

Embodiment 19

A pharmaceutical composition comprising an antibody or antigen binding fragment of any one of embodiments 1 to 18 and a pharmaceutically acceptable carrier.

Embodiment 20

A polynucleotide or combination of polynucleotides encoding the antibody or antigen-binding fragment thereof according to any one of embodiments 1 to 19.

Embodiment 21

A vector comprising the polynucleotide or combination of polynucleotides according to embodiment 20.

Embodiment 22

A host cell comprising the polynucleotide or combination of polynucleotides according to claim 20 or the vector according to embodiment 21.

Embodiment 23

An antibody or antigen-binding fragment thereof, wherein the antibody or antigen-binding fragment comprises an HCDR1 of an amino acid sequence of SEQ ID NO: 10; an HCDR2 of an amino acid sequence of SEQ ID NO: 22; an HCDR3 of an amino acid sequence of SEQ ID NO: 23; an LCDR1 of an amino acid sequence of SEQ ID NO: 13; an LCDR2 of an amino acid sequence of SEQ ID NO: 24; and an LCDR3 of an amino acid sequence of SEQ ID NO: 23, and wherein the antibody or antigen-binding fragment is conjugated to a cytotoxin.

Embodiment 23A

An antibody or antigen-binding fragment thereof, wherein the antibody or antigen-binding fragment comprises an HCDR1 of an amino acid sequence of SEQ ID NO: 10; an HCDR2 of an amino acid sequence of SEQ ID NO: 22; an HCDR3 of an amino acid sequence of SEQ ID NO: 23; an LCDR1 of an amino acid sequence of SEQ ID NO: 13; an LCDR2 of an amino acid sequence of SEQ ID NO: 24; and an LCDR3 of an amino acid sequence of SEQ ID NO: 25, and wherein the antibody or antigen-binding fragment is conjugated to a cytotoxin.

Embodiment 24

The antibody or antigen-binding fragment thereof according to embodiment 23, wherein the antibody or antigen-binding fragment comprises a VH domain comprising the amino acid sequence SEQ ID NO: 7 and a VL domain comprising the amino acid sequence SEQ ID NO: 8.

Embodiment 24A

The antibody or antigen-binding fragment thereof according to embodiment 23, wherein the antibody or antigen-binding fragment comprises a VH domain comprising the amino acid sequence SEQ ID NO: 5 and a VL domain comprising the amino acid sequence SEQ ID NO: 6.

Embodiment 25

The antibody or antigen-binding fragment according to embodiment 23 or embodiment 24, wherein the cytotoxin is selected from the group consisting of an antimicrobial agent, a therapeutic agent, a prodrug, a peptide, a protein, an enzyme, a lipid, a biological response modifier, a pharmaceutical agent, a lymphokine, a heterologous antibody, a fragment of a heterologous antibody, a detectable label, a polyethylene glycol (PEG), a radioisotope, and a combination of two or more of any said cytotoxins.

Embodiment 26

The antibody or antigen binding fragment according to embodiment 23 or embodiment 24, wherein the cytotoxin is selected from a tubulysin derivative and a pyrrolobenzodiazepine.

Embodiment 27

The antibody or antigen binding fragment according to embodiment 26, wherein the tubulysin derivative is tubulysin AZ1508.

Embodiment 28

The antibody or antigen binding fragment according to embodiment 26, wherein the pyrrolobenzodiapezine is selected from SG3315 and SG3249.

Embodiment 29

The antibody or antigen binding fragment according to embodiment 28, wherein the pyrrolobenzodiapezine is SG3315.

Embodiment 29A

The antibody or antigen binding fragment according to embodiment 28, wherein the pyrrolobenzodiapezine is SG3249.

Embodiment 30

A pharmaceutical composition comprising the antibody or antigen-binding fragment according to embodiments 23 to 29 and a pharmaceutically acceptable carrier.

Embodiment 31

A method of making an antibody or antigen-binding fragment thereof, the method comprising culturing the host cell of embodiment 22; and isolating the antibody or antigen-binding fragment.

Embodiment 32

A diagnostic reagent comprising the antibody or antigen-binding fragment according to any one of embodiments 1 to 18 or 23 to 29.

Embodiment 33

A kit comprising the antibody or antigen-binding fragment according to any one of embodiments 1 to 18 or 23 to 29, or the composition according to embodiment 19 or 30.

Embodiment 34

A method of delivering an agent to an ASCT2-expressing cell, the method comprising contacting the cell with the antibody or antigen-binding fragment according to any one of embodiments 23 to 29, wherein the agent is internalized by the cell.

Embodiment 35

A method of inducing death of an ASCT2-expressing cell, the method comprising contacting the cell with the antibody or antigen-binding fragment according to any one of embodiments 23 to 29 wherein the antibody conjugated to the cytotoxin induces death of the ASCT2-expressing cell.

Embodiment 36

A method of treating a cancer characterized by overexpression of ASCT2 in a subject, the method comprising administering to a subject in need of treatment an effective amount of the antibody or antigen-binding fragment according to any one of embodiments 1 to 18 or 23 to 29, or the composition according to embodiment 19 or embodiment 30.

Embodiment 37

The method according to embodiment 36, wherein the cancer is selected from the group consisting of colorectal cancer, head and neck squamous cell carcinoma (HNSCC), prostate cancer, lung cancer, pancreatic cancer, melanoma, endometrial cancer, and hematological cancer (AML, MM, DLBCL).

Embodiment 37A

The method according to embodiment 36, wherein the cancer comprises a CSC.

Embodiment 38

The method according to embodiment 37, wherein the hematological cancer is selected from acute lymphoblastic leukemia (ALL); acute myelogenous leukemia (AML); chronic lymphocytic leukemia (CLL); chronic myelogenous leukemia (CML); acute monocytic leukemia (AMoL); Hodgkin's lymphomas; non-Hodgkin's lymphoma; and multiple myeloma.

Embodiment 39

A method for detecting ASCT2 expression level in a sample, the method comprising: contacting the sample with the antibody or antigen-binding fragment thereof according to any one of embodiments 1 to 18 or 23 to 29, or the composition according to embodiment 19 or embodiment 30, and detecting binding of the antibody or antigen-binding fragment thereof to ASCT2 in the sample.

Embodiment 40

The method according to embodiment 39, wherein the sample is a cell culture.

Embodiment 41

The method according to embodiment 39, wherein the sample is an isolated tissue.

Embodiment 42

The method according to embodiment 39, wherein the sample is from a human.

Embodiment 43

An ASCT2 antibody-drug conjugate (ASCT2-ADC) comprising an antibody or antigen-binding fragment thereof comprising an HCDR1 of the amino acid sequence of SEQ ID NO: 10; an HCDR2 of the amino acid sequence of SEQ ID NO: 11; an HCDR3 of the amino acid sequence of SEQ ID NO: 12, an LCDR1 of an amino acid sequence of SEQ ID NO: 13; an LCDR2 of an amino acid sequence of SEQ ID NO: 14; an LCDR3 of an amino acid sequence of SEQ ID NO: 15, and tubulysin AZ1508.

Embodiment 44

An ASCT2-ADC comprising an antibody or antigen-binding fragment thereof comprising an HCDR1 of the amino acid sequence of SEQ ID NO: 10; an HCDR2 of the amino acid sequence of SEQ ID NO: 11; an HCDR3 of the amino acid sequence of SEQ ID NO: 12; an LCDR1 of an amino acid sequence of SEQ ID NO: 13; an LCDR2 of an amino acid sequence of SEQ ID NO: 14; an LCDR3 of an amino acid sequence of SEQ ID NO: 15, and PBD SG3249.

Embodiment 45

An ASCT2-ADC comprising an antibody or antigen-binding fragment thereof comprising an HCDR1 of the amino acid sequence of SEQ ID NO: 10; an HCDR2 of the amino acid sequence of SEQ ID NO: 11; an HCDR3 of the amino acid sequence of SEQ ID NO: 12; an LCDR1 of an amino acid sequence of SEQ ID NO: 13; an LCDR2 of an amino acid sequence of SEQ ID NO: 14; an LCDR3 of an amino acid sequence of SEQ ID NO: 15, and tubulysin, and PBD SG3315.

Embodiment 46

An ASCT2-ADC comprising an antibody or antigen-binding fragment thereof comprising an HCDR1 of an amino acid sequence of SEQ ID NO: 16; an HCDR2 of an amino acid sequence of SEQ ID NO: 17; an HCDR3 of an amino acid sequence of SEQ ID NO: 18; an LCDR1 of an amino acid sequence of SEQ ID NO: 19; an LCDR2 of an amino acid sequence of SEQ ID NO: 20; and an LCDR3 of an amino acid sequence of SEQ ID NO: 21, and tubulysin AZ1508.

Embodiment 47

An ASCT2-ADC comprising an antibody or antigen-binding fragment thereof comprising an HCDR1 of an amino acid sequence of SEQ ID NO: 16; an HCDR2 of an amino acid sequence of SEQ ID NO: 17; an HCDR3 of an amino acid sequence of SEQ ID NO: 18; an LCDR1 of an amino acid sequence of SEQ ID NO: 19; an LCDR2 of an amino acid sequence of SEQ ID NO: 20; and an LCDR3 of an amino acid sequence of SEQ ID NO: 21, and PBD SG3249.

Embodiment 48

An ASCT2-ADC comprising an antibody or antigen-binding fragment thereof comprising an HCDR1 of an amino acid sequence of SEQ ID NO: 16; an HCDR2 of an amino acid sequence of SEQ ID NO: 17; an HCDR3 of an amino acid sequence of SEQ ID NO: 18; an LCDR1 of an amino acid sequence of SEQ ID NO: 19; an LCDR2 of an amino acid sequence of SEQ ID NO: 20; and an LCDR3 of an amino acid sequence of SEQ ID NO: 21, and PBD SG3315.

EXAMPLES

The following Examples are offered by way of illustration and not by way of limitation.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

Example 1. ASCT2 Expression in Human Normal and Cancer Tissues

ASC72 Protein Expression in Normal and Tumor Issue Analyzed by IHC

To assess protein expression of ASCT2, IHC was carried out in sections from normal human and from human tumor formaldehyde-fixed tissues. Following antigen retrieval treatment with citrate buffer (pH=6.0), the tissues were tested with anti-ASCT2 rabbit polyclonal antibody (EMD Millipore, Billerica, Mass.; Cat # ABN73), following the manufacturer's protocol. Protocol optimization was performed using the HT29 cell line as a positive control, and primary human hepatocytes cells as a negative control.

In normal tissues, no staining for ASCT2 was observed on liver, heart, pneumocyes, glomeruli, and brain.

ASC72 Expression in Human Tumors

ASCT2 expression was evaluated by IHC across various cancerous tissues. Strong membraneous ASCT2 expression was observed in solid tumors including colon carcinoma, lung squamous cell carcinoma, head and neck cancer, and prostate cancer tissues, and in hematologic cancers such as AML, MM, and DLBCL. In addition, high ASCT2 expression was observed in ovarian endometrial cancer tissues and in melanoma tissues. Table 2, below, provides a summary of ASCT2 expression in human cancer tissues.

TABLE 2

| ASCT2 Expression in Human Tumors | | | | | | |
|---|---|---|---|---|---|---|
| | Total | Neg* | Low | Medium | High | Positive Core | Positive Rate (%) |
| Lung NSCLC SCC | 5 | 0 | 1 | 1 | 3 | 5 | 100 |
| Lung NSCLC Adenocarcinoma | 5 | 3 | 0 | 2 | 0 | 2 | 40 |
| Lung NSCLC Undifferentiated | 2 | 1 | 0 | 0 | 1 | 1 | 50 |
| Breast Invasive Ductal | 10 | 8 | 1 | 1 | 0 | 2 | 20 |
| Breast Invasive Lobular | 2 | 2 | 0 | 0 | 0 | 0 | 0 |
| Ovarian Serous and Serous-Papillary Adeno | 8 | 5 | 1 | 1 | 1 | 3 | 38 |
| Ovarian Endometroid | 4 | 1 | 0 | 0 | 3 | 3 | 75 |
| Colon | 11 | 0 | 1 | 3 | 7 | 11 | 100 |
| Melanoma (metastasis) | 11 | 4 | 2 | 2 | 3 | 7 | 64 |
| Prostate | 12 | 0 | 0 | 1 | 11 | 12 | 100 |
| Head & Neck | 10 | 0 | 1 | 2 | 7 | 10 | 100 |
| MM | 15 | 0 | 0 | 0 | 15 | 15 | 100 |
| AML | 16 | 0 | 4 | 0 | 12 | 16 | 100 |
| DLBCL | 128 | 6 | 20 | 32 | 70 | 122 | 95.3 |

ASCT2 expression was observed in cancer stem cells from AML and MM. ASCT2 in cancer stem cells was evaluated by flow cytometry using the ASCT2 antibody 17c10 conjugated with a fluorophore Alexa 647. The expression of ASCT2 in AML and MM patients was substantially higher than in normal bone marrow as described in FIG. 1A. By using flow cytometry sorting different subpopulations, such as $CD38^+$, $CD38^-$, $CD34^+$; $CD34^-$; $CD38^+$; and $CD34^+$; and $CD38^-$ and $CD34^-$, cells were isolated and their stem cell properties were further characterized by performing a clonogenic assay on each subpopulation. We found that only $CD38^+$, $CD34^+$ cells formed colonies which further corroborate the finding described in the literature (Lapidot T et al., Nature 1994; 367(6464):645-8; Bonnet D et al. Nat Med 1997; 3(7):730-7.). ASCT2 expression was evaluated in all the subpopulations described above. FIG. 1B describes the high ASCT2 expression in the leukemic stem cell population, namely $CD38^+$, $CD34^+$ population of AML patient samples. Likewise, ASCT2 expression is also high in the bulk or non-leukemic stem cell populations in AML as described in FIG. 1C. Furthermore, ASCT2 expression was also evaluated in CD138+, CD19− (plasma cells) and CD138−, CD19+ (stem cells) cells of MM tumors. Histograms in FIG. 1C suggest high ASCT2 expression in plasma cells compared to the stem cells of MM. The data supports ASCT2 expression was observed in bone marrow from AML and MM patient samples compared to bone marrow from normal donor. Moreover, ASCT2 is highly overexpressed in the leukemic stem cells (LSC) ($CD34^+$/$CD38^+$) of AML patient samples. Furthermore, $CD138^+$, $CD19^-$ cells also defined as MM plasma cells show higher expression of ASCT2 compared to stem cell population ($CD138^-$, $CD19^+$).

ASCT2 expression was also observed in cancer stem cells from pancreatic tumors. Pancreatic solid tumor fragments were digested with collagen III and single cell suspension was made. Dissociated cells were stained with the antibody against cell surface proteins, EpCAM, CD44, CD24, and with ASCT2 antibody described earlier. Cell surface protein signatures for pancreatic cancer stem cells have been well characterized. $EpCAM^+$ $CD44^+$ $CD24^+$ cells are defined as cancer stem cells in pancreatic tumors (Li, C et al. Cancer Res. 2007; 67:1030-1037). Example of ASCT2 expression in the CSC population (EpCAM+, CD44+, CD24+) is described FIG. 1D. Using this same strategy, ASCT2 expression was evaluated in the cancer stem cell populations of pancreatic tumors following a single dose treatment with ASCT2-PBD ADC or isotype control ADC. FIG. 1E demonstrates that ASCT2-PBD ADC ablates cancer stems cells populations. The data herein demonstrates targeting ASCT2 not only in solid tumors, but also in hematological cancers and cancer stem cells would be effective.

Example 2. Generation of Anti-ASCT2 Antibodies

Immunization and Hybridoma Generation

Antibodies to ASCT2 were generated by DNA immunization (Chowdhury et al., J. Immunol. Methods 249:147, 2001) of a plasmid harboring the human ASCT2 gene. The gene for human ASCT2 was cloned into expression plasmid pcDNA3.1 (Invitrogen, Carlsbad, Calif.). Eight-week old VelocImmune II mice (Regeneron, Tarrytown, N.Y.) were injected intradermally at the base of tail every other week with 100 µg of the ASCT2 expression plasmid at 1 mg/mL in PBS. Test bleeds were collected at 2-week intervals starting on day 28 after the first injection, and assayed for ASCT2-specific antibodies by flow cytometry. Serial dilutions of test bleeds were incubated with 293F cells expressing either ASCT2 or an irrelevant cell surface protein. At days 56 and 70, mice with the highest specific titers were sacrificed. Lymphocytes from lymph nodes and spleen were isolated, and fused with myeloma cell line P3x/63Ag8.653 at a 1:1 ratio following the polyethylene glycol (Roche Diagnostics, Indianapolis, Ind.) fusion method. Fused cells were selected in hypoxanthine-aminopterin-thymidine (HAT)-containing hybridoma growth media.

Flow Cytometry Screening Assay

Hybridoma supernatants were assessed for binding to HEK 293F cells expressing ASCT2. Supernatants that were found to bind specifically to ASCT2-expressing HEK 293F cells via flow cytometry were further confirmed for ASCT2-specific binding by flow cytometry staining with a panel of ASCT2-expressing cancer cell lines. Finally, the confirmed supernatants were converted into human IgG1s for further binding assessment.

Cloning and Expression of Human Anti-ASCT2 IgG mAbs and Fabs

Hybridomas were subcloned by limiting dilution. Supernatants of Protein A-affinity purified IgG subclones were screened for ASCT2-specific antibodies by flow cytometry as described above for the parental hybridomas. The mRNA of subcloned hybridomas was isolated using Dynabeads mRNA Direct Kit (Invitrogen). The first-strand of cDNA was synthesized using SuperScript III reverse transcriptase (Invitrogen) and random hexamer primers. Human Ig VL and VH genes were amplified by PCR with a set of Novagen® degenerate Ig-primers (EMD Millipore, Catalog #69830). The PCR-amplified VL and VH products were cloned into plasmid pCR2.1-TOPO (Invitrogen) and sequenced. The VH and VL genes from each hybridoma were re-amplified by PCR, adding restriction enzyme sites for cloning into human IgGkappa pOE vector, where VL was cloned at BssHII/BsiWI site fused with human c-kappa, and VH was cloned at BsrGI/SalI site fused with human IgG-1 heavy chain constant region (or CH1 region for Fab generation). The resulting pOE plasmids were verified by DNA sequencing.

Anti-ASCT2 antibodies were transiently expressed in either Hek293F (Invitrogen) or CHO-G22 cells. For expression in Hek293F cells, transfection was performed using 293fectin™ (Invitrogen; Cat. #12347-019) according to the manufacturer's protocol. The cells were cultured in FreeStyle™ 293 Expression Medium (Invitrogen; Cat. #12338-018), and the culture volume was doubled on days three and six post-transfection. Transfected Hek293F cells were cultured for a total of eleven days. For expression in CHO-G22 cells, cells were transfected using 25 kDa linear Polyethylenimine (Polysciences, Warrington, Pa.) using the manufacturer's protocol. The cells were cultured in CD CHO medium (Invitrogen), and fed every other day with an in-house feed. Transfected CHO-G22 cells were cultured for a total of twelve days.

After full length human IgGs were isolated by protein A chromatography, binding was reassessed via flow cytometry. FIG. 2 depicts a bar graph showing the fold change in binding of the isolated human IgGs 1e8, 3f7, 5a2, 9b3, 10c3, 16b8, 17c10, and 17a10 to cells expressing human ASCT2 as compared to mock transfected cells. As seen in the figure, several of the full length human IgGs were found to retain ASCT2 binding activity.

Example 3. ASCT2-Binding Antibodies as Antibody-Drug Conjugates (ADCs)

Assessing ADC-Mediated Cytotoxicity of ASCT2-Binding Antibodies

To confirm the internalization of parental antibodies, and to predict whether they can deliver a cytotoxic payload, the parental antibodies were tested in the Hum-ZAP antibody internalization assay (Advanced Targeting Systems, San Diego, Calif.) according to manufacturer's instructions. Briefly, ASCT2-positive WiDr cells were plated in culture media at a density of 1,000 cells per well of tissue culture-treated 96-well plates and allowed to adhere overnight at 37° C./5% $CO_2$. To prepare test articles, each parental antibody was incubated with a secondary antibody (goat anti-human IgG) conjugated with the ribosome inactivating protein, saporin, for 30 minutes at room temperature to form a secondary conjugate. Serial dilutions of this secondary conjugate were then prepared and added to wells containing cells.

Following incubation at 37° C./5% $CO_2$ for 72 hours, the CellTiter-Glo® Luminescent Viability Assay (Promega, Madison, Wis.) was used to determine relative cytotoxicity. Briefly, CellTiter-Glo® reagent was added to each well and allowed to incubate for 10 minutes at room temperature with mild shaking. The absorbance of each sample was read at 560 nM using a Perkin Elmer EnVision® luminometer. The relative proliferation rate (%) of cells treated with the parental antibodies 1E8 or 17C10, an anti-ASCT2 antibody chemically linked to saporin (hIgG-saporin), or an isotype control chemically linked to saporin was compared with that the relative viability of untreated control cells. As shown in FIG. 3A, the relative cell proliferation rate was lower in cells treated with anti-ASCT2 antibodies not chemically linked to saporin than in those cells treated with saporin-conjugated antibodies.

Assessing ADC-Mediated Cytotoxicity of Classically Conjugated Anti-ASCT2 Antibodies with Tubulysin Payload In order to confirm ADC-mediated killing by anti-ASCT2 antibodies conjugated to a tubulysin payload, lead antibodies 1E8 and 17C10 were directly conjugated with a tubulysin class of toxin, and cytotoxic killing with the conjugated antibodies was tested on ASCT2-positive colon cancer cells. Briefly, SW48 cells were plated in culture media at a density of 1,000 cells per well of tissue culture-treated 96-well plates and allowed to adhere overnight at 37° C./5% $CO_2$. To prepare the test articles, each antibody (ASCT2 leads 1E8 and 17C10, and isotype control) conjugated with the tubulysin payload was serially diluted and added to the respective wells. Following incubation at 37° C./5% C02 for 72 hours, the CellTiter-Glo® Luminescent Viability Assay was used to determine relative cytotoxicity, as described above.

The percent cell viability was calculated by the following formula: (average luminescence of treated samples/average luminescence of control samples)×100. $IC_{50}$ values were determined using logistic non-linear regression analysis with GraphPad Prism software. FIG. 3B shows a graph of the cytotoxicity of anti-ASCT2 1 E8, anti-ASCT2 17C10, and isotype control R347 classically conjugated to tubulysin AZ1508. The figure shows that both anti-ASCT2 antibodies have similar cytotoxicity. The calculated $IC_{50}$ values are shown in Table 3, below.

TABLE 3

ADC-Mediated Cytotoxic Killing by ASCT2 Lead Antibodies Classically Conjugated to tubulysin

| Antibody Clone | 17c10 | 1e8 | R347 |
|---|---|---|---|
| $IC_{50}$ (ng/ml) | 45.98 | 34.83 | NA |

Cloning of Cysteine Mutations for Site-Specific Conjugation

Standard overlapping PCR methods were used to introduce a cysteine residue between amino acid S239 and V240 in the CH2 region of the anti-ASCT2 antibodies 1E8 and 17C10. This cysteine, referred to as "239 insertion" or "239i," will serve as the site of conjugation for cytotoxic drugs in the preparation of anti-ASCT2 ADC antibodies. The amino acid sequence of the heavy chain backbone containing the Maia insertion is shown in SEQ ID NO: 9. Antibodies containing the introduced cysteine were conjugated to a tubulysin payload (tubulysin AZ1508) or to a pyrrolobenzodiazepine (PBD) payload (SG3249 or SG3315), essentially as described below.

Conjugation of Maleimide-Containing Drugs

All compounds evaluated for ADC payloads (AZ1508, SG3249, SG3315) contain a linker and a maleimide group that is readily conjugated to a thiol residue of an antibody, forming a thiol-maleimide linkage. Cytotoxins comprising a maleimide group (e.g., tubulysin 1508) may be conjugated to specific cysteine residues engineered into the anti-ASCT2 antibodies of the invention (e.g., 17c10, 1e8). Alternatively, or optionally, one may use classical conjugation methods to attach a cytotoxic agent to the antibodies described. Methods for conjugation of cytotoxins to native lysine and cysteine residues on antibodies are well known in the art. Representative methods for site-specific (at engineered cysteine residues) and classic conjugation (at native cysteine residues) are provided below.

A representative site-specific antibody-drug conjugation process includes the steps of (a) uncapping the size chains of the derivatizable amino acids (e.g., cysteines), (b) oxidizing, (c) conjugating a payload (e.g., a cytotoxic agent such as tubulysin 1508), and (d) polishing by removing conjugation reagents and non-reacted payload. For example, conjugation to an engineered cysteine may be carried out by formulating the antibody in 1×PBS with 1 mM ethylenediaminetetraacetic acid (EDTA). Mild reduction is used to generate free thiols by adding forty equivalences of tris(2-carboxyethyl)phosphine hydrochloride per antibody and incubating at 37° C. for three hours. Three successive dialyses in IX PBS with 1 mM EDTA were used to remove the tris(2-carboxyethyl)phosphine hydrochloride. Alternatively, desalting columns may be used to remove the tris(2-carboxyethyl)phosphine hydrochloride. The antibody interchain disulfide bonds were allowed to re-form by addition of about 20 equivalences of dehydroabietic acid (dhAA) and incubation for about four hours at room temperature.

In preparation for conjugation, dimethyl sulfoxide was added to the anti-ASCT2 antibody to ten percent v/v. Eight or twelve equivalences of the tubulysin 1508 payload (for 2T and 4T drug loading, respectively) in dimethyl sulfoxide was added, and the mixture incubated at room temperature for about 1 hour. Alternatively, the incubation can be done at 4° C. for about 16 hours. The reaction was quenched by adding about 4 molar equivalents of N-acteyl cysteine (NAC) per payload (i.e., 32 or 48). The free payload was removed from the conjugated antibody by using Ceramic Hydroxyapatite following the manufacturer's recommendations. If desired, the final product can be subjected to buffer-exchange. To confirm purity and conjugation to the heavy chain, the conjugated antibodies can be analyzed by any method known in the art. In some instances, non-reducing and reducing SDS-PAGE may be used to confirm purity and conjugation to the heavy chain.

ADCs with drugs randomly conjugated to native cysteine residues are prepared by partial reduction of the antibody followed by reaction with desired linker-drug. The antibody at a concentration of 5 mg/mL is partially reduced by addition of about 3 molar equivalents of DTT at pH 8.0, followed by incubation at about 37° C. for about 2 hours. The reduction reaction is then chilled in ice and the excess DTT is removed, for example, via diafiltration. The linker-drug is then added at a linker-drug/thiol molar ratio of about 1:10. The conjugation reaction is carried out in the presence of ~10% v/v of DMSO. After conjugation, excess free cysteine (about 2 fold molar ratio over linker-drug) is added to quench unreacted linker-drug to produce the cysteine-linker-drug adduct. The reaction mixture was purified (e.g., by hydrophobic interaction chromatography), and was be subjected to buffer-exchange into PBS. Drug load distribution was determined using standard methods, such as hydrophobic interaction chromatography and reduced reverse phase chromatography.

Example 4. Characterization of ASCT2-Binding mAbs and ADCs

ASC72 Specific Binding of ASCT2 Antibodies in Colorectal Cancer Cells

To determine whether binding of certain hybridoma clones was specific for the ASCT2 antigen, binding was assessed following shRNA knockdown of ASCT2 expression. Briefly, WiDr cells were transduced with lentivirus expressing ASCT2 shRNA or non-target shRNA (NT-shRNA). Binding of the two anti-ASCT2 hybridoma clones 17c10 and 1e8 was assessed at 72 hours post-infection. As seen in FIG. 4, knocking down of ASCT2 expression significantly ablated binding of the respective clones, and further confirmed the antigen-specific binding of ASCT2 mAbs 17c10 and 1e8.

Internalization Kinetics of Anti-ASCT2 Unconjugated Antibody

Internalization of the antibody upon binding with the target antigen is a prerequisite to achieving the desired ADC effect. Thus, internalization characteristics of ASCT2 antibodies were examined. WiDr cells were incubated with anti-ASCT2 antibody 17c10 conjugated to Alexa 488 (17c10-Alexa 488) for various periods of time. Cells were then washed and incubated with or without anti-Alexa 488 antibody for 45 minutes on ice to quench the cell surface signals. Fluorescence intensities of the total signal and the quenched signal (representing internalized antibody) were measured by flow cytometry analysis. As seen in FIG. 5A, anti-ASCT2 antibody 17c10 showed increased internalization with time compared to the isotype control antibody, which did not show internalization.

Internalization Kinetics of ASCT2-ADC (17c10AZ1508) Measured by Cytotoxic Killing Cells were pulsed with anti-ASCT2 antibody conjugated to tubulysin AZ1508 (17C10-AZ1508) for various time periods. Thereafter, ADC-containing medium was replaced with fresh medium and the cells further incubated for 4 days. Cell viability was measured by using CTG Kit. Dose-response curves were plotted as a percentage of untreated control cells and a representative graph is shown in FIG. 5B. The $IC_{50}$ values were calculated as described above, and the results are summarized in Table 4, below.

TABLE 4

Internalization Kinetics of ASCT2-ADC (17c10AZ1508)

| | $IC_{50}$ (ng/ml) | |
| --- | --- | --- |
| Time | 17c10 | 1e8 |
| 10 minutes | 410.9 | 963.6 |
| 30 minutes | 295.5 | 819.6 |
| 120 minutes | 100 | 317 |
| 8 hours | 29.04 | 110.9 |

Affinity Determination (Binding of 17c10 & 1e8 to ASCT2 Expressing Cell Lines)

Human, cynomolgous monkey, and CHO-derived cell lines expressing ASCT2 were utilized to assessed binding affinity and cross reactivity of ASCT2-specific antibodies. Apparent affinities were measured by titrating fluorophore labeled antibodies. Representative results are summarized in Table 6, below, and are shown in FIG. 6.

FIG. 6 shows flow cytometry plots resulting from binding of anti-ASCT2 antibodies 17c10 and 1e8, and isotype control R347 to ASCT2-expressing cell lines. Results for human cancer cell line Ca127 are shown in FIG. 6A; results for human cancer cell line FaDu are shown in FIG. 6B; results for human cancer cell line SSC 15 are shown in FIG. 6C; results for human cancer cell line WiDr are shown in FIG. 6D; results for CHOK1 cells stably expressing human ASCT2 are shown in FIG. 6E; results for CHOK1 cells stably expressing cyno ASCT2 are shown in FIG. 6F); results for cyno cancer cell line CynoMK1 are shown in FIG. 6G; and results for mock transfected CHOK1 cells are shown in FIG. 6H. The $EC_{50}$ values for 17c10 and 1e8 binding to ASCT2 expressing cell lines are indicated in Table 5, below.

TABLE 5

$EC_{50}$ Values for 17c10 and 1e8 Binding to ASCT2-Expressing Cell Lines

| Cell Line | 17c10 $EC_{50}$ (nM) | 1E8 $EC_{50}$ (nM) |
|---|---|---|
| Fadu | 3.8 | 6.8 |
| SSC15 | 3.6 | 8.8 |
| WiDr | 7.0 | 5.8 |
| Cal27 | 2.8 | 13 |
| Cyno MK1 | 6.7 | 14.8 |
| HuASCT2-CHOK1 | 8.6 | 8.1 |
| CynoASCT2-CHOK1 | 9.6 | 28.4 |

Specificity of 17c10 Antibody to ASCT2 Antigen

The anti-ASCT2 antibody 17c10 does not have affinity for ASCT1 (SLC1A4), the other member of the SLC1A family. Silencing of ASCT1 expression by shRNAs does not ablate ASCT2-specific binding of 17c10 in SKMEL-2 cells as is seen in the graph shown in FIG. 7A. Knockdown efficiency of shRNA was further confirmed by western blot analysis. Furthermore, no change was observed in the cytotoxicity profile of cells in which ASCT1 expression was silenced by respective shRNAs as is seen in the graph shown in FIG. 7B. Results are summarized in Table 6.

TABLE 6

ASCT2-Specific Binding and Cytotoxic Killing of 17c10-ADC

|  | NTshRNA | ASCT1-shRNA1 | ASCT1-shRNA2 | ASCT2-shRNA |
|---|---|---|---|---|
| $IC_{50}$ (ng/ml) | 14.34 | 7.59 | 4.96 | 205.4 |

Cross Reactivity & Cytotoxicity of ASCT2-ADC Antibodies to Cyno ASCT2

Anti-ASCT2-binding clones 17c10 and 1e8 conjugated to tubulysin AZ1508 were assessed for binding to cyno ASCT2 stably expressed in CHOK1 cells, human ASCT2 stably expressed in CHOK1 cells, and control molecules expressed in CHOK1 cells. ASCT2 antibody 17c10 (FIG. 8A) and ASCT2 antibody 1e8 (FIG. 8B), when conjugated to the tubulysin 1508 payload, show potent cytotoxic activity in CHOK1 cells expressing human and cyno ASCT2, but not in untransfected CHOK1 or CHOK1-ABCB5. These results are summarized in Table 7, below.

TABLE 7

ASCT2-Specific Binding and Cytotoxic Killing of 17c10-ADC

|  | Binding $EC_{50}$ (nM) | | Cytotoxicity $IC_{50}$ (ng/ml) | |
|---|---|---|---|---|
|  | 17C10 | 1e8 | 17C10 | 1e8 |
| HuASCT2 | 8.6 | 8.1 | 5.531 | 20.69 |
| CynoASCT2 | 9.6 | 28.4 | 8.59 | 140.3 |

Germlining of 17c10

The amino acid sequences of the VH and VL domains for 17c10 were aligned to the known human germline sequences in the VBASE database, and the closest germline was identified by sequence similarity. For the VH domain, this was IgVh4-34*01; for the VL domain, it was IgKv1-5*03. For 17c10, the germlining process involved reverting 1 framework residue in the VH domain and 5 residues in the VL domain. In the VH domain, the reversion mutation was at Kabat position 82a, where threonine (T) was reverted to serine (S). In the VL domain, the mutations were at Kabat position 13, 21, 39, 70, and 76 where at Kabat position 13 threonine (T) was reverted to alanine (A); at Kabat position 21 leucine (L) was reverted to isoleucine (I); at Kabat position 39 Asparagine (N) was reverted to lysine (K); at Kabat position 70 aspartate (D) was reverted to glutamate (E), and at Kabat position 76 threonine (T) was reverted to serine (S). These changes were made by synthesizing VH and VL domains with these mutations and replacing existing VH and VL using restriction digestion and ligation. Both the germlined and original (non-germlined) 17c10 were expressed as IgGs, and their affinity to multiple ASCT2-expressing cell lines was assessed by flow cytometry. As seen in FIG. 9A to FIG. 9D, there was no difference in binding of the germlined 17c10 or the parental 17c10 to WiDr cells, or to CHO cells expressing HuASCT2 or CyASCT2.

Example 5. Cytotoxic Killing by ASCT2-ADCs in Various Cancers

The 17c10 antibody was conjugated with a PBD (SG3315) or a Tubulysin (AZ1508) payload via a site-specific conjugation site, as described above. Drug-antibody ratio (DAR) was estimated to be about 2.0 for each asset. Cytotoxic assays were performed using cancer cells from various indications such as from pancreatic cancer, colon cancer, lung cancer, head and neck squamous carcinoma (HNSCC), prostate cancer, and an ASCT2 negative lung cancer. As shown in FIG. 10A to FIG. 10 F, the 17c10 ADC antibody conjugated to AZ1508 had higher cytotoxic activity than the control antibody bound to tubulysin. Anti-ASCT2 antibody 17c10 conjugated to SG3249 or SG3315 also had higher cytotoxic activity than control antibodies bound to tubulysin AZ1508, or bound to PBD SG3249, or bound to SG3315. A graph showing results from cytotoxic assays using 17c10 conjugated to SG3249 are shown in FIG. 11A, and a graph showing results from cytotoxic assays using 17c10 conjugated to SG3315 are shown in FIG. 11B. $IC_{50}$ values are summarized in Table 8, below.

TABLE 8

Inhibition of Cancer Cell Proliferation by ASCT2-ADCs

|  |  | $IC_{50}$ (ng/ml) | | |
|---|---|---|---|---|
| Indication | Cell line | 17c10-239i-AZ1508 | 17c10-239i-SG3315 | 17c10-239i-SG3249 |
| Colon | SW48 | 3.5 | 0.2 | 0.1 |
| Colon | HT29 | 2.5 | 2 | 1.8 |
| Colon | WiDR | 1.9 | 0.25 | 0.4 |
| Colon | DLD1 | 17.1 | 11.5 | 10.3 |
| Colon | HCT116 | 25.42 | 6.54 | 5.625 |
| HNSCC | OE21 | 4.94 | 11.26 | — |
| HNSCC | FADU | 82.7 | 17.5 | 15.88 |
| Lung-SSC | H2170 | 4.1 | 3.7 | 3.5 |
| Lung-SCLC | H69 | >1000 | 200 | 189.4 |
| Lung-SC | H2081 | — | — | — |
| Prostate | 22RV1 | 34.44 | 4.299 | — |
| Prostate | DU145 | 408.4 | 568.7 | — |
| Prostate | PC-3 | 13.43 | 21.94 | — |

TABLE 8-continued

Inhibition of Cancer Cell Proliferation by ASCT2-ADCs

| | | IC$_{50}$ (ng/ml) | | |
|---|---|---|---|---|
| Indication | Cell line | 17c10-239i-AZ1508 | 17c10-239i-SG3315 | 17c10-239i-SG3249 |
| Pancreatic cancer | BXPC3 | 7.85 | 3.28 | 2.98 |
| AML | HL60 | 47.41 | — | 9.796 |
| AML | KG1 | 37.72 | — | 64.25 |
| AML | MOLM-13 | 69.21 | — | 0.1001 |
| AML | Mv4-11 | 75 | — | 0.0515 |
| AML | Nomo-1 | 45 | — | 9.9 |
| AML | TF-1A | 5.57 | — | 0.17 |
| Burkitt's | Raji | 76.66 | — | 7.89 |
| MM | H929 | 14.9 | — | 0.6966 |
| MM | OPM-2 | 0.8 | — | 1.503 |

Example 6. ASCT2-ADCs Inhibit Tumor Growth In Vivo

All in vivo procedures were performed in accordance with institutional guidelines in an AAALAC-accredited facility and were approved by the MedImmune, LLC Institutional Animal Care and Use Committee. To test the ability of the ASCT2-ADC antibody to kill tumor cells, WiDr (100 µl/10$^6$ cells/mouse) or primary pancreatic tumors (PDX) were inoculated subcutaneously into the right flank of female 3-5 week old nude mice (Charles River Laboratories, Wilmington, Mass.). Mice were kept several weeks to develop tumors; once the tumors reached about 150-200 mm$^3$, mice were randomized and assigned to a treatment group (10 mice/group). Thereafter, mice were injected intravenously with different doses of anti-ASCT2 ADCs (17c10-Az1508 or 17c10-SG3315 or 17c10-SG3249) or an isotype control drug-conjugated antibody. Body weight and the tumor volume of the treated xenograft mice were monitored for the respective time periods. The tumor volume was calculated using the following formula: (shortest diameter)$^2$×(longest diameter)×0.5, and the results are shown in FIG. 12A, FIG. 12B, and FIG. 12C.

Additionally, in vivo efficacy of 17c10-SG3249 was evaluated in a panel of hematological malignancy models representing different subpopulations expressing varying level of ASCT2. ADCs were administered weekly at a dose of 0.4 mg/kg (or 0.5 mg/kg) and 0.1 mg/kg for a total of four doses in disseminated tumor xenograft models. Kaplan-Meier curves demonstrate a significant increase in survival benefit for the 17c10-SG3249 cohorts compared to untreated or isotype ADC controls as shown in FIG. 13A and FIG. 13B. Administration of 17c10-SG3249 in several AML xenograft tumor models showed substantial increase in survival benefit compared to the other cohorts such as, SOC, untreated and isotype control ADC. In TF1a AML models, 17c10-SG3249 demonstrated superior activity (median survival >205 days) compare to isotype control ADC (66 days). Similarly, 17c10-SG3249 demonstrated robust tumor growth inhibition and survival benefit in several MM1.S multiple myeloma (MM) models (median survival 123.5 days vs 55.5 days for untreated control). Results for 17c10-SG3249 in several hematological malignancies is summarized in the Table 9, below.

TABLE 9

Hematological Median Survival

| | | | Median Survival Time Days | | | | |
|---|---|---|---|---|---|---|---|
| | | | ASCT2-17C10-239i-SG3249 | | | | |
| Model | Untreated | Isotype ADC | 0.5 mg/kg | 0.4 mg/kg | 0.25 mg/kg | 0.1 mg/kg | 0.05 mg/kg |
| TF1a | 66 | 83 | >205** | | >205* | >205** | >205** |
| MM.1S | 55.5 | 63 | | 123.5*** | | 117*** | |
| RAJI | 16 | 17* | 49.5*** | | | 22*** | 19** |
| 697 | 20.5 | 22 | 68*** | | | 46*** | 36*** |

Statistical significance from untreated (Log-rank (mantel-Cox) test) - *= P < 0.0001, = P < 0.001, *= P < 0.01

Example 7. Conjugation Chemical Moieties to Anti-ASCT2 Antibodies to Form ADCs A purification method for the anti-ASCT2 mAbs was developed. Briefly, the harvested cell culture fluid was submitted to a protein A capture step performed using MAbSelect Sure resin (GE Healthcare) to capture the protein from the cell culture supernatant, and to remove process- and product related impurities. All process steps were performed at a linear flow rate of 300 cm/hr. The resin was equilibrated with 50 mM Tris, pH 7.4, and the conditioned medium was loaded onto the column to a load challenge of 30 g/L resin. The column was re-equilibrated with 50 mM Tris, pH 7.4, and then exposed to two wash steps optimized to reduce impurities and decrease the excess of light chain present in the conditioned medium. The first wash step consisted of 50 mM Tris, 500 mM sodium chloride, pH 7, and the second wash contained 50 mM sodium acetate, 500 mM sodium chloride, pH 5.0. The column was then re-equilibrated with 50 mM Tris, pH 7.4, and product was eluted with 25 mM sodium acetate, pH 3.6. Product was collected from 0.5 OD on the ascending side of the elution peak to 0.5 OD on the descending site. After each purification cycle, the column was stripped with 100 mM acetic acid, then re-equilibrated with 50 mM Tris, pH 7.4, sanitized with 0.1 N sodium hydroxide, and stored in 2% (v/v) benzyl alcohol, 100 mM sodium acetate, pH 5.0. Typical yield for this step is 70-75%.

Low pH treatment was performed for viral inactivation. Briefly, the MAbSelect Sure product was adjusted to a target pH of 3.5 by addition of 1 M acetic acid. After a hold time of 60 minutes, the solution was neutralized by addition of 1M Tris to a target pH of 7.4. The product was subsequently filtered.

As intermediate purification step, mixed mode chromatography was performed using resin Capto Adhere resin (GE Healthcare). This column was operated in flowthrough mode: The column is equilibrated with 50 mM Tris, pH 7.4, and the neutralized protein solution was loaded onto the column. Impurities bind to the resin, whereas the product is recovered in the flow through pool. Typical step yield was 80-84%.

The polishing step was performed using the cation exchange resin HS 50 (POROS). This step is performed in bind-elute mode and serves to further reduce process-related impurities. The column was equilibrated with 50 mM Tris, pH 7.4, and product from the mixed mode chromatography step was loaded onto the column. The column was subsequently washed with 50 mM Tris, pH 7.4, then with 50 mM Tris, 150 mM sodium chloride, pH 7.4, and then eluted with 50 mM Tris, 400 mM sodium chloride, pH 7.4. Product was collected from 0.5 OD on the ascending side of the elution peak to 0.5 OD on the descending side. After each purification cycle, the column was stripped using 50 mM Tris, 500 mM sodium chloride, pH 7.4, sanitized with 1N sodium hydroxide, and stored in 0.1 N NaOH. Typical yield for this step was 95-98%.

The purified mAb intermediate was concentrated using a Pellicon 3 Ultracel membrane with 30 kDa molecular weight cut off (MWCO) and transferred into formulation buffer (20 mM histidine, 240 mM sucrose pH 6.0) by diafiltration. Final protein concentration was about 20 mg/ml. If necessary, the protein was stored frozen at −80° C. until conjugation. Table 10, below, summarizes product quality during the monoclonal antibody purification process.

TABLE 10

Process Purity Over the Anti-ASCT2 Antibody Downstream Process

| Process step | Monomer Purity by HP SEC | HCP (ng/mg) | DNA (ng/mg) |
| --- | --- | --- | --- |
| MAb Select Sure | 98.0% | 2698 | 0.14 |
| Capto Adhere | 99.0% | 45 | 0.0004 |
| HS50 | 99.2% | 27 | 0.002 |

Conjugation of Anti-ASCT2 Antibody with Tubulysin AZ1508

The antibody-drug conjugate was prepared by site-directed conjugation of tubulysin (AZ1508) to the two free engineered cysteine residues via maleimide chemistry.

The purified mAb intermediate was thawed, and the pH adjusted to pH 7.0 by addition of 1 M Tris base. The protein solution was diluted to a final concentration of 7.5 mg/ml with 20 mM histidine buffer, pH 7.0, and EDTA added to a final concentration of 1 mM. The protein was transferred to a suitable reaction vessel, and the temperature adjusted to 37° C. The reducing agent tris(2-carboxyethyl)phosphine (TCEP) was added from a freshly prepared 50 mM stock solution at a molar ratio of TCEP:mAb=30:1. The solution was incubated with mild agitation at 37° C. for 3 hours. After this incubation time, the reducing agent was removed by dialysis or diafiltration against 20 mM histidine/1 mM EDTA buffer, pH 7.0. The recovered product was filtered through a 0.22 μm filter. For the oxidation, the protein solution was incubated with dehydroascorbic acid (DHA) at a molar ratio of 10:1 (DHA:mAb). Incubation was performed at 22-25° C. for 4 hours with mild agitation (at a 50 rpm mixing speed). After this time, the tubulysin payload (AZ1508) was added from a 10 mM stock solution in DMSO at a molar ratio of 8:1 payload:mAb. Additional DMSO was added dropwise to reach a final concentration of 10% (v/v). The mixture was incubated for 1 hour at 22-25° C. with mild agitation to allow the formation of antibody-drug conjugate. The reaction was then quenched by addition of N-acetylcysteine (NAC) from a 100 mM stock solution at a molar ratio of NAC:tubulysin of 5:1.

To remove protein fragments, aggregates, and the excess of free tubulysin payload, post-conjugation purification was performed using ceramic hydroxyapatite (CHT) type I (Biorad). The column was operated in bind-elute mode at a linear flow rate of 180 cm/hr. To the quenched antibody-drug-conjugate mixture, sodium phosphate was added to a final concentration of 10 mM from a 300 mM stock solution. The CHT column was pre-equilibrated with 300 mM sodium phosphate, pH 6.5, and equilibrated with 10 mM sodium phosphate, pH 6.5. The antibody-drug conjugate mixture was loaded up to a load challenge of 20 g/L, and the column was re-equilibrated with 10 mM sodium phosphate, pH 6.5. Elution was performed with a linear gradient to 1 M sodium chloride in 10 mM sodium phosphate, pH 6.5, over 10 column volumes. The elution peak was fractionated, and fractions were analyzed by HP SEC. Fractions containing conjugated protein with a monomer purity >95% were pooled. After each purification cycle, the column was stripped with 300 mM sodium phosphate, pH 6.5, sanitized with 1 N sodium hydroxide, and stored in 0.1 N sodium hydroxide.

The pooled antibody drug conjugate (ADC) was concentrated and exchanged into the final formulation buffer by tangential flow filtration using either regenerated cellulose or PES membranes with a 30 kDa MWCO. The excipient PS80 was spiked from a 10% stock solution. Final ADC concentration was 5 mg/ml in 20 mM histidine, 240 mM sucrose, 0.02% PS80, pH 6.0. Under these conditions, the generated ADC showed ≤12% unconjugated heavy chain, 75 to 82% monoconjugated heavy chain, and a drug-to-antibody ratio of 1.8-1.9.

Conjugation of Anti-ASCT2 Antibody with Pyrrolobenzodiazepine (PBD) SG3249

The antibody-drug conjugate was prepared by site-directed conjugation of PBD (SG3249) to the two free engineered cysteine residues via maleimide chemistry. Process sequence is the same as discussed for the tubulysin conjugation summarized above, although exact conditions differ.

The purified mAb intermediate was thawed, and the pH adjusted to pH 7.0 by addition of 1 M Tris base. The reduction, oxidation, and conjugation steps for the PBD conjugate were performed at a protein concentration of 20 mg/ml in 20 mM histidine, 1 mm EDTA, pH 7.0. The protein was transferred to a suitable reaction vessel, and the temperature adjusted to 37° C. The reducing agent dithiothreitol (DTT) was added from a freshly prepared 50 mM stock solution at a molar ratio of DTT:mAb=30:1. The solution was incubated with mild agitation at 37° C. for 1 hour. After this incubation time, the reducing agent was removed by dialysis or diafiltration against 20 mM histidine/1 mM EDTA buffer, pH 7.0. The recovered product was filtered through a 0.22 μm filter. For the oxidation, the protein solution was incubated with dehydroascorbic acid (DHA) at a molar ratio of 10:1 (DHA:mAb). Incubation was performed at 22-25° C. for 1 hour with mild agitation (at a 50 rpm mixing speed). After this time, the PBD payload (SG3249) was added from a 10 mM stock solution in DMSO at a molar ratio of payload:mAb of 8.5:1. No additional DMSO was added to this reaction, the effective DMSO concentration due to DHA and payload addition was about 11.4%. The mixture was incubated for 1 hour at 22-25° C. with mild agitation to allow the formation of antibody-drug conjugate. The reaction was then quenched by addition of N-acetylcysteine (NAC) from a 100 mM stock solution at a molar ratio of NAC:PBD of 4:1.

To remove protein fragments, aggregates, and the excess of free PBD payload, post-conjugation purification was performed using ceramic hydroxyapatite (CHT) type I (Bio-Rad). The column was operated in bind-elute mode at a linear flow rate of 180 cm/hr. The pH of the quenched antibody-drug reaction mixture was adjusted to pH 7.0 by addition of 1 M Tris base. The CHT column was pre-equilibrated with 300 mM sodium phosphate, pH 6.5, and equilibrated with 10 mM sodium phosphate, pH 6.5. The antibody-drug conjugate mixture was loaded up to a load challenge of 20 g/L, and the column was re-equilibrated with 10 mM sodium phosphate, pH 6.5. Bound protein was then washed with 10 mM sodium phosphate, 25 mM sodium caprylate, pH 6.5 to remove excess free drug, followed by re-equilibration with 10 mM sodium phosphate, pH 6.5. Elution was performed with a linear gradient from 0.3 to 1 M sodium chloride in 10 mM sodium phosphate, pH 6.5, over 10 column volumes. The elution peak was fractionated, and all fractions analyzed by HP SEC. Fractions containing conjugated protein with a monomer purity >95% were pooled. After each purification cycle, the column is stripped with 2 M sodium chloride, sanitized with 1 N sodium hydroxide, and stored in 0.1 N sodium hydroxide.

The ADC was concentrated and exchanged into the final formulation buffer by tangential flow filtration using either regenerated cellulose or PES membranes with a 30 kDa MWCO. The excipient PS80 was spiked from a 10% stock solution. Final ADC concentration was 5 mg/ml in 20 mM histidine, 240 mM sucrose, 0.02% PS80, pH 6.0.

```
AMINO ACID SEQUENCES:

Original 17c10 VH; SEQ ID NO: 1
QVQLQQWGAGLLKPSETLSLTCAVYGGSFSGYYWSWIRQPPGKGLEWIGEIHHSGGANYNPSLKSRVTISVDTSKNQF
SLKLTSVTAADTAVYYCARGQGKNWHYDYFDYWGQGTLVTVSSA Original 17c10 VL; SEQ ID NO: 2
DIQMTQSPSTLSTSVGDRVTLTCRASQSIRSWLAWYQQNPGKAPKLLIYKASILKIGVPSRFSGSGSGTDFTLTITSL
QPDDFATYYCQQYYSYSRTFGQGTKVEIK Original 1e8 VH; SEQ ID NO: 3
QVQLQQWGAGLLKPSETLSLTCAVYGGSFSGYYWSWIPQPPGKGVEWIGEINHSGSTNYNPSLKSRVTISSDTSKNQF
SLKLTSVTAADTAVYYCARGQGKNWNYDYFDYWGQGTLVTVSSA Original 1e8 VL; SEQ ID NO: 4
DIQMTQSPSTLSASVGDRVTLTCRASQSIRSWLAWYQQKPGKAPKLLIYKASSLKSGVPSRFSGSGSGTDFTLTISSL
QPDDFATYYCQQYYSFSRTFGQGTKVEIK Germlined 17c10 VH; SEQ ID NO: 5
QVQLQQWGAGLLKPSETLSLTCAVYGGSFSGYYWSWIRQPPGKGLEWIGEIHHSGGANYNPSLKSRVTISVDTSKNQF
SLKLSSVTAADTAVYYCARGQGKNWHYDYFDYWGQGTLVTVSSA Germlined 17c10 VL; SEQ ID NO: 6
DIQMTQSPSTLSASVGDRVTITCRASQSIRSWLAWYQQKPGKAPKLLIYKASILKIGVPSRFSGSGSGTEFTLTISSL
QPDDFATYYCQQYYSYSRTFGQGTKVEIK Germlined 1e8 VH; SEQ ID NO: 7
QVQLQQWGAGLLKPSETLSLTCAVYGGSFSGYYWSWIRQPPGKGLEWIGEIHHSGSTNYNPSLKSRVTISVDTSKNQF
SLKLSSVTAADTAVYYCARGQGKNWNYDYFDYWGQGTLVTVSSA Germlined 1e8 VL; SEQ ID NO: 8
DIQMTQSPSTLSASVGDRVTITCRASQSIRSWLAWYQQKPGKAPKLLIYKASSLKSGVPSRFSGSGSGTEFTLTISSL
QPDDFATYYCQQYYSFSRTFGQGTKVEIK Maia Heavy Chain Backbone (Cysteine insertion boxed and in bold); SEQ ID NO: 9
STKGPSVFPLAPSSKSTSGGTAALGCLVKDYFPEPVTVSWNSGALTSGVHTFPAVLQSSGLYSLSSVVTVPSSSLGTQT
YICNVNHKPSNTKVDKRVEPKSCDKTHTCPPCPAPELLGGPS[C]VFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEKTISKAKGQPREPQVYTLPP
SREEMTKNQVSLTCLVKGFYPSDIAVEWESNGQPENNYKTTPPVLDSDGSFFLYSKLTVDKSRWQQGNVFSCSVMHEAL
HNHYTQKSLSLSPGK 17c10 Germlined HCDR1 (Kabat numbering) SEQ ID NO: 10
GYYWS 17c10 Germlined HCDR2 (Kabat numbering); SEQ ID NO: 11
EIHHSGGANYNPSLKS 17c10 Germlined HCDR3 (Kabat numbering); SEQ ID NO: 12
GQGKNWHYDYFDY 17c10 Germlined LCDR1 (Kabat numbering); SEQ ID NO: 13
RASQSIRSWLA 17c10 Germlined LCDR2 (Kabat numbering); SEQ ID NO: 14
KASILKI 17c10 Germlined LCDR3 (Kabat numbering); SEQ ID NO: 15
QQYYSYSRT
```

AMINO ACID SEQUENCES:

```
1e8 Germlined HCDR1 (Kabat numbering); SEQ ID NO: 16
GYYWS

1e8 Germlined HCDR2 (Kabat numbering); SEQ ID NO: 17
EIHHSGSTNYNPSLKS

1e8 Germlined HCDR3 (Kabat numbering); SEQ ID NO: 18
GQGKNWNYDYFDY

1e8 Germlined LCDR1 (Kabat numbering); SEQ ID NO: 19
RASQSIRSWLA

1e8 Germlined LCDR2 (Kabat numbering); SEQ ID NO: 20
KASSLKS

1e8 Germlined LCDR3 (Kabat numbering); SEQ ID NO: 21
QQYYSFSRT

Consensus HCDR2; SEQ ID NO: 22
EIHHSGX1X2NYNPSLKS; where X1 is S or G, and X2 is A or T Consensus HCDR3; SEQ ID NO: 23
GQGKNWX1YDYFDY, where X1 is H or N Consensus LCDR2; SEQ ID NO: 24
KASX1LKX2; where X1 is I or S and X2 is I or S Consensus LCDR3; SEQ ID NO: 25
QQYYSX1SRT, where X1 is Y or F Human Kappa Light Chain; SEQ ID NO: 26
RTVAAPSVFIFPPSDEQLKSGTASVVCLLNNFYPREAKVQWKVDNALQSGNSQESVTEQDSKDSTYSLSSTLTLSKADY
EKHKVYACEVTHQGLSSPVTKSFNRGEC
```

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The present invention is further described by the following claims.

The invention claimed is:

1. An antibody or antigen binding fragment thereof, which specifically binds to an epitope of the neutral amino acid transporter 2 (ASCT2), wherein the antibody or antigen binding fragment comprises three heavy chain complementarity determining regions (HCDRs) of a heavy chain variable region (VH) and three light chain complementarity determining regions (LCDRs) of a light chain variable region (VL), wherein the antibody or antigen-binding fragment thereof comprises an HCDR1 of the amino acid sequence of SEQ ID NO: 10 or SEQ ID NO: 16; an HCDR2 of the amino acid sequence of SEQ ID NO: 11 or SEQ ID NO: 17; an HCDR3 of the amino acid sequence of SEQ ID NO: 12 or SEQ ID NO: 18; an LCDR1 of the amino acid sequence of SEQ ID NO: 13 or SEQ ID NO: 19; an LCDR2 of the amino acid sequence of SEQ ID NO: 14 or SEQ ID NO: 20; and an LCDR3 of the amino acid sequence of SEQ ID NO: 15 or SEQ ID NO: 21.

2. The antibody or antigen binding fragment of claim 1, wherein the VH comprises an amino acid sequence selected from SEQ ID NO: 1; SEQ ID NO: 5; and SEQ ID NO: 7, and wherein the VL comprises an amino acid sequence selected from SEQ ID NO: 2; SEQ ID NO: 4; SEQ ID NO: 6; and SEQ ID NO: 8.

3. The antibody or antigen binding fragment according to claim 2, wherein the VH comprises the amino acid sequence of SEQ ID NO: 5 and the VL comprises the amino acid sequence of SEQ ID NO: 6.

4. The antibody or antigen binding fragment according to claim 2, wherein the VH comprises the amino acid sequence SEQ ID NO: 7 and the VL comprises the amino acid sequence SEQ ID NO: 8.

5. The antibody or antigen binding fragment according to claim 1, wherein the antibody or antigen-binding fragment comprises an IgG constant region comprising a cysteine (C) insertion between the serine (S) at position 239 and the valine (V) at position 240.

6. The antibody or antigen binding fragment according to claim 5, wherein the antibody comprises a heavy chain of an amino acid sequence of SEQ ID NO: 9.

7. The antibody or antigen binding fragment according to claim 1, wherein upon the antibody binding to ASCT2 on the cell surface, the antibody internalizes into the cell.

8. The antibody or antigen binding fragment according to claim 1, which comprises a light chain constant region selected from the group consisting of a human kappa constant region and a human lambda constant region.

9. The antibody or antigen binding fragment according to claim 8, wherein the antibody comprises a human kappa constant region of SEQ ID NO: 26.

10. The antibody or antigen binding fragment according to claim 1, further conjugated to a cytotoxin selected from the group consisting of an antimicrobial agent, a therapeutic agent, a prodrug, a peptide, a protein, an enzyme, a lipid, a biological response modifier, a pharmaceutical agent, a lymphokine, a heterologous antibody, a fragment of a heterologous antibody, a detectable label, a polyethylene glycol (PEG), a radioisotope, and a combination of two or more of any said cytotoxins.

11. The antibody or antigen binding fragment according to claim 10, which is conjugated to a cytotoxin.

12. The antibody or antigen binding fragment according to claim 11, wherein the cytotoxin is selected from a tubulysin derivative and a pyrrolobenzodiazepine.

13. The antibody or antigen binding fragment according to claim 12, wherein the tubulysin derivative is tubulysin AZ1508.

14. The antibody or antigen binding fragment according to claim 12, wherein the pyrrolobenzodiazepine is selected from SG3315 and SG3249.

15. The antibody or antigen binding fragment according to claim 1, wherein the antibody binds to human ASCT2 and cynomolgus monkey ASCT2.

16. The antibody or antigen binding fragment according to claim 1, wherein the antibody does not specifically bind to human ASCT1.

17. A pharmaceutical composition comprising an antibody or antigen binding fragment of claim 1 and a pharmaceutically acceptable carrier.

18. A polynucleotide or combination of polynucleotides encoding the antibody or antigen binding fragment thereof according to claim 1.

19. A method of making an antibody or antigen binding fragment thereof comprising culturing a host comprising a polynucleotide of claim 18.

20. A method of treating a cancer characterized by overexpression of ASCT2 in a subject, the method comprising administering to a subject in need of treatment an effective amount of the antibody or antigen binding fragment of claim 1.

* * * * *

SEQUENCE LISTING

```
<160> NUMBER OF SEQ ID NOS: 27

<210> SEQ ID NO 1
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile His His Ser Gly Gly Ala Asn Tyr Asn Pro Ser Leu Lys
    50                  55                  60

Ser Arg Val Thr Ile Ser Val Asp Thr Ser Lys Asn Gln Phe Ser Leu
```

```
                65                  70                  75                  80
Lys Leu Thr Ser Val Thr Ala Ala Asp Thr Ala Val Tyr Tyr Cys Ala
                    85                  90                  95

Arg Gly Gln Gly Lys Asn Trp His Tyr Asp Tyr Phe Asp Tyr Trp Gly
                100                 105                 110

Gln Gly Thr Leu Val Thr Val Ser Ser Ala
            115                 120
```

<210> SEQ ID NO 2
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

```
Asp Ile Gln Met Thr Gln Ser Pro Ser Thr Leu Ser Thr Ser Val Gly
1               5                   10                  15

Asp Arg Val Thr Leu Thr Cys Arg Ala Ser Gln Ser Ile Arg Ser Trp
                20                  25                  30

Leu Ala Trp Tyr Gln Gln Asn Pro Gly Lys Ala Pro Lys Leu Leu Ile
            35                  40                  45

Tyr Lys Ala Ser Ile Leu Lys Ile Gly Val Pro Ser Arg Phe Ser Gly
50                  55                  60

Ser Gly Ser Gly Thr Asp Phe Thr Leu Thr Ile Thr Ser Leu Gln Pro
65                  70                  75                  80

Asp Asp Phe Ala Thr Tyr Tyr Cys Gln Gln Tyr Ser Tyr Ser Arg
                85                  90                  95

Thr Phe Gly Gln Gly Thr Lys Val Glu Ile Lys
                100                 105
```

<210> SEQ ID NO 3
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Pro Gln Pro Pro Gly Lys Gly Val Glu Trp Ile
            35                  40                  45

Gly Glu Ile Asn His Ser Gly Ser Thr Asn Tyr Asn Pro Ser Leu Lys
    50                  55                  60

Ser Arg Val Thr Ile Ser Ser Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Gly Gln Gly Lys Asn Trp Asn Tyr Asp Tyr Phe Asp Tyr Trp Gly
                100                 105                 110

Gln Gly Thr Leu Val Thr Val Ser Ser Ala
            115                 120
```

```
<210> SEQ ID NO 4
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Asp Ile Gln Met Thr Gln Ser Pro Ser Thr Leu Ser Ala Ser Val Gly
1               5                   10                  15

Asp Arg Val Thr Leu Thr Cys Arg Ala Ser Gln Ser Ile Arg Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Lys Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Tyr Ser Phe Ser Arg
                85                  90                  95

Thr Phe Gly Gln Gly Thr Lys Val Glu Ile Lys
            100                 105

<210> SEQ ID NO 5
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile His His Ser Gly Gly Ala Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gln Gly Lys Asn Trp His Tyr Asp Tyr Phe Asp Tyr Trp Gly
            100                 105                 110

Gln Gly Thr Leu Val Thr Val Ser Ser Ala
        115                 120

<210> SEQ ID NO 6
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 6

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Arg Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ile Leu Lys Ile Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Ser Tyr Ser Arg
                85                  90                  95

Thr Phe Gly Gln Gly Thr Lys Val Glu Ile Lys
            100                 105

<210> SEQ ID NO 7
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile His His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gln Gly Lys Asn Trp Asn Tyr Asp Tyr Phe Asp Tyr Trp Gly
            100                 105                 110

Gln Gly Thr Leu Val Thr Val Ser Ser Ala
        115                 120

<210> SEQ ID NO 8
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Arg Ser Trp
            20                  25                  30

Leu Ala Trp Tyr Gln Gln Lys Pro Gly Lys Ala Pro Lys Leu Leu Ile

```
                35                  40                  45
Tyr Lys Ala Ser Ser Leu Lys Ser Gly Val Pro Ser Arg Phe Ser Gly
             50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Tyr Ser Phe Ser Arg
                 85                  90                  95

Thr Phe Gly Gln Gly Thr Lys Val Glu Ile Lys
            100                 105

<210> SEQ ID NO 9
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ser Thr Lys Gly Pro Ser Val Phe Pro Leu Ala Pro Ser Ser Lys Ser
 1               5                  10                  15

Thr Ser Gly Gly Thr Ala Ala Leu Gly Cys Leu Val Lys Asp Tyr Phe
             20                  25                  30

Pro Glu Pro Val Thr Val Ser Trp Asn Ser Gly Ala Leu Thr Ser Gly
         35                  40                  45

Val His Thr Phe Pro Ala Val Leu Gln Ser Ser Gly Leu Tyr Ser Leu
     50                  55                  60

Ser Ser Val Val Thr Val Pro Ser Ser Ser Leu Gly Thr Gln Thr Tyr
 65                  70                  75                  80

Ile Cys Asn Val Asn His Lys Pro Ser Asn Thr Lys Val Asp Lys Arg
                 85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 10
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Tyr Tyr Trp Ser
1               5
```

```
<210> SEQ ID NO 11
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Glu Ile His His Ser Gly Gly Ala Asn Tyr Asn Pro Ser Leu Lys Ser
1               5                   10                  15
```

```
<210> SEQ ID NO 12
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Gln Gly Lys Asn Trp His Tyr Asp Tyr Phe Asp Tyr
1               5                   10
```

```
<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Arg Ala Ser Gln Ser Ile Arg Ser Trp Leu Ala
1               5                   10
```

```
<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 14

Lys Ala Ser Ile Leu Lys Ile
1               5

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gln Gln Tyr Tyr Ser Tyr Ser Arg Thr
1               5

<210> SEQ ID NO 16
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Tyr Tyr Trp Ser
1               5

<210> SEQ ID NO 17
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Glu Ile His His Ser Gly Ser Thr Asn Tyr Asn Pro Ser Leu Lys Ser
1               5                   10                  15

<210> SEQ ID NO 18
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gly Gln Gly Lys Asn Trp Asn Tyr Asp Tyr Phe Asp Tyr
1               5                   10

<210> SEQ ID NO 19
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Arg Ala Ser Gln Ser Ile Arg Ser Trp Leu Ala
```

```
1               5                    10
```

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

```
Lys Ala Ser Ser Leu Lys Ser
1               5
```

<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

```
Gln Gln Tyr Tyr Ser Phe Ser Arg Thr
1               5
```

<210> SEQ ID NO 22
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (7)..(7)
<223> OTHER INFORMATION: /replace="Gly"
<220> FEATURE:
<221> NAME/KEY: VARIANT
<222> LOCATION: (8)..(8)
<223> OTHER INFORMATION: /replace="Thr"
<220> FEATURE:
<221> NAME/KEY: MISC_FEATURE
<222> LOCATION: (1)..(9)
<223> OTHER INFORMATION: /note="Variant residues given in the sequence
      have no preference with respect to those in the annotations for
      variant positions"

<400> SEQUENCE: 22

```
Glu Ile His His Ser Gly Ser Ala Asn Tyr Asn Pro Ser Leu Lys Ser
1               5                   10                  15
```

<210> SEQ ID NO 23
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (7)..(7)
<223> OTHER INFORMATION: /replace="Asn"
<220> FEATURE:
<221> NAME/KEY: MISC_FEATURE
<222> LOCATION: (1)..(9)
<223> OTHER INFORMATION: /note="Variant residues given in the sequence
      have no preference with respect to those in the annotations for variant positions"

<400> SEQUENCE: 23

Gly Gln Gly Lys Asn Trp His Tyr Asp Tyr Phe Asp Tyr
1               5                   10

<210> SEQ ID NO 24
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Ser"
<220> FEATURE:
<221> NAME/KEY: VARIANT
<222> LOCATION: (7)..(7)
<223> OTHER INFORMATION: /replace="Ser"
<220> FEATURE:
<221> NAME/KEY: MISC_FEATURE
<222> LOCATION: (1)..(9)
<223> OTHER INFORMATION: /note="Variant residues given in the sequence
      have no preference with respect to those in the annotations for
      variant positions"

<400> SEQUENCE: 24

Lys Ala Ser Ile Leu Lys Ile
1               5

<210> SEQ ID NO 25
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="Phe"
<220> FEATURE:
<221> NAME/KEY: MISC_FEATURE
<222> LOCATION: (1)..(9)
<223> OTHER INFORMATION: /note="Variant residues given in the sequence
      have no preference with respect to those in the annotations for
      variant positions"

<400> SEQUENCE: 25

Gln Gln Tyr Tyr Ser Tyr Ser Arg Thr
1               5

<210> SEQ ID NO 26
<211> LENGTH: 107
<212> TYPE: PRT
<213> ORGANISM: Homo sapiens

<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser

```
                50                  55                  60
Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 27
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 27

His His His His His His
1               5
```